United States Patent
Goto et al.

(10) Patent No.: US 10,985,327 B2
(45) Date of Patent: Apr. 20, 2021

(54) MICROCRYSTALLINE ORGANIC SEMICONDUCTOR FILM, ORGANIC SEMICONDUCTOR TRANSISTOR, AND METHOD OF MANUFACTURING ORGANIC SEMICONDUCTOR TRANSISTOR

(71) Applicant: FUJIFILM Corporation, Tokyo (JP)

(72) Inventors: Takashi Goto, Kanagawa (JP); Eiji Fukuzaki, Kanagawa (JP); Tetsuya Watanabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 54 days.

(21) Appl. No.: 16/358,910

(22) Filed: Mar. 20, 2019

(65) Prior Publication Data

US 2019/0237677 A1    Aug. 1, 2019

Related U.S. Application Data

(63) Continuation of application No. PCT/JP2017/033407, filed on Sep. 15, 2017.

(30) Foreign Application Priority Data

Sep. 29, 2016  (JP) .............................. JP2016-191913

(51) Int. Cl.
| | |
|---|---|
| *H01L 51/00* | (2006.01) |
| *C07D 517/14* | (2006.01) |
| *C07D 493/14* | (2006.01) |
| *C07D 495/14* | (2006.01) |
| *C07D 513/14* | (2006.01) |
| *C07D 498/14* | (2006.01) |

(Continued)

(52) U.S. Cl.
CPC ........ *H01L 51/0071* (2013.01); *C07D 493/14* (2013.01); *C07D 495/14* (2013.01); *C07D 498/14* (2013.01); *C07D 513/14* (2013.01); *C07D 517/14* (2013.01); *H01L 29/786* (2013.01); *H01L 51/0065* (2013.01); *H01L 51/0067* (2013.01); *H01L 51/0068* (2013.01); *H01L 51/0072* (2013.01); *H01L 51/0073* (2013.01); *H01L 51/0074* (2013.01); *H01L 51/05* (2013.01); *H01L 51/001* (2013.01); *H01L 51/0558* (2013.01)

(58) Field of Classification Search
CPC . H01L 51/0071; H01L 51/05; H01L 51/0074; H01L 51/0065; H01L 51/0072; H01L 51/0073; H01L 51/0067; H01L 51/0068; H01L 51/0558; H01L 29/786; H01L 51/001; C07D 517/14; C07D 493/14; C07D 495/14; C07D 513/14; C07D 498/14

See application file for complete search history.

(56) References Cited

U.S. PATENT DOCUMENTS

| | | |
|---|---|---|
| 2015/0340630 A1 | 11/2015 | Im et al. |
| 2016/0365519 A1 | 12/2016 | Jiao et al. |

(Continued)

FOREIGN PATENT DOCUMENTS

| | | |
|---|---|---|
| JP | 2008-085250 A | 4/2008 |
| JP | 2015-195361 A | 11/2015 |

(Continued)

OTHER PUBLICATIONS

Extended European Search Report issued by the European Patent Office dated Oct. 9, 2019, which corresponds to EP17855775.7-1211 and is related to U.S. Appl. No. 16/358,910.

An Office Action mailed by the Japanese Patent Office dated Nov. 26, 2019, which corresponds to Japanese Patent Application No. 2018-542392 and is related to U.S. Appl. No. 16/358,910.

(Continued)

*Primary Examiner* — John M Mauro

(74) *Attorney, Agent, or Firm* — Studebaker & Brackett PC

(57) ABSTRACT

Provided are an organic semiconductor film, an organic semiconductor transistor formed of the organic semiconductor film, and a method of manufacturing the organic semiconductor transistor. In the organic semiconductor film, the formation or propagation of cracks can be effectively suppressed even in a case where the organic semiconductor film is patterned or is exposed to high heat.

Provided are an organic semiconductor film, an organic semiconductor transistor formed of the organic semiconductor film, and a method of manufacturing the organic semiconductor transistor. The microcrystalline organic semiconductor film includes a compound represented by the following Formula (1) that has a molecular weight of 3000 or lower and in which a crystal domain size is 1 nm to 100 nm.

Formula (1)

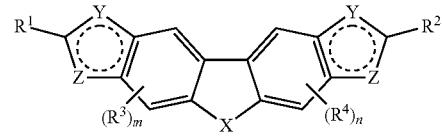

X, Y, and Z each independently represent a specific ring-constituting atom. $R^1$ and $R^2$ each independently represent a hydrogen atom, an alkyl group, an alkenyl group, an alkynyl group, an aryl group, or a heteroaryl group. $R^3$ and $R^4$ each independently represent a halogen atom, an alkyl group, an alkenyl group, an alkynyl group, an aryl group, or a heteroaryl group. m and n each independently represent an integer of 0 to 2.

21 Claims, 3 Drawing Sheets

(51) Int. Cl.
  H01L 29/786  (2006.01)
  H01L 51/05  (2006.01)

(56) References Cited

U.S. PATENT DOCUMENTS

| | | |
|---|---|---|
| 2017/0012220 A1 | 1/2017 | Tsuyama et al. |
| 2017/0018724 A1 | 1/2017 | Tsuyama et al. |
| 2017/0179415 A1 | 6/2017 | Niori |

FOREIGN PATENT DOCUMENTS

| | | | | |
|---|---|---|---|---|
| JP | 2015-195362 A | 11/2015 | | |
| WO | WO-2011126225 A1 * | 10/2011 | ............. | C09K 11/06 |
| WO | 2015/128779 A1 | 9/2015 | | |
| WO | 2016/047587 A1 | 3/2016 | | |

OTHER PUBLICATIONS

International Search Report issued in PCT/JP2017/033407; dated Nov. 7, 2017.
Written Opinion of the International Searching Authority issued in PCT/JP2017/033407; dated Nov. 7, 2017.

* cited by examiner

MICROCRYSTALLINE ORGANIC SEMICONDUCTOR FILM, ORGANIC SEMICONDUCTOR TRANSISTOR, AND METHOD OF MANUFACTURING ORGANIC SEMICONDUCTOR TRANSISTOR

CROSS-REFERENCE TO RELATED APPLICATIONS

This application is a Continuation of PCT International Application No. PCT/JP2017/033407 filed on Sep. 15, 2017, which claims priorities under 35 U.S.C. § 119 (a) to Japanese Patent Application No. JP2016-191913 filed on Sep. 29, 2016. Each of the above applications is hereby expressly incorporated by reference, in its entirety, into the present application.

BACKGROUND OF THE INVENTION

1. Field of the Invention

The present invention relates to a microcrystalline organic semiconductor film, an organic semiconductor transistor, and a method of manufacturing an organic semiconductor transistor.

2. Description of the Related Art

In a display such as a liquid crystal display or an organic electroluminescence display or a logical circuit such as a radio frequency identifier (RFID: RF tag) or a memory, a micro transistor such as a switching element is integrated. An organic semiconductor transistor (field effect transistor) in which an organic semiconductor compound is used for forming a semiconductor layer can be reduced in weight and also has excellent flexibility. Thus, the organic semiconductor transistor has attracted attention as the next-generation transistor that is an alternative to a transistor including a silicon semiconductor layer, and development thereof has progressed.

In order to improve the performance of the organic semiconductor transistor, the improvement of carrier mobility is an important factor. By increasing the carrier mobility, high-speed switching can be performed with a small electric field, and improvement of processing speed and low power consumption can be realized. In order to realize the improvement of mobility, a chemical structure of an organic semiconductor used for forming an organic semiconductor layer has been investigated. For example, JP2015-195361A and JP2015-195362A describe that a specific aromatic compound that has a fused polycyclic structure including a heteroatom bonded to a ring-constituting atom is used for forming a semiconductor active layer (organic semiconductor layer) of a transistor such that the transistor exhibits excellent carrier mobility.

SUMMARY OF THE INVENTION

In the techniques described in JP2015-195361A and JP2015-195362A, high mobility is realized by forming an organic semiconductor layer using a coating solution in which an organic semiconductor compound is dissolved and precipitating organic semiconductor crystals in the organic semiconductor layer. In the techniques described in JP2015-195361A and JP2015-195362A, the precipitation of the organic semiconductor crystals is observed with a polarizing microscope, but only crystals having a large crystal domain size can be observed with the polarizing microscope. That is, in the techniques described in JP2015-195361A and JP2015-195362A, the domain size of the crystals precipitated in the organic semiconductor layer exceeds several micrometers.

The present inventors conducted an investigation on the performance of the transistor in which the organic semiconductor layer is formed of the compound described in each of JP2015-195361A and JP2015-195362A, and found that a large crystal domain size of the film cause a problem during the integration of the transistor. More specifically, in the case of the patterning of the organic semiconductor layer during integration (in the present invention, unless specified otherwise, "patterning" simply refers to a process of forming the organic semiconductor layer in a desired shape using an external physical force or a chemical action, for example, scribing of the organic semiconductor layer using a needle or etching of the organic semiconductor layer), cracks formed in an end portion of the film are likely to propagate to the entire crystal domain, which leads to a problem of deterioration of performance. In a case where these cracks reach a channel portion, carrier transport is largely interrupted, and a desired carrier mobility cannot be obtained. That is, the performance of the obtained organic semiconductor transistor is likely to vary.

In addition, it has been clarified that the crystal domain size of the organic semiconductor layer and heat stability have a negative correlation. That is, in the techniques described in JP2015-195361A and JP2015-195362A, in a case where a heating step (for example, a firing step or a sealing step) is performed as a post step after the formation of the organic semiconductor layer, cracks are likely to be formed in a crystalline structure due to thermal expansion or the like and cause deterioration in carrier mobility. That is, in a case where the compound described in each of JP2015-195361A and JP2015-195362A is used for forming an organic semiconductor layer of a transistor, even when the organic semiconductor layer is exposed to heat, the performance of the obtained organic semiconductor transistor is likely to vary.

In addition, in the techniques described in JP2015-195361A and JP2015-195362A, the crystal domain size of the organic semiconductor layer is large. Therefore, a solvent remaining in the organic semiconductor layer in the step of forming the organic semiconductor layer is likely to remain without being volatilized. In a bottom gate type transistor, a solvent may remain between a gate insulating layer and an organic semiconductor layer, and it is presumed that this residual solvent causes an increase in the absolute value of a threshold voltage or deterioration in the hysteresis of a threshold voltage.

In addition, in a bottom contact type transistor, typically, there is a difference in wettability between an insulating film and an electrode. Therefore, even in a case where the compound described in each of JP2015-195361A and JP2015-195362A is used, it may be difficult to form a crystalline film having a large domain size that covers the entire channel region. That is, it may be difficult to make the entire organic semiconductor film to be in a uniform crystalline state, which causes a variation in the performance of the obtained organic semiconductor transistor.

Therefore, an object of the present invention is to provide an organic semiconductor film that is formed using the aromatic compound having the specific structure described in JP2015-195361A or JP2015-195362A and in which the occurrence or propagation of cracks can be effectively suppressed even in a case where an external physical force or high heat is applied thereto during patterning or the like.

In addition, another object of the present invention is to provide an organic semiconductor transistor in which a variation in performance between elements is small and power consumption is also suppressed and a method of manufacturing the organic semiconductor transistor.

The present inventors repeatedly conducted a thorough investigation in consideration of the above-described objects and found that, by using vapor deposition to form a film using the aromatic compound having the specific structure described in JP2015-195361A or JP2015-195362A, a microcrystalline organic semiconductor film having an extremely small crystal domain size can be obtained and cracks are not likely to be formed and, even if cracks are formed, the cracks are not likely to propagate even in a case where the microcrystalline organic semiconductor film is patterned or is exposed to heat during firing or the like. Further, the present inventors found that, by using this microcrystalline organic semiconductor film as an organic semiconductor layer of an organic semiconductor transistor, a variation in performance between the obtained transistor elements can be highly suppressed and an element having a low absolute value of a threshold voltage and low power consumption can be provided. The present invention has been completed based on the above findings as a result of repeated investigation.

The object of the present invention is achieved by the following means.

[1] A microcrystalline organic semiconductor film comprising:
a compound represented by the following Formula (1) that has a molecular weight of 3000 or lower and in which a crystal domain size is 1 nm to 100 nm, Formula (1)

in Formula (1),

X represents an oxygen atom, a sulfur atom, a selenium atom, a tellurium atom, or $NR^5$, Y and Z each independently represent $CR^6$, an oxygen atom, a sulfur atom, a selenium atom, a nitrogen atom, or $NR^7$, a 5-membered ring including Y and Z is an aromatic heterocycle, $R^1$ and $R^2$ in Formula (1) are bonded to a ring-constituting atom of the 5-membered ring including Y and Z directly or indirectly through a divalent group A, $R^3$ and $R^4$ in Formula (1) are bonded to a ring-constituting atom of a benzene ring directly or indirectly through the divalent group A, the divalent group A is a group selected from —O—, —S—, —$NR^8$—, —CO—, —SO—, or —$SO_2$— or is a group in which two or more selected from —O—, —S—, —$NR^8$—, —CO—, —SO—, or —$SO_2$— are linked to each other, $R^1$, $R^2$, $R^5$, $R^6$, $R^7$, and $R^8$ each independently represent a hydrogen atom, an alkyl group, an alkenyl group, an alkynyl group, an aryl group, or a heteroaryl group, $R^3$ and $R^4$ each independently represent a halogen atom, an alkyl group, an alkenyl group, an alkynyl group, an aryl group, or a heteroaryl group, m and n each independently represent an integer of 0 to 2, and a configuration in which X represents an oxygen atom or a sulfur atom and the 5-membered ring including Y and Z is an imidazole ring and a configuration in which X represents a sulfur atom, Y represents CH, Z represents a sulfur atom, both $R^1$ and $R^2$ represent a hydrogen atom, and both m and n represent 0 are excluded from the compound represented by Formula (1).

[2] The microcrystalline organic semiconductor film according to [1],
in which the 5-membered ring including Y and Z is a ring selected from a thiophene ring, a furan ring, a selenophene ring, a pyrrole ring, a thiazole ring, or an oxazole ring.

[3] The microcrystalline organic semiconductor film according to [1] or [2],
in which the number of carbon atoms in each of $R^1$, $R^2$, $R^3$, and $R^4$ is 30 or less.

[4] The microcrystalline organic semiconductor film according to any one of [1] to [3],
in which $R^1$ and $R^2$ each independently represent an alkyl group having 20 or less carbon atoms, an aryl group having 20 or less carbon atoms, or a heteroaryl group having 20 or less carbon atoms.

[5] The microcrystalline organic semiconductor film according to any one of [1] to [4],
in which $R^1$ and $R^2$ are the same as each other,
$R^3$ and $R^4$ are the same as each other, and
m and n are the same as each other.

[6] The microcrystalline organic semiconductor film according to any one of [1] to [5],
in which both m and n represent 0.

[7] The microcrystalline organic semiconductor film according to [1], in which the compound represented by the following Formula (1) that has a molecular weight of 3000 or lower is represented by the following Formula (2) or (3), Formula (2)

Formula (3)

in Formulae (2) and (3), $X^a$ represents an oxygen atom, a sulfur atom, or a selenium atom, $Y^a$ and $Z^a$ each independently represent an oxygen atom, a sulfur atom, a selenium atom, or $NR^{7a}$, $R^{7a}$ has the same definition as $R^7$ in Formula (1), $R^{1a}$, $R^{2a}$, $R^{3a}$, $R^{4a}$, $m^a$, and $n^a$ have the same definitions as $R^1$, $R^2$, $R^3$, $R^4$, m, and n in Formula (1), respectively, binding forms of $R^{1a}$, $R^{2a}$, $R^{3a}$, and $R^{4a}$ to a ring-constituting atom are also the same as binding forms of $R^1$, $R^2$, $R^3$, and $R^4$ in Formula (1) to a ring-constituting atom, respectively, and a configuration in which $X^a$ represents a sulfur atom, $Z^a$ represents a sulfur atom, both $R^{1a}$ and $R^{2a}$ represent a hydrogen atom, and both $m^a$ and $n^a$ represent 0 is excluded from the compound represented by Formula (2).

[8] The microcrystalline organic semiconductor film according to [7], in which the number of carbon atoms in each of $R^{1a}$, $R^{2a}$, $R^{3a}$, and $R^{4a}$ is 30 or less.

[9] The microcrystalline organic semiconductor film according to [7] or [8], in which $R^{1a}$ and $R^{2a}$ each independently represent an alkyl group having 20 or less carbon atoms, an aryl group having 20 or less carbon atoms, or a heteroaryl group having 20 or less carbon atoms.

[10] The microcrystalline organic semiconductor film according to any one of [7] to [9], in which $R^{1a}$ and $R^{2a}$ are the same as each other, $R^{3a}$ and $R^{4a}$ are the same as each other, and $m^a$ and $n^a$ are the same as each other.

[11] The microcrystalline organic semiconductor film according to [7], in which the compound represented by Formula (2) that has a molecular weight of 3000 or lower is represented by the following Formula (4), and the compound represented by Formula (3) that has a molecular weight of 3000 or lower is represented by the following Formula (5),

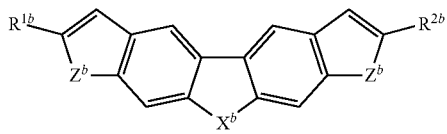

Formula (4)

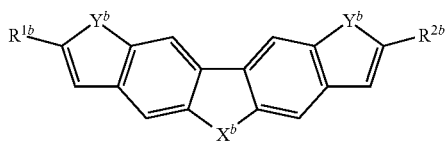

Formula (5)

in Formulae (4) and (5), $X^b$, $Y^b$, and $Z^b$ each independently represent an oxygen atom, a sulfur atom, or a selenium atom, $R^{1b}$ and $R^{2b}$ have the same definitions as $R^{1a}$ and $R^{2a}$ in Formula (2), respectively, binding forms of $R^{1b}$ and $R^{2b}$ to a ring-constituting atom are also the same as binding forms of $R^{1a}$ and $R^{2a}$ in Formula (2) to a ring-constituting atom, respectively, and a configuration in which $X^b$ represents a sulfur atom, $Z^b$ represents a sulfur atom, and both $R^{1b}$ and $R^{2b}$ represent a hydrogen atom is excluded from the compound represented by Formula (4).

[12] The microcrystalline organic semiconductor film according to [11], in which the number of carbon atoms in each of $R^{1b}$ and $R^{2b}$ is 30 or less.

[13] The microcrystalline organic semiconductor film according to [11] or [12], in which $R^{1b}$ and $R^{2b}$ each independently represent an alkyl group having 20 or less carbon atoms, an aryl group having 20 or less carbon atoms, or a heteroaryl group having 20 or less carbon atoms.

[14] The microcrystalline organic semiconductor film according to any one of [11] to [13], in which $R^{1b}$ and $R^{2b}$ have an aliphatic hydrocarbon group.

[15] The microcrystalline organic semiconductor film according to [14], in which $R^{1b}$ and $R^{2b}$ each independently represent an aryl group having a linear aliphatic hydrocarbon group or a heteroaryl group having a linear aliphatic hydrocarbon group.

[16] The microcrystalline organic semiconductor film according to any one of [1] to [15], which is a deposited film.

[17] An organic semiconductor transistor comprising:

the microcrystalline organic semiconductor film according to any one of [1] to [16] as an organic semiconductor layer.

[18] The organic semiconductor transistor according to [17], in which the organic semiconductor transistor is a bottom gate type.

[19] The organic semiconductor transistor according to [17] or [18], in which the organic semiconductor transistor is a bottom contact type.

[20] A method of manufacturing an organic semiconductor transistor comprising:

vapor-depositing a compound represented by the following Formula (1) that has a molecular weight of 3000 or lower to form an organic semiconductor layer,

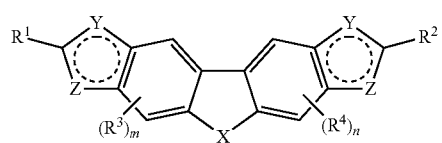

Formula (1)

in Formula (1),

X represents an oxygen atom, a sulfur atom, a selenium atom, a tellurium atom, or $NR^5$, Y and Z each independently represent $CR^6$, an oxygen atom, a sulfur atom, a selenium atom, a nitrogen atom, or $NR^7$, a 5-membered ring including Y and Z is an aromatic heterocycle, $R^1$ and $R^2$ in Formula (1) are bonded to a ring-constituting atom of the 5-membered ring including Y and Z directly or indirectly through a divalent group A, $R^3$ and $R^4$ in Formula (1) are bonded to a ring-constituting atom of a benzene ring directly or indirectly through the divalent group A, the divalent group A is a group selected from —O—, —S—, —$NR^8$—, —CO—, —SO—, or —$SO_2$— or is a group in which two or more selected from —O—, —S—, —$NR^8$—, —CO—, —SO—, or —$SO_2$— are linked to each other, $R^1$, $R^2$, $R^5$, $R^6$, $R^7$, and $R^8$ each independently represent a hydrogen atom, an alkyl group, an alkenyl group, an alkynyl group, an aryl group, or a heteroaryl group, $R^3$ and $R^4$ each independently represent a halogen atom, an alkyl group, an alkenyl group, an alkynyl group, an aryl group, or a heteroaryl group, m and n each independently represent an integer of 0 to 2, and a configuration in which X represents an oxygen atom or a sulfur atom and the 5-membered ring including Y and Z is an imidazole ring and a configuration in which X represents a sulfur atom, Y represents CH, Z represents a sulfur atom, both R¹ and R² represent a hydrogen atom, and both m and n represent 0 are excluded from the compound represented by Formula (1).

[21] The method of manufacturing an organic semiconductor transistor according to any one of [17] to [19] comprising:

forming the microcrystalline organic semiconductor film according to any one of [1] to [16] and patterning the microcrystalline organic semiconductor film to form an organic semiconductor layer.

Even in a case where the microcrystalline organic semiconductor film according to the present invention is patterned or is exposed to heat during firing or the like, cracks are not likely to be formed and, even if cracks are formed, the cracks are not likely to propagate. In the organic semiconductor transistor according to the present invention, the organic semiconductor layer is formed of the microcrystalline organic semiconductor film according to the present invention, a variation in performance between transistor elements is significantly suppressed, and power consumption is also low.

With the manufacturing method according to the present invention, an organic semiconductor transistor having a small variation in performance between elements and having low power consumption can be obtained.

The above-described and other characteristics and advantageous effects of the present invention will be clarified from the following description appropriately with reference to the accompanying drawings.

DESCRIPTION OF THE PREFERRED EMBODIMENTS

Figure 1:
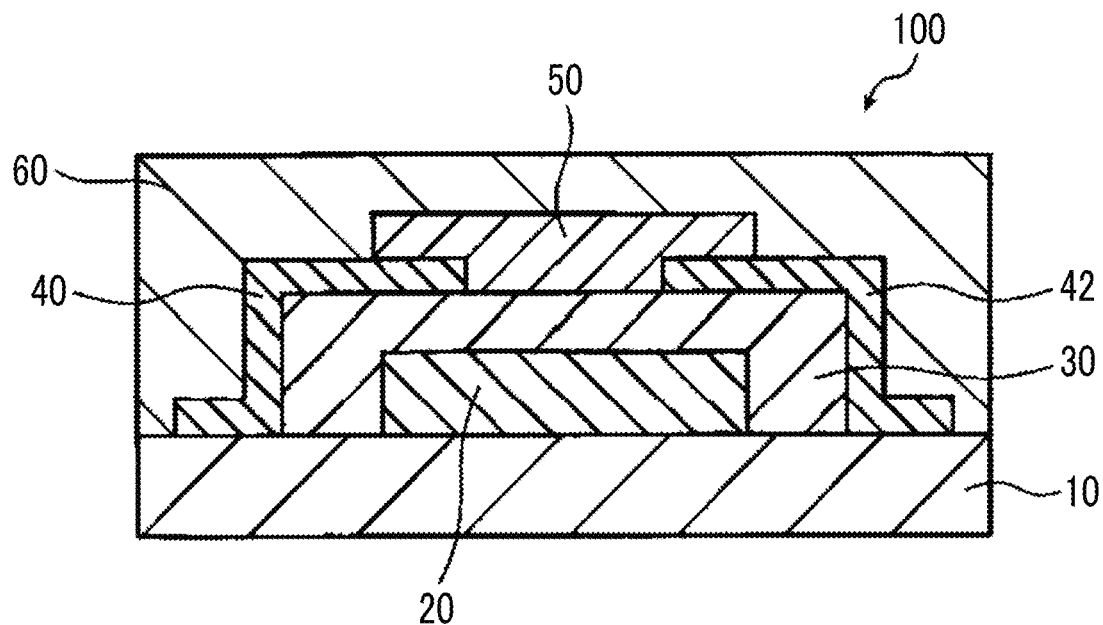
FIG. 1 is a schematic cross-sectional view showing one aspect of a bottom gate-bottom contact type organic semiconductor transistor as an example of an organic semiconductor transistor according to the present invention.

In this specification, numerical ranges represented by "to" include numerical values before and after "to" as lower limit values and upper limit values.

The meaning of compounds described in this specification include not only the compounds themselves but also salts and ions thereof. In addition, within a range where a desired effect does not deteriorate, a part of the structure may be changed.

In addition, in a case where it is not clearly described that a compound is substituted or unsubstituted, this compound has any substituent within a range where a desired effect does not deteriorate. The same shall be applied to a substituent, a linking group, a ring structure, or the like (hereinafter, referred to as "substituent or the like").

In this specification, in a case where a plurality of substituents or the like represented by a specific reference numeral are present or a plurality of substituents or the like are simultaneously defined, the respective substituents or the like may be the same as or different from each other unless specified otherwise. The same shall be applied to definition of the number of substituents or the like. In addition, in a case where a plurality of substituents or the like are close to (in particular, adjacent to) each other, the substituents or the like may be linked to each other to form a ring unless specified otherwise.

In addition, in a case where the number of carbon atoms in a group is described, the number of carbon atoms in this group represents the total number of carbon atoms including substituents unless specified otherwise.

In the present invention, in a case where a group can form an acyclic skeleton and a cyclic skeleton, this group includes a group having an acyclic skeleton and a group having a cyclic skeleton unless specified otherwise. For example, an alkyl group includes a linear alkyl group, a branched alkyl group, and a cycloalkyl group. In a case where a group can form a cyclic skeleton, the lower limit of the number of atoms of the group forming a cyclic skeleton is not limited to the lower limit of the number of atoms specifically described regarding this group, and is 3 or more and preferably 5 or more.

Hereinafter, a preferred embodiment of the present invention will be described.

[Microcrystalline Organic Semiconductor Film]

A microcrystalline organic semiconductor film according to the embodiment of the present invention (hereinafter, also referred to as "microcrystalline film according to the embodiment of the present invention") includes a compound represented by the following Formula (1) that has a molecular weight of 3000 or lower. A crystal domain size of the microcrystalline film according to the embodiment of the present invention is preferably in a range of 1 nm to 100 nm, more preferably in a range of 2 to 90 nm, still more preferably in a range of 3 to 80 nm, and still more preferably in a range of 5 to 80 nm.

In the present invention, the crystal domain size refers to the size of one crystal domain and is measured with a method described below in Examples using an atomic force microscope.

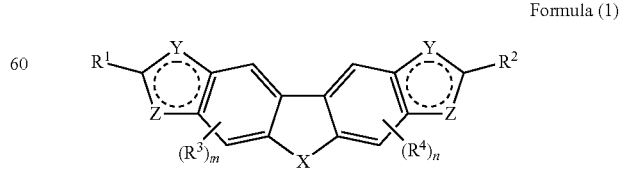

Formula (1)

In Formula (1), X represents an oxygen atom, a sulfur atom, a selenium atom, a tellurium atom, or NR⁵. From the viewpoint of carrier mobility during application to an organic semiconductor layer of a transistor, it is preferable that X represents an oxygen atom, a sulfur atom, or a selenium atom. The details of $R^5$ will be described below.

Y and Z each independently represent $CR^6$, an oxygen atom, a sulfur atom, a selenium atom, a nitrogen atom, or $NR^7$, and a 5-membered ring including Y and Z is an aromatic heterocycle, The details of $R^6$ and $R^7$ will be described below.

Y represents preferably $CR^6$, an oxygen atom, or a sulfur atom and more preferably $CR^6$ or a sulfur atom. In addition, Z represents preferably $CR^6$, an oxygen atom, a sulfur atom, or $NR^7$, more preferably $CR^6$, an oxygen atom, or a sulfur atom, and still more preferably $CR^6$ or a sulfur atom.

In a case where Y represents $CR^6$, Z represents preferably an oxygen atom, a sulfur atom, a selenium atom, or $NR^7$, more preferably an oxygen atom, a sulfur atom, or a selenium atom, still more preferably an oxygen atom or a sulfur atom, and still more preferably a sulfur atom.

In addition, in a case where Y represents an oxygen atom, Z represents preferably $CR^6$, an oxygen atom, or a sulfur atom, more preferably CR6, or a sulfur atom, and still more preferably $CR^6$.

In a case where Y represents a sulfur atom, Z represents preferably $CR^6$, an oxygen atom, a sulfur atom, or a nitrogen atom, more preferably $CR^6$ or a nitrogen atom, and still more preferably $CR^6$.

In a case where Z represents $CR^6$, Y represents preferably an oxygen atom, a sulfur atom, a selenium atom, or $NR^7$, and more preferably an oxygen atom, a sulfur atom, or a selenium atom.

In Formula (1), the aromatic heterocycle in the 5-membered ring including Y and Z is preferably a ring selected from a thiophene ring, a furan ring, a selenophene ring, a pyrrole ring, a thiazole ring, or an oxazole ring, more preferably a thiophene ring, a furan ring, a selenophene ring, or a pyrrole ring, and still more preferably a thiophene ring or a selenophene ring.

In Formula (1), $R^1$ and $R^2$ each independently represent a hydrogen atom, an alkyl group, an alkenyl group, an alkynyl group, an aryl group, or a heteroaryl group. $R^1$ and $R^2$ each independently represent preferably an alkyl group, an alkenyl group, an alkynyl group, an aryl group, or a heteroaryl group, and more preferably an alkyl group, an aryl group, or a heteroaryl group.

The number of carbon atoms in the alkyl group which may be used as $R^1$ and $R^2$ is preferably 30 or less and more preferably 20 or less. More specifically, the number of carbon atoms in the alkyl group which may be used as $R^1$ and $R^2$ is preferably 1 to 30, more preferably 1 to 20, still more preferably 1 to 15, and still more preferably 3 to 11. By adjusting the number of carbon atoms in the alkyl group to be in the preferable range, the linearity of molecules can be improved, and the carrier mobility can be further improved during application to an organic semiconductor layer of a transistor.

The alkyl group which may be used as $R^1$ and $R^2$ may be linear, branched, or cyclic. From the viewpoint of carrier mobility, a linear alkyl group is preferable.

In a case where $R^1$ or $R^2$ represents an alkyl group having a substituent, the substituent in the alkyl group is not particularly limited, and examples thereof include: a halogen atom (for example, a fluorine atom, a chlorine atom, a bromine atom, or an iodine atom); a cycloalkyl group (a cycloalkyl group preferably having 3 to 20 carbon atoms and more preferably 4 to 15 carbon atoms; the cycloalkyl group is preferably a 5-membered ring or a 6-membered ring); an aryl group (an aryl group having preferably 6 to 20 carbon atoms, more preferably 6 to 18 carbon atoms, and still more preferably 6 to 15 carbon atoms; for example, a phenyl group, a naphthyl group, a p-pentylphenyl group, a 3,4-dipentylphenyl group, a p-heptoxyphenyl group, or a 3,4-diheptoxyphenyl group); a heterocyclic group (preferably a 3 to 8-membered ring and more preferably a 5- or 6-membered ring; it is preferable that as a ring-constituting atom, an oxygen atom, a sulfur atom, and/or a nitrogen atom is included; for example, a 2-hexylfuranyl group); a cyano group; a hydroxy group; a nitro group; an acyl group (an acyl group having preferably from 2 to 20 carbon atoms, more preferably from 2 to 15 carbon atoms, and still more preferably from 2 to 10 carbon atoms; for example, a hexanoyl group or a benzoyl group); an alkoxy group (an alkoxy group having preferably 1 to 20 carbon atoms, more preferably 1 to 15 carbon atoms, and still more preferably 1 to 10 carbon atoms; for example, a butoxy group); an aryloxy group (an aryloxy group having preferably 6 to 20 carbon atoms, more preferably 6 to 18 carbon atoms, and still more preferably 6 to 15 carbon atoms); a silyloxy group (a silyloxy group having preferably 0 to 18 carbon atoms, more preferably 0 to 15 carbon atoms, and still more preferably 0 to 12 carbon atoms); a heterocyclic oxy group (a heterocyclic oxy group including preferably 3 to 8 rings and more preferably 5 or 6 rings); an acyloxy group (an acyloxy group having preferably 2 to 20 carbon atoms, more preferably 2 to 15 carbon atoms, and still more preferably 2 to 10 carbon atoms); a carbamoyloxy group (a carbamoyloxy group having preferably 1 to 20 carbon atoms, more preferably 1 to 15 carbon atoms, and still more preferably 1 to 10 carbon atoms); an amino group (an amino group having preferably 0 to 20 carbon atoms, more preferably 0 to 15 carbon atoms, and still more preferably 0 to 10 carbon atoms and including an anilino group); an acylamino group (an acylamino group having preferably 2 to 20 carbon atoms, more preferably 2 to 15 carbon atoms, and still more preferably 2 to 10 carbon atoms); an aminocarbonylamino group (an aminocarbonylamino group having preferably 1 to 20 carbon atoms, more preferably 1 to 15 carbon atoms, and still more preferably 1 to 10 carbon atoms); an alkoxycarbonylamino group (an alkoxycarbonylamino group having preferably 2 to 20 carbon atoms, more preferably 2 to 15 carbon atoms, and still more preferably 2 to 10 carbon atoms); an aryloxycarbonylamino group (an aryloxycarbonylamino group having preferably 7 to 20 carbon atoms, more preferably 7 to 18 carbon atoms, and still more preferably 7 to 15 carbon atoms); an alkylsulfonylamino group (an alkylsulfonylamino group having preferably 1 to 20 carbon atoms, more preferably 1 to 15 carbon atoms, and still more preferably 1 to 10 carbon atoms); an arylsulfonylamino group (an arylsulfonylamino group having preferably 6 to 20 carbon atoms, more preferably 6 to 18 carbon atoms, and still more preferably 6 to 15 carbon atoms); a mercapto group; an alkylthio group (an alkylthio group having preferably 1 to 20 carbon atoms, more preferably from 1 to 15 carbon atoms, and still more preferably from 1 to 10 carbon atoms; for example, a methylthio group or an octylthio group); an arylthio group (an arylthio group having preferably 6 to 20 carbon atoms, more preferably 6 to 18 carbon atoms, and still more preferably 6 to 15 carbon atoms); a heterocyclic thio group (a heterocyclic thio group including preferably 3 to 8 rings and more preferably 5 or 6 rings); a sulfamoyl group (a sulfamoyl group having preferably 0 to 20 carbon atoms, more preferably 0 to 15 carbon atoms, and still more preferably 0 to 10 carbon atoms); a sulfo group; an alkylsulfinyl group (an alkylsulfinyl group having preferably 1 to 20 carbon atoms, more preferably 1 to 15 carbon atoms, and still more preferably 1 to 10 carbon atoms); an arylsulfinyl group (an arylsulfinyl group having preferably 6 to 20 carbon atoms, more preferably 6 to 18 carbon atoms, and still more preferably 6 to 15 carbon atoms); an alkylsulfonyl group (an alkylsulfonyl group having preferably 1 to 20 carbon atoms, more preferably 1 to 15 carbon atoms, and still more preferably 1 to 10 carbon atoms); an arylsulfonyl group (an arylsulfonyl group having preferably 6 to 20 carbon atoms, more preferably 6 to 18 carbon atoms, and still more preferably 6 to 15 carbon atoms); an alkyloxycarbonyl group (an alkyloxycarbonyl group having preferably 2 to 20 carbon atoms, more preferably 2 to 15 carbon atoms, and still more preferably 2 to 10 carbon atoms); an aryloxycarbonyl group (an aryloxycarbonyl group having preferably 7 to 20 carbon atoms, more preferably 7 to 18 carbon atoms, and still more preferably 7 to 15 carbon atoms); a carbamoyl group (a carbamoyl group having preferably 1 to 20 carbon atoms, more preferably 1 to 15 carbon atoms, and still more preferably 1 to 10 carbon atoms); an aryl azo group (an aryl azo group having preferably 6 to 20 carbon atoms, more preferably 6 to 18 carbon atoms, and still more preferably 6 to 15 carbon atoms); a heterocyclic azo group (a heterocyclic azo group including preferably 3 to 8 rings and more preferably 5 or 6 rings); a phosphino group; a phosphinyl group; a phosphinyloxy group; a phosphinylamino group; a phosphono group; a silyl group (a silyl group having preferably 0 to 18 carbon atoms, more preferably 0 to 15 carbon atoms, and still more preferably 0 to 12 carbon atoms; for example, a di-trimethylsiloxy methyl butoxy group); a hydrazino group; a ureido group; a boronic acid group ($-B(OH)_2$); a phosphate group ($-OPO(OH)_2$); a sulfate group ($-OSO_3H$); and other well-known substituents. In addition, in a case where the alkyl group which may be used as $R^1$ and $R^2$ is a cycloalkyl group, this cycloalkyl group may include, as a substituent, an alkyl group, an alkenyl group, or an alkynyl group which may be included in the aryl group used as $R^1$ and $R^2$.

In particular, it is preferable that $R^1$ or $R^2$ represents an unsubstituted alkyl group.

The number of carbon atoms in the alkenyl group which may be used as $R^1$ and $R^2$ is preferably 30 or less and more preferably 20 or less. More specifically, the number of carbon atoms in the alkenyl group which may be used as $R^1$ and $R^2$ is preferably 2 to 30, more preferably 2 to 20, still more preferably 2 to 15, still more preferably 2 to 10, and still more preferably 2 to 4.

A substituent which may be included in the alkenyl group is not particularly limited. For example, the alkenyl group which may be used as $R^1$ and $R^2$ may have the substituent which may be included in the alkyl group used as $R^1$ and $R^2$.

The number of carbon atoms in the alkynyl group which may be used as $R^1$ and $R^2$ is preferably 30 or less and more preferably 20 or less. More specifically, the number of carbon atoms in the alkenyl group which may be used as $R^1$ and $R^2$ is preferably 2 to 30, more preferably 2 to 20, still more preferably 2 to 15, still more preferably 2 to 10, still more preferably 2 to 4, and still more preferably 2.

A substituent which may be included in the alkynyl group is not particularly limited. For example, the alkynyl group which may be used as $R^1$ and $R^2$ may have the substituent which may be included in the alkyl group used as $R^1$ and $R^2$. In particular, as the substituent which may be included in the alkynyl group, a group selected from a silyl group or an aryl group is preferable, a group selected from a trialkylsilyl group or a phenyl group is more preferable, and a trialkylsilyl group is still more preferable.

The number of carbon atoms in the aryl group which may be used as $R^1$ and $R^2$ is preferably 30 or less and more preferably 20 or less. More specifically, the number of carbon atoms in the aryl group which may be used as $R^1$ and $R^2$ is preferably 6 to 30, more preferably 6 to 20, still more preferably 6 to 18, and still more preferably 6 to 12.

A substituent which may be included in the aryl group is not particularly limited. For example, the aryl group which may be used as $R^1$ and $R^2$ may have the substituent which may be included in the alkyl group used as $R^1$ and $R^2$. In addition, the substituent which may be included in the aryl group used as $R^1$ and $R^2$ is preferably an alkyl group (a linear, branched, or cyclic alkyl group having preferably 1 to 20 carbon atoms, more preferably 1 to 15 carbon atoms, and still more preferably 1 to 10 carbon atoms), and may be an alkenyl group (a linear or branched alkenyl group having preferably 2 to 20 carbon atoms, more preferably 2 to 15 carbon atoms, and still more preferably 2 to 10 carbon atoms) or an alkynyl group (a linear or branched alkynyl group having preferably 2 to 20 carbon atoms, more preferably 2 to 15 carbon atoms, and still more preferably 2 to 10 carbon atoms).

In a case where the aryl group which may be used as $R^1$ and $R^2$ has a substituent, the number of substituents in the aryl group is preferably 1 to 3, more preferably 1 or 2, and still more preferably 1.

The number of carbon atoms in the heteroaryl group which may be used as $R^1$ and $R^2$ is preferably 30 or less and more preferably 20 or less. More specifically, the number of carbon atoms in the heteroaryl group which may be used as $R^1$ and $R^2$ is preferably 3 to 30, more preferably 4 to 20, still more preferably 4 to 10, and still more preferably 4. As a ring-constituting heteroatom in the heteroaryl group, a ring at least one kind of atoms selected from the group consisting of a sulfur atom, a nitrogen atom, a selenium atom, an oxygen atom, and a tellurium atom is preferable. In addition, this heteroaryl group is preferably a 3- to 8-membered ring and more preferably 5- or 6-membered ring.

Specific preferable examples of the heteroaryl group which may be used as $R^1$ and $R^2$ include a furanyl group, a pyrrolyl group, a pyrazolyl group, an imidazolyl group, a thienyl group, a thiazolyl group, a thienothienyl group, a benzothienyl group, a thienophenyl group, a pyridyl group, a pyrimidinyl group, a pyridazinyl group, and a pyrazinyl group. In particular, a thienyl group or a furyl group is more preferable, and a thienyl group is still more preferable.

A substituent which may be included in the heteroaryl group is not particularly limited. For example, the heteroaryl group may have the substituent which may be included in the aryl group used as $R^1$ and $R^2$. In a case where the heteroaryl group which may be used as $R^1$ and $R^2$ has a substituent, it is preferable that this substituent is an alkyl group.

From the viewpoint of further improving carrier mobility during application to an organic semiconductor layer of a transistor, it is preferable that the structure of $R^1$ and $R^2$ has an aliphatic hydrocarbon group. In particular, it is preferable that $R^1$ and $R^2$ each independently represent an aryl group or a heteroaryl group and the aryl group or the heteroaryl group has an aliphatic hydrocarbon group as a substituent.

In the present invention, "aliphatic hydrocarbon group" refers to a linear, branched, or cyclic nonaromatic hydrocarbon group, and examples thereof include an alkyl group, an alkenyl group, and an alkynyl group. Among these, an alkyl group is preferable.

In Formula (1), $R^1$ and $R^2$ in Formula (1) are bonded to a ring-constituting atom of the 5-membered ring including Y and Z directly or indirectly through a divalent group A. That is, the configuration of Formula (1) defined in the present invention also includes a configuration in which $R^1$ and/or $R^2$ is bonded to a ring-constituting atom of the 5-membered ring including Y and Z through the divalent group A. The divalent group A is a group selected from —O—, —S—, —NR$^8$—, —CO—, —SO—, or —SO$_2$— or is a group in which two or more selected from —O—, —S—, —NR$^8$—, —CO—, —SO—, and —SO$_2$— are linked to each other. In a case where the divalent group A is a group in which two or more selected from —O—, —S—, —NR$^8$—, —CO—, —SO—, or —SO$_2$— are linked to each other, the number of the two or more groups linked to each other is preferably 2 to 4 and more preferably 2 or 3.

In particular, the divalent group A is preferably a group selected from —O—, —S—, —NR$^8$—, —CO—, —SO—, or —SO$_2$—, more preferably —O—, —S—, or —CO—, and still more preferably —O—.

It is preferable that $R^1$ and $R^2$ have the same structure in a case where the divalent group A is also taken into consideration.

In Formula (1), $R^3$ and $R^4$ each independently represent a halogen atom, an alkyl group, an alkenyl group, an alkynyl group, an aryl group, or a heteroaryl group. The halogen atom which may be used as $R^3$ and $R^4$ is preferably a fluorine atom, a chlorine atom, a bromine atom, or an iodine atom and more preferably a fluorine atom or a chlorine atom.

The alkyl group, the alkenyl group, the alkynyl group, the aryl group, and the heteroaryl group which may be used as $R^3$ and $R^4$ have the same preferable configurations as the alkyl group, the alkenyl group, the alkynyl group, the aryl group, and the heteroaryl group which may be used as $R^1$. Among these configurations, a configuration in which the alkyl group, the alkenyl group, the alkynyl group, the aryl group, and the heteroaryl group which may be used as $R^3$ and $R^4$ have a halogen atom as a substituent is also preferable.

In addition, $R^3$ and $R^4$ are bonded to a ring-constituting atom of a benzene ring in Formula (1) directly or indirectly through the divalent group A, That is, the configuration of Formula (1) defined in the present invention also includes a configuration in which $R^3$ and/or $R^4$ is bonded to a ring-constituting atom of the benzene ring through the divalent group A.

It is preferable that $R^3$ and $R^4$ have the same structure in a case where the divalent group A is also taken into consideration.

m and n representing the numbers of $R^3$ and $R^4$ each independently represent an integer of 0 to 2. m and n each independently represent preferably 0 or 1 and more preferably 0. It is preferable that m and n have the same value.

In Formula (1), $R^5$ in NR$^5$ which may be used as X, $R^6$ in CR$^6$ and $R^7$ in NR$^7$ which may be used as Y and Z, and $R^8$ in NR$^8$ which may be used as the divalent group A each independently represent a hydrogen atom, an alkyl group, an alkenyl group, an alkynyl group, an aryl group, or a heteroaryl group. Examples of preferable configurations of the alkyl group, the alkenyl group, the alkynyl group, the aryl group, and the heteroaryl group which may be used as $R^5$, $R^6$, $R^7$, and $R^8$ include the preferable configurations of the alkyl group, the alkenyl group, the alkynyl group, the aryl group, and the heteroaryl group which may be used as $R^1$.

In particular, $R^5$ represents preferably an alkyl group having 1 to 11 carbon atoms and more preferably an alkyl group having 1 to 5 carbon atoms. In addition, $R^6$ represents preferably a hydrogen atom or an alkyl group and more preferably a hydrogen atom. In addition, $R^7$ represents preferably an alkyl group or an aryl group and more preferably an alkyl group. In addition, $R^8$ represents preferably an alkyl group or an aryl group.

From the viewpoint of improving molecular symmetry to further improve carrier mobility, in Formula (1), it is preferable that $R^1$ and $R^2$ are the same, $R^3$ and $R^4$ are the same, and m and n are the same.

In the present invention, the compound represented by Formula (1) does not include a configuration in which X represents an oxygen atom or a sulfur atom and the 5-membered ring including Y and Z is an imidazole ring (including a configuration in which a ring-constituting atom of the imidazole ring has a substituent). In addition, in the present invention, the compound represented by Formula (1) does not also include a configuration in which X represents a sulfur atom, Y represents CH, Z represents a sulfur atom, both $R^1$ and $R^2$ represent a hydrogen atom, and both m and n represent 0. Even in a case where a compound excluded from Formula (1) is applied to the organic semiconductor layer of the transistor, it is difficult to obtain a desired carrier mobility, a variation in performance between elements is likely to occur, and a desired effect is not likely to be obtained.

Even regarding the compound according to the configuration excluded from Formula (1), in a case where a microcrystalline organic semiconductor film is formed using the compound according to the configuration excluded from Formula (1) and is used as an organic semiconductor layer of an organic semiconductor transistor, a variation between elements or the like is more suppressed as compared to a case where an organic semiconductor film having a large crystal domain size is formed using the compound and is used as an organic semiconductor layer of an organic semiconductor transistor.

A compound that has a mother nucleus (fused polycyclic structure) represented by Formula (1) defined by the present invention tends to exhibit high crystallinity irrespective of a structure (a structure of a substituent) other than the mother nucleus, and a film having a large crystal domain size is formed through film formation using a typical solution process. In a transistor that includes an organic semiconductor layer formed of the film, a variation in performance between elements tends to be large. On the other hand, by forming a film by vapor deposition or the like to reduce the crystal domain size, a variation in performance between elements can be further suppressed and power consumption can be further suppressed irrespective of the structure of the substituent in the compound represented by Formula (1).

It is preferable that the compound represented by Formula (1) that has a molecular weight of 3000 or lower is a compound represented by the following Formula (2) or (3).

Formula (2)

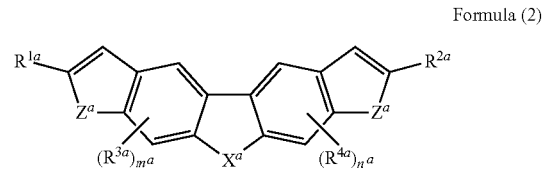

Formula (3)

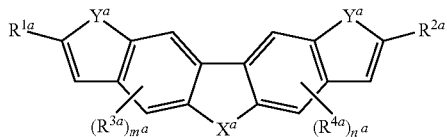

In Formulae (2) and (3), $X^a$ represents an oxygen atom, a sulfur atom, or a selenium atom.

$Y^a$ and $Z^a$ each independently represent an oxygen atom, a sulfur atom, a selenium atom, or $NR^{7a}$. $R^{7a}$ has the same definition as $R^7$ in Formula (1).

$R^{1a}$, $R^{2a}$, $R^{3a}$, $R^{4a}$, $m^a$, and $n^a$ have the same definitions and the same preferable configurations as $R^1$, $R^2$, $R^3$, $R^4$, m, and n in Formula (1), respectively.

In addition, binding forms of $R^{1a}$, $R^{2a}$, $R^{3a}$, and $R^{4a}$ to a ring-constituting atom are also the same as binding forms of $R^1$, $R^2$, $R^3$, and $R^4$ in Formula (1) to a ring-constituting atom, and preferable binding forms thereof are also the same. That is, $R^{1a}$, $R^{2a}$, $R^{3a}$, and $R^{4a}$ may be bonded to a ring-constituting atom directly or indirectly through the divalent group A. In the present invention, the configuration in which $R^{1a}$, $R^{2a}$, $R^{3a}$, and $R^{4a}$ is bonded to a ring-constituting atom through the divalent group A is also included in the structure of Formula (2) or (3).

In this case, a configuration in which $X^a$ represents a sulfur atom, $Z^a$ represents a sulfur atom, both $R^{1a}$ and $R^{2a}$ represent a hydrogen atom, and both $m^a$ and $n^a$ represent 0 is excluded from the compound represented by Formula (2).

In addition, it is more preferable that the compound represented by the formula (2) that has a molecular weight of 3000 or lower is represented by the following Formula (4). In addition, it is more preferable that the compound represented by the formula (3) that has a molecular weight of 3000 or lower is represented by the following Formula (5).

Formula (4)

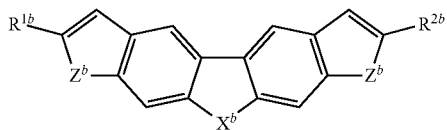

Formula (5)

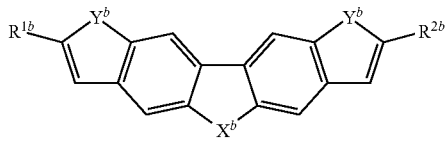

In Formulae (4) and (5), $X^b$, $Y^b$, and $Z^b$ represent an oxygen atom, a sulfur atom, or a selenium atom.

$R^{1b}$ and $R^{2b}$ have the same definitions and the same preferable configurations as $R^{1a}$ and $R^{2a}$ in Formula (2), respectively. Binding forms of $R^{1b}$ and $R^{2b}$ to a ring-constituting atom are also the same as binding forms of $R^{1a}$ and $R^{2a}$ in Formula (2) to a ring-constituting atom, respectively, and preferable binding forms thereof are also the same. That is, $R^{1b}$ and $R^{2b}$ may be bonded to a ring-constituting atom directly or indirectly through the divalent group A. In the present invention, the configuration in which $R^{1b}$ and/or $R^{2b}$ is bonded to a ring-constituting atom through the divalent group A is also included in the structure of Formula (4) or (5).

A configuration in which $X^b$ represents a sulfur atom, $Z^b$ represents a sulfur atom, and both $R^{1b}$ and $R^{2b}$ represent a hydrogen atom is excluded from the compound represented by Formula (4).

In Formulae (4) and (5), it is preferable that $R^{1b}$ and $R^{2b}$ have an aliphatic hydrocarbon group. It is preferable that the aliphatic hydrocarbon group is a linear aliphatic hydrocarbon group. It is preferable that $R^{1b}$ and $R^{2b}$ represent an aryl group having a linear aliphatic hydrocarbon group or a heteroaryl group having a linear aliphatic hydrocarbon group.

The compound represented by Formula (1) that has a molecular weight of 3000 or lower can be synthesized using a typical method. The synthesis of the compound can be found in, for example, Examples of JP2015-195362A.

Specific examples of the compound represented by Formula (1) that has a molecular weight of 3000 or lower will be shown below and in Examples, but the present invention is not limited thereto.

Examples of the compound represented by Formula (1) that has a molecular weight of 3000 or lower include specific examples 1 to 458 shown in paragraphs "0053" to "0075" and specific examples 535 to 686 shown in paragraphs "0079" to "0087" of JP2015-195362A.

In addition, examples shown in tables below as the compound represented by Formula (1) that has a molecular weight of 3000 or lower can also be used. In the tables below, in a case where $R^1$ and $R^2$ are bonded to a ring-constituting atom through the divalent group A, the columns of $R^1$ and $R^2$ show structures including the divalent group A. In tables below, iPr represents isopropyl, and Bu represents butyl.

TABLE 1

| Specific Example | X | Y | Z | m | n | $R^1$ | $R^2$ | $R^3$ | $R^4$ |
|---|---|---|---|---|---|---|---|---|---|
| 1 | O | CH | Se | 0 | 0 | $CH_3$ | $CH_3$ | — | — |
| 2 | O | CH | Se | 0 | 0 | $n\text{-}C_{14}H_{29}$ | $n\text{-}C_{14}H_{29}$ | — | — |

TABLE 1-continued

| Specific Example | X | Y | Z | m | n | R¹ | R² | R³ | R⁴ |
|---|---|---|---|---|---|---|---|---|---|
| 3 | O | CH | Se | 0 | 0 | phenyl | phenyl | — | — |
| 4 | O | CH | Se | 0 | 0 | 2-iPr-thiophen-5-yl | 2-iPr-thiophen-5-yl | — | — |
| 5 | O | CH | Se | 1 | 1 | $CH_3$ | $CH_3$ | $CH_3$ | $CH_3$ |
| 6 | O | $C(n\text{-}C_8H_{17})$ | Se | 0 | 0 | H | H | — | — |
| 7 | O | $C(n\text{-}C_6H_{13})$ | Se | 0 | 0 | $CH_3$ | $CH_3$ | — | — |
| 8 | O | CH | Se | 1 | 1 | $C(=O)\text{-}nC_6C_{13}$ | $N(C_4H_9)_2$ | $OCH_3$ | $OCH_3$ |
| 9 | O | CH | Se | 0 | 0 | phenyl | $n\text{-}C_5H_{11}$ | — | — |
| 10 | O | CH | Se | 2 | 2 | $CH_3$ | $CH_3$ | $CH_3$ | $CH_3$ |

TABLE 2

| Specific Example | X | Y | Z | m | n | R¹ | R² | R³ | R⁴ |
|---|---|---|---|---|---|---|---|---|---|
| 11 | O | O | N | 0 | 0 | $CH_3$ | $CH_3$ | — | — |
| 12 | O | O | N | 0 | 0 | $n\text{-}C_{14}H_{29}$ | $n\text{-}C_{14}H_{29}$ | — | — |
| 13 | O | O | N | 0 | 0 | phenyl | phenyl | — | — |
| 14 | O | O | N | 0 | 0 | 4-tBu-phenyl | 4-tBu-phenyl | — | — |
| 15 | O | O | N | 1 | 1 | $CH_3$ | $CH_3$ | $CH_3$ | $CH_3$ |
| 16 | O | O | N | 0 | 0 | $S(=O)_2\text{-}nC_6C_{13}$ | $S(=O)_2\text{-}nC_6C_{13}$ | — | — |
| 17 | O | O | N | 0 | 0 | $CH_3$ | $CH_3$ | — | — |
| 18 | O | O | N | 1 | 1 | $C(=O)\text{-}nC_6H_{13}$ | $C\equiv C\text{-}nC_7H_{15}$ | $SCH_3$ | $SCH_3$ |

TABLE 2-continued

| Specific Example | X | Y | Z | m | n | R¹ | R² | R³ | R⁴ |
|---|---|---|---|---|---|---|---|---|---|
| 19 | O | O | N | 0 | 0 | 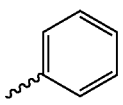 | n-C$_5$H$_{11}$ | — | — |
| 20 | O | O | N | 2 | 2 | CH$_3$ | CH$_3$ | CH$_3$ | CH$_3$ |

TABLE 3

| Specific Example | X | Y | Z | m | n | R¹ | R² | R³ | R⁴ |
|---|---|---|---|---|---|---|---|---|---|
| 21 | O | S | N | 0 | 0 | CH$_3$ | CH$_3$ | — | — |
| 22 | O | S | N | 0 | 0 | n-C$_{14}$H$_{29}$ | n-C$_{14}$H$_{29}$ | — | — |
| 23 | O | S | N | 0 | 0 |  |  | — | — |
| 24 | O | S | N | 0 | 0 | 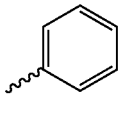 (4-tBu-phenyl) | 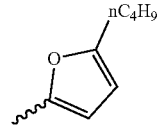 (4-tBu-phenyl) | — | — |
| 25 | O | S | N | 1 | 1 | CH$_3$ | CH$_3$ | CH$_3$ | CH$_3$ |
| 26 | O | S | N | 0 | 0 | —S—nC$_6$H$_{13}$ | —S—nC$_6$H$_{13}$ | — | — |
| 27 | O | S | N | 0 | 0 | CH$_3$ | CH$_3$ | — | — |
| 28 | O | S | N | 1 | 1 | —OCH(nC$_6$H$_{13}$)$_2$ branch | —OCH(nC$_6$H$_{13}$)$_2$ branch | SCH$_3$ | SCH$_3$ |
| 29 | O | S | N | 0 | 0 | —CH(nC$_6$H$_{13}$)$_2$ | n-C$_5$H$_{11}$ | — | — |
| 30 | O | S | N | 2 | 2 | CH$_3$ | CH$_3$ | CH$_3$ | CH$_3$ |

TABLE 4

| Specific Example | X | Y | Z | m | n | R¹ | R² | R³ | R⁴ |
|---|---|---|---|---|---|---|---|---|---|
| 31 | O | Se | CH | 0 | 0 | CH$_3$ | CH$_3$ | — | — |
| 32 | O | Se | CH | 0 | 0 | n-C$_{14}$H$_{29}$ | n-C$_{14}$H$_{29}$ | — | — |
| 33 | O | Se | CH | 0 | 0 |  | 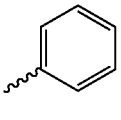 | — | — |

TABLE 4-continued

| Specific Example | X | Y | Z | m | n | R¹ | R² | R³ | R⁴ |
|---|---|---|---|---|---|---|---|---|---|
| 34 | O | Se | CH | 0 | 0 | 2-iPr-thiophen-5-yl | 4-tBu-phenyl | — | — |
| 35 | O | Se | CH | 1 | 1 | H | H | n-C$_{14}$H$_{29}$ | n-C$_{14}$H$_{29}$ |
| 36 | O | Se | C(n-C$_9$H$_{19}$) | 0 | 0 | SO$_2$-nC$_6$H$_{13}$ | SO$_2$-nC$_6$H$_{13}$ | — | — |
| 37 | O | Se | C(n-C$_6$H$_{13}$) | 0 | 0 | CH$_3$ | CH$_3$ | — | — |
| 38 | O | Se | CH | 1 | 1 | C(O)-nC$_6$H$_{13}$ | N(C$_4$H$_9$)$_2$ | OCH$_3$ | OCH$_3$ |
| 39 | O | Se | CH | 0 | 0 | phenyl | n-C$_5$H$_{11}$ | — | — |
| 40 | O | Se | CH | 2 | 2 | CH$_3$ | CH$_3$ | CH$_3$ | CH$_3$ |

TABLE 5

| Specific Example | X | Y | Z | m | n | R¹ | R² | R³ | R⁴ |
|---|---|---|---|---|---|---|---|---|---|
| 41 | O | Se | N | 0 | 0 | CH$_3$ | CH$_3$ | — | — |
| 42 | O | Se | N | 0 | 0 | n-C$_{14}$H$_{29}$ | n-C$_{14}$H$_{29}$ | — | — |
| 43 | O | Se | N | 0 | 0 | phenyl | phenyl | — | — |
| 44 | O | Se | N | 0 | 0 | 4-tBu-phenyl | 4-tBu-phenyl | — | — |
| 45 | O | Se | N | 1 | 1 | CH$_3$ | CH$_3$ | CH$_3$ | CH$_3$ |
| 46 | O | Se | N | 0 | 0 | CH=CH-C$_3$H$_7$ | CH=CH-C$_3$H$_7$ | — | — |
| 47 | O | Se | N | 0 | 0 | CH$_3$ | CH$_3$ | — | — |
| 48 | O | Se | N | 1 | 1 | S(O)-nC$_6$H$_{13}$ | C≡C-nC$_7$H$_{15}$ | SCH$_3$ | SCH$_3$ |
| 49 | O | Se | N | 0 | 0 | phenyl | n-C$_5$H$_{11}$ | — | — |
| 50 | O | Se | N | 2 | 2 | CH$_3$ | CH$_3$ | CH$_3$ | CH$_3$ |

TABLE 6

| Specific Example | X | Y | Z | m | n | R¹ | R² | R³ | R⁴ |
|---|---|---|---|---|---|---|---|---|---|
| 51 | O | CH | S | 0 | 0 | CH₃ | CH₃ | — | — |
| 52 | O | CH | S | 0 | 0 | n-C₁₄H₂₉ | n-C₁₄H₂₉ | — | — |
| 53 | O | CH | S | 0 | 0 | phenyl | phenyl | — | — |
| 54 | O | CH | S | 0 | 0 | 1-methyl-2-iPr-pyrrol-5-yl | 4-tBu-phenyl | — | — |
| 55 | O | CH | S | 1 | 1 | H | H | n-C₁₄H₂₉ | n-C₁₄H₂₉ |
| 56 | O | C(n-C₉H₁₉) | S | 0 | 0 | SO₂-nC₆H₁₃ | SO₂-nC₆H₁₃ | — | — |
| 57 | O | C(n-C₆H₁₃) | N(CH₃) | 0 | 0 | CH₃ | CH₃ | — | — |
| 58 | O | CH | N(CH₃) | 1 | 1 | C(O)-nC₆H₁₃ | N(C₄H₉)₂ | OCH₃ | OCH₃ |
| 59 | O | CH | C(n-C₉H₁₉) | 0 | 0 | phenyl | n-C₅H₁₁ | — | — |
| 60 | O | CH | C(n-C₉H₁₉) | 2 | 2 | CH₃ | CH₃ | CH₃ | CH₃ |

TABLE 7

| Specific Example | X | Y | Z | m | n | R¹ | R² | R³ | R⁴ |
|---|---|---|---|---|---|---|---|---|---|
| 61 | O | O | CH | 0 | 0 | CH₃ | CH₃ | — | — |
| 62 | O | O | C(n-C₉H₁₉) | 0 | 0 | n-C₁₄H₂₉ | n-C₁₄H₂₉ | — | — |
| 63 | O | O | C(n-C₆H₁₃) | 0 | 0 | cyclohexyl | cyclohexyl | — | — |
| 64 | O | O | CH | 0 | 0 | 4-amyl-phenyl | 4-amyl-phenyl | — | — |
| 65 | O | O | CH | 1 | 1 | CH₃ | CH₃ | CH₃ | CH₃ |
| 66 | O | O | C(n-C₉H₁₉) | 0 | 0 | CH=CH-C₃H₇ | CH=CH-C₃H₇ | — | — |
| 67 | O | S | C(n-C₆H₁₃) | 0 | 0 | CH₃ | CH₃ | — | — |

TABLE 7-continued

| Specific Example | X | Y | Z | m | n | R$^1$ | R$^2$ | R$^3$ | R$^4$ |
|---|---|---|---|---|---|---|---|---|---|
| 68 | O | S | CH | 1 | 1 | -S(=O)-nC$_6$H$_{13}$ | -≡-nC$_7$H$_{15}$ | SCH$_3$ | SCH$_3$ |
| 69 | O | S | CH | 0 | 0 | phenyl | n-C$_5$H$_{11}$ | — | — |
| 70 | O | S | CH | 2 | 2 | CH$_3$ | CH$_3$ | CH$_3$ | CH$_3$ |

TABLE 8

| Specific Example | X | Y | Z | m | n | R$^1$ | R$^2$ | R$^3$ | R$^4$ |
|---|---|---|---|---|---|---|---|---|---|
| 71 | O | N | O | 0 | 0 | CH$_3$ | CH$_3$ | — | — |
| 72 | O | N | O | 0 | 0 | n-C$_{14}$H$_{29}$ | n-C$_{14}$H$_{29}$ | — | — |
| 73 | O | N | O | 0 | 0 | 2-fluoropyridin-5-yl | 2-fluoropyridin-5-yl | — | — |
| 74 | O | N | O | 0 | 0 | 4-CF$_3$-phenyl | 4-CF$_3$-phenyl | — | — |
| 75 | O | N | O | 1 | 1 | CH$_3$ | CH$_3$ | CH$_3$ | CH$_3$ |
| 76 | O | N | O | 0 | 0 | -S(=O)-nC$_6$H$_{13}$ | -S(=O)$_2$-phenyl | — | — |
| 77 | O | N | O | 0 | 0 | CH$_3$ | CH$_3$ | — | — |
| 78 | O | N | O | 1 | 1 | -C(=O)-nC$_6$H$_{13}$ | -≡-nC$_7$H$_{15}$ | SCH$_3$ | SCH$_3$ |
| 79 | O | N | O | 0 | 0 | biphenyl | n-C$_5$H$_{11}$ | — | — |
| 80 | O | N | O | 2 | 2 | CH$_3$ | CH$_3$ | CH$_3$ | CH$_3$ |

TABLE 9

| Specific Example | X | Y | Z | m | n | R$^1$ | R$^2$ | R$^3$ | R$^4$ |
|---|---|---|---|---|---|---|---|---|---|
| 81 | O | N | S | 0 | 0 | CH$_3$ | CH$_3$ | — | — |
| 82 | O | N | S | 0 | 0 | n-C$_9$H$_9$ | n-C$_9$H$_9$ | — | — |

TABLE 9-continued

| Specific Example | X | Y | Z | m | n | R¹ | R² | R³ | R⁴ |
|---|---|---|---|---|---|---|---|---|---|
| 83 | O | N | S | 0 | 0 | 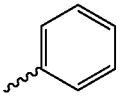 | 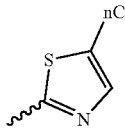 nC$_4$H$_9$ | — | — |
| 84 | O | N | S | 0 | 0 | 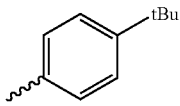 tBu | 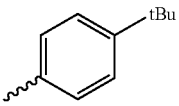 tBu | — | — |
| 85 | O | N | S | 1 | 1 |  CH$_3$ |  CH$_3$ |  CH$_3$ |  CH$_3$ |
| 86 | O | N | S | 0 | 0 | 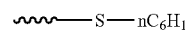—S—nC$_6$H$_{13}$ | 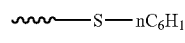—S—nC$_6$H$_{13}$ | — | — |
| 87 | O | N | S | 0 | 0 |  CH$_3$ |  CH$_3$ | — | — |
| 88 | O | N | S | 1 | 2 | 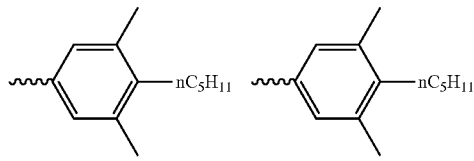 nC$_5$H$_{11}$ | 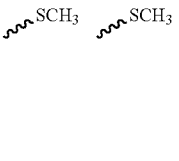 nC$_5$H$_{11}$ |  SCH$_3$ |  SCH$_3$ |
| 89 | O | N | S | 0 | 0 | 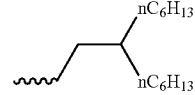 nC$_6$H$_{13}$ / nC$_6$H$_{13}$ |  n-C$_5$H$_{11}$ | — | — |
| 90 | O | N | S | 0 | 0 |  CH$_3$ |  CH$_3$ | — | — |

TABLE 10

| Specific Example | X | Y | Z | m | n | R¹ | R² | R³ | R⁴ |
|---|---|---|---|---|---|---|---|---|---|
| 91 | O | N | Se | 0 | 0 | 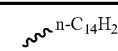 n-C$_{14}$H$_{29}$ | 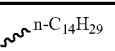 n-C$_{14}$H$_{29}$ | — | — |
| 92 | O | N | Se | 0 | 0 | 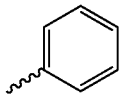 | 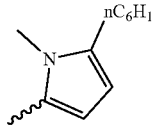 nC$_6$H$_{13}$ | — | — |
| 93 | O | N | Se | 0 | 0 | 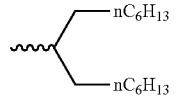 nC$_6$H$_{13}$ / nC$_6$H$_{13}$ | 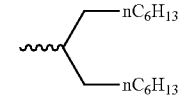 nC$_6$H$_{13}$ / nC$_6$H$_{13}$ | — | — |
| 94 | O | N | Se | 1 | 1 |  H |  H | 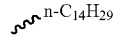 n-C$_{14}$H$_{29}$ | 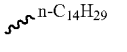 n-C$_{14}$H$_{29}$ |
| 95 | O | N | Se | 0 | 0 | 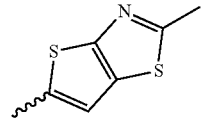 | 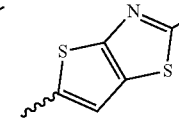 | — | — |
| 96 | O | N | Se | 0 | 0 |  CH$_3$ |  CH$_3$ | — | — |
| 97 | O | N | Se | 1 | 1 | 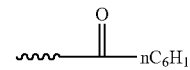 | 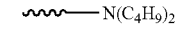—N(C$_4$H$_9$)$_2$ | 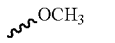 OCH$_3$ | 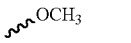 OCH$_3$ |

TABLE 10-continued

| Specific Example | X | Y | Z | m | n | R¹ | R² | R³ | R⁴ |
|---|---|---|---|---|---|---|---|---|---|
| 98 | O | N | Se | 0 | 0 | phenyl | n-$C_5H_{11}$ | — | — |
| 99 | O | N($CH_3$) | CH | 0 | 0 | $CH_3$ | $CH_3$ | — | — |
| 100 | O | NH | CH | 0 | 0 | n-$C_{14}H_{29}$ | n-$C_{14}H_{29}$ | — | — |

TABLE 11

| Specific Example | X | Y | Z | m | n | R¹ | R² | R³ | R⁴ |
|---|---|---|---|---|---|---|---|---|---|
| 101 | O | N($CH_3$) | CH | 0 | 0 | phenyl | phenyl | — | — |
| 102 | O | N($CH_3$) | CH | 0 | 0 | =C($C_3H_7$)($C_3H_7$) | 4-tBu-phenyl | — | — |
| 103 | O | N($CH_3$) | CH | 1 | 1 | H | H | n-$C_{14}H_{29}$ | n-$C_{14}H_{29}$ |
| 104 | O | N($CH_3$) | C(n-$C_9H_{19}$) | 0 | 0 | —O—n$C_6H_{13}$ | —O—n$C_6H_{13}$ | — | — |
| 105 | O | N(n-$C_9H_{19}$) | C(n-$C_6H_{13}$) | 0 | 0 | $CH_3$ | $CH_3$ | — | — |
| 106 | O | N($CH_3$) | CH | 1 | 1 | —C(=O)—n$C_6H_{13}$ | —N($C_4H_9$)$_2$ | $OCH_3$ | $OCH_3$ |
| 107 | O | N(i-Pr) | CH | 0 | 0 | phenyl | n-$C_5H_{11}$ | — | — |
| 108 | O | N($CH_3$) | CH | 2 | 2 | $CH_3$ | $CH_3$ | $CH_3$ | $CH_3$ |
| 109 | S | CH | Se | 0 | 0 | $CH_3$ | $CH_3$ | — | — |
| 110 | S | CH | Se | 0 | 0 | n-$C_{14}H_{29}$ | n-$C_{14}H_{29}$ | — | — |

TABLE 12

| Specific Example | X | Y | Z | m | n | R¹ | R² | R³ | R⁴ |
|---|---|---|---|---|---|---|---|---|---|
| 111 | S | CH | Se | 0 | 0 | phenyl | phenyl | — | — |
| 112 | S | CH | Se | 0 | 0 | 5-iPr-thien-2-yl | 5-iPr-thien-2-yl | — | — |
| 113 | S | CH | Se | 1 | 1 | $CH_3$ | $CH_3$ | $CH_3$ | $CH_3$ |
| 114 | S | C(n-$C_8H_{17}$) | Se | 0 | 0 | H | H | — | — |

TABLE 12-continued

| Specific Example | X | Y | Z | m | n | R¹ | R² | R³ | R⁴ |
|---|---|---|---|---|---|---|---|---|---|
| 115 | S | C(n-C$_6$H$_{13}$) | Se | 0 | 0 | CH$_3$ | CH$_3$ | — | — |
| 116 | S | CH | Se | 1 | 1 | C(O)nC$_6$H$_{13}$ | —N(C$_4$H$_9$)$_2$ | OCH$_3$ | OCH$_3$ |
| 117 | S | CH | Se | 0 | 0 | phenyl | n-C$_5$H$_{11}$ | — | — |
| 118 | S | CH | N(CH$_3$) | 2 | 2 | CH$_3$ | CH$_3$ | CH$_3$ | CH$_3$ |
| 119 | S | O | N | 0 | 0 | CH$_3$ | CH$_3$ | — | — |
| 120 | S | O | N | 0 | 0 | n-C$_{14}$H$_{29}$ | n-C$_{14}$H$_{29}$ | — | — |

TABLE 13

| Specific Example | X | Y | Z | m | n | R¹ | R² | R³ | R⁴ |
|---|---|---|---|---|---|---|---|---|---|
| 121 | S | O | N | 0 | 0 | phenyl | phenyl | — | — |
| 122 | S | O | N | 0 | 0 | 4-tBu-phenyl | 4-tBu-phenyl | — | — |
| 123 | S | O | N | 1 | 1 | CH$_3$ | CH$_3$ | CH$_3$ | CH$_3$ |
| 124 | S | O | N | 0 | 0 | —S(O)$_2$—nC$_6$H$_{13}$ | —S(O)$_2$—nC$_6$H$_{13}$ | — | — |
| 125 | S | O | N | 0 | 0 | CH$_3$ | CH$_3$ | — | — |
| 126 | S | O | N | 1 | 1 | C(O)nC$_6$H$_{13}$ | ≡—nC$_7$H$_{15}$ | SCH$_3$ | SCH$_3$ |
| 127 | S | O | N | 0 | 0 | phenyl | n-C$_5$H$_{11}$ | — | — |
| 128 | S | O | N | 2 | 2 | CH$_3$ | CH$_3$ | CH$_3$ | CH$_3$ |
| 129 | S | S | N | 0 | 0 | CH$_3$ | CH$_3$ | — | — |
| 130 | S | S | N | 0 | 0 | n-C$_9$H$_{19}$ | n-C$_9$H$_{19}$ | — | — |

TABLE 14

| Specific Example | X | Y | Z | m | n | R¹ | R² | R³ | R⁴ |
|---|---|---|---|---|---|---|---|---|---|
| 131 | S | S | N | 0 | 0 |  |  nC₄H₉ | — | — |
| 132 | S | S | N | 0 | 0 | 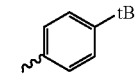 tBu | 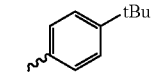 tBu | — | — |
| 133 | S | S | N | 1 | 1 | ⌇CH₃ | ⌇CH₃ | ⌇CH₃ | ⌇CH₃ |
| 134 | S | S | N | 0 | 0 | ⌇—S—nC₆H₁₃ | ⌇—S—nC₆H₁₃ | — | — |
| 135 | S | S | N | 0 | 0 | ⌇CH₃ | ⌇CH₃ | — | — |
| 136 | S | S | N | 1 | 1 |  |  | ⌇SCH₃ | ⌇SCH₃ |
| 137 | S | S | N | 0 | 0 |  nC₆H₁₃ / nC₆H₁₃ | ⌇n-C₅H₁₁ | — | — |
| 138 | S | S | N | 2 | 2 | ⌇CH₃ | ⌇CH₃ | ⌇CH₃ | ⌇CH₃ |
| 139 | S | Se | CH | 0 | 0 | ⌇CH₃ | ⌇CH₃ | — | — |
| 140 | S | Se | CH | 0 | 0 | ⌇n-C₁₄H₂₉ | ⌇n-C₁₄H₂₉ | — | — |

TABLE 15

| Specific Example | X | Y | Z | m | n | R¹ | R² | R³ | R⁴ |
|---|---|---|---|---|---|---|---|---|---|
| 141 | S | Se | CH | 0 | 0 |  | 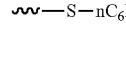 | — | — |
| 142 | S | Se | CH | 0 | 0 | 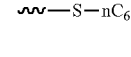 iPr |  tBu | — | — |
| 143 | S | Se | CH | 1 | 1 | ⌇H | ⌇H | ⌇n-C₁₄H₂₉ | ⌇n-C₁₄H₂₉ |
| 144 | S | Se | C(n-C₉H₁₉) | 0 | 0 | —S(O)₂—nC₆H₁₃ | 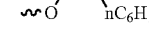—S(O)₂—nC₆H₁₃ | — | — |
| 145 | S | Se | C(n-C₆H₁₃) | 0 | 0 | ⌇CH₃ | ⌇CH₃ | — | — |
| 146 | S | Se | CH | 1 | 1 | 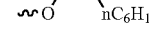 O / nC₆H₁₃ | ⌇—N(C₄H₉)₂ | ⌇OCH₃ | ⌇OCH₃ |
| 147 | S | Se | CH | 0 | 0 |  | ⌇n-C₅H₁₁ | — | — |
| 148 | S | Se | CH | 2 | 2 | ⌇CH₃ | ⌇CH₃ | ⌇CH₃ | ⌇CH₃ |

TABLE 15-continued

| Specific Example | X | Y | Z | m | n | R¹ | R² | R³ | R⁴ |
|---|---|---|---|---|---|---|---|---|---|
| 149 | S | Se | N | 0 | 0 | ⁓CH₃ | ⁓CH₃ | — | — |
| 150 | S | Se | N | 0 | 0 | ⁓n-C₁₄H₂₉ | ⁓n-C₁₄H₂₉ | — | — |

TABLE 16

| Specific Example | X | Y | Z | m | n | R¹ | R² | R³ | R⁴ |
|---|---|---|---|---|---|---|---|---|---|
| 151 | S | Se | N | 0 | 0 |  |  | — | — |
| 152 | S | Se | N | 0 | 0 |  (tBu) |  (tBu) | — | — |
| 153 | S | Se | N | 1 | 1 | ⁓CH₃ | ⁓CH₃ | ⁓CH₃ | ⁓CH₃ |
| 154 | S | Se | N | 0 | 0 | ⁓-C₃H₇ | ⁓-C₃H₇ | — | — |
| 155 | S | Se | N | 0 | 0 | ⁓CH₃ | ⁓CH₃ | — | — |
| 156 | S | Se | N | 1 | 1 |  ⁓S(O)−nC₆H₁₃ | ⁓≡−nC₇H₁₅ | ⁓SCH₃ | ⁓SCH₃ |
| 157 | S | Se | N | 0 | 0 |  | ⁓n-C₅H₁₁ | — | — |
| 158 | S | Se | N | 2 | 2 | ⁓CH₃ | ⁓CH₃ | ⁓CH₃ | ⁓CH₃ |
| 159 | S | N | O | 0 | 0 | ⁓CH₃ | ⁓CH₃ | — | — |
| 160 | S | N | O | 0 | 0 | ⁓n-C₁₄H₂₉ | ⁓n-C₁₄H₂₉ | — | — |

TABLE 17

| Specific Example | X | Y | Z | m | n | R¹ | R² | R³ | R⁴ |
|---|---|---|---|---|---|---|---|---|---|
| 161 | S | N | O | 0 | 0 | 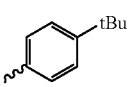 (N, F) | 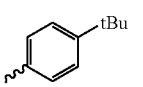 (N, F) | — | — |
| 162 | S | N | O | 0 | 0 |  (CF₃) |  (CF₃) | — | — |
| 163 | S | N | O | 1 | 1 | ⁓CH₃ | ⁓CH₃ | ⁓CH₃ | ⁓CH₃ |
| 164 | S | N | O | 0 | 0 | ⁓S(O)−nC₆H₁₃ |  ⁓S(O)−Ph | — | — |
| 165 | S | N | O | 0 | 0 | ⁓CH₃ | ⁓CH₃ | — | — |
| 166 | S | N | O | 1 | 1 | ⁓C(O)−nC₆H₁₃ | ⁓≡−nC₇H₁₅ | ⁓SCH₃ | ⁓SCH₃ |

TABLE 17-continued

| Specific Example | X | Y | Z | m | n | R¹ | R² | R³ | R⁴ |
|---|---|---|---|---|---|---|---|---|---|
| 167 | S | N | O | 0 | 0 | 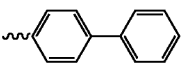 biphenyl | n-C$_5$H$_{11}$ | — | — |
| 168 | S | N | O | 2 | 2 | CH$_3$ | CH$_3$ | CH$_3$ | CH$_3$ |
| 169 | S | N | S | 0 | 0 | CH$_3$ | CH$_3$ | — | — |
| 170 | S | N | S | 0 | 0 | n-C$_9$H$_{19}$ | n-C$_9$H$_{19}$ | — | — |

TABLE 18

| Specific Example | X | Y | Z | m | n | R¹ | R² | R³ | R⁴ |
|---|---|---|---|---|---|---|---|---|---|
| 171 | S | N | S | 0 | 0 |  phenyl |  thiazole-nC$_4$H$_9$ | — | — |
| 172 | S | N | S | 0 | 0 |  4-tBu-phenyl |  4-tBu-phenyl | — | — |
| 173 | S | N | S | 1 | 1 | CH$_3$ | CH$_3$ | CH$_3$ | CH$_3$ |
| 174 | S | N | S | 0 | 0 | —S—nC$_6$H$_{13}$ | —S—nC$_6$H$_{13}$ | — | — |
| 175 | S | N | S | 0 | 0 | CH$_3$ | CH$_3$ | — | — |
| 176 | S | N | S | 1 | 2 |  2,6-dimethyl-4-nC$_5$H$_{11}$-phenyl |  2,6-dimethyl-4-nC$_5$H$_{11}$-phenyl | SCH$_3$ | SCH$_3$ |
| 177 | S | N | S | 0 | 0 | CH(nC$_6$H$_{13}$)(nC$_6$H$_{13}$) | n-C$_5$H$_{11}$ | — | — |
| 178 | S | N | Se | 0 | 0 | CH$_3$ | CH$_3$ | — | — |
| 179 | S | N | Se | 0 | 0 | n-C$_{14}$H$_{29}$ | n-C$_{14}$H$_{29}$ | — | — |
| 180 | S | N | Se | 0 | 0 |  phenyl |  N-methylpyrrole-nC$_6$H$_{13}$ | — | — |

TABLE 19

| Specific Example | X | Y | Z | m | n | R¹ | R² | R³ | R⁴ |
|---|---|---|---|---|---|---|---|---|---|
| 181 | S | N | Se | 0 | 0 | CH(nC$_6$H$_{13}$)(nC$_6$H$_{13}$) | CH(nC$_6$H$_{13}$)(nC$_6$H$_{13}$) | — | — |
| 182 | S | N | Se | 1 | 1 | H | H | n-C$_{14}$H$_{29}$ | n-C$_{14}$H$_{29}$ |

TABLE 19-continued

| Specific Example | X | Y | Z | m | n | R¹ | R² | R³ | R⁴ |
|---|---|---|---|---|---|---|---|---|---|
| 183 | S | N | Se | 0 | 0 | 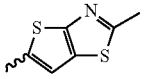 | 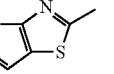 | — | — |
| 184 | S | N | Se | 0 | 0 | $CH_3$ | $CH_3$ | — | — |
| 185 | S | N | Se | 1 | 1 |  | —N$(C_4H_9)_2$ | $OCH_3$ | $OCH_3$ |
| 186 | S | N | Se | 0 | 0 |  | n-$C_5H_{11}$ | — | — |
| 187 | S | N($CH_3$) | CH | 0 | 0 | $CH_3$ | $CH_3$ | — | — |
| 188 | S | NH | CH | 0 | 0 | n-$C_{14}H_{29}$ | n-$C_{14}H_{29}$ | — | — |
| 189 | S | N($CH_3$) | CH | 0 | 0 | 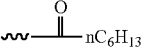 | 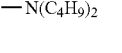 | — | — |
| 190 | S | N($CH_3$) | CH | 0 | 0 |  |  | — | — |

TABLE 20

| Specific Example | X | Y | Z | m | n | R¹ | R² | R³ | R⁴ |
|---|---|---|---|---|---|---|---|---|---|
| 191 | S | N($CH_3$) | CH | 1 | 1 | H | H | n-$C_{14}H_{29}$ | n-$C_{14}H_{29}$ |
| 192 | S | N($CH_3$) | C(n-$C_9H_{19}$) | 0 | 0 | —O—n$C_6H_{13}$ | —O—n$C_6H_{13}$ | — | — |
| 193 | S | N(n-$C_9H_{19}$) | C(n-$C_6H_{13}$) | 0 | 0 | $CH_3$ | $CH_3$ | — | — |
| 194 | S | N($CH_3$) | CH | 1 | 1 |  | —N$(C_4H_9)_2$ | $OCH_3$ | $OCH_3$ |
| 195 | S | N(i-Pr) | CH | 0 | 0 |  | n-$C_5H_{11}$ | — | — |
| 196 | S | N($CH_3$) | CH | 2 | 2 | $CH_3$ | $CH_3$ | $CH_3$ | $CH_3$ |
| 197 | Se | CH | Se | 0 | 0 | $CH_3$ | $CH_3$ | — | — |
| 198 | Se | CH | Se | 0 | 0 | n-$C_{14}H_{29}$ | n-$C_{14}H_{29}$ | — | — |
| 199 | Se | CH | Se | 0 | 0 |  |  | — | — |
| 200 | Se | CH | Se | 0 | 0 |  |  | — | — |

TABLE 21

| Specific Example | X | Y | Z | m | n | R¹ | R² | R³ | R⁴ |
|---|---|---|---|---|---|---|---|---|---|
| 201 | Se | CH | Se | 1 | 1 | $CH_3$ | $CH_3$ | $CH_3$ | $CH_3$ |
| 202 | Se | C(n-$C_8H_{17}$) | Se | 0 | 0 | H | H | — | — |
| 203 | Se | C(n-$C_6H_{13}$) | Se | 0 | 0 | $CH_3$ | $CH_3$ | — | — |
| 204 | Se | CH | Se | 1 | 1 | $-C(O)nC_6H_{13}$ | $-N(C_4H_9)_2$ | $OCH_3$ | $OCH_3$ |
| 205 | Se | CH | Se | 0 | 0 | phenyl | n-$C_5H_{11}$ | — | — |
| 206 | Se | CH | Se | 2 | 2 | $CH_3$ | $CH_3$ | $CH_3$ | $CH_3$ |
| 207 | Se | O | N | 0 | 0 | $CH_3$ | $CH_3$ | — | — |
| 208 | Se | O | N | 0 | 0 | n-$C_{14}H_{29}$ | n-$C_{14}H_{29}$ | — | — |
| 209 | Se | O | N | 0 | 0 | phenyl | phenyl | — | — |
| 210 | Se | O | N | 0 | 0 | 4-tBu-phenyl | 4-tBu-phenyl | — | — |

TABLE 22

| Specific Example | X | Y | Z | m | n | R¹ | R² | R³ | R⁴ |
|---|---|---|---|---|---|---|---|---|---|
| 211 | Se | O | N | 1 | 1 | $CH_3$ | $CH_3$ | $CH_3$ | $CH_3$ |
| 212 | Se | O | N | 0 | 0 | $-S(O)_2-nC_6H_{13}$ | $-S(O)_2-nC_6H_{13}$ | — | — |
| 213 | Se | O | N | 0 | 0 | $CH_3$ | $CH_3$ | — | — |
| 214 | Se | O | N | 1 | 1 | $-C(O)nC_6H_{13}$ | $-C\equiv C-nC_7H_{15}$ | $SCH_3$ | $SCH_3$ |
| 215 | Se | O | N | 0 | 0 | phenyl | n-$C_5H_{11}$ | — | — |
| 216 | Se | O | N | 2 | 2 | $CH_3$ | $CH_3$ | $CH_3$ | $CH_3$ |
| 217 | Se | S | N | 0 | 0 | $CH_3$ | $CH_3$ | — | — |
| 218 | Se | S | N | 0 | 0 | n-$C_9H_{19}$ | n-$C_9H_{19}$ | — | — |

TABLE 22-continued

| Specific Example | X | Y | Z | m | n | R¹ | R² | R³ | R⁴ |
|---|---|---|---|---|---|---|---|---|---|
| 219 | Se | S | N | 0 | 0 | phenyl | 5-(nC$_4$H$_9$)-furan-2-yl | — | — |
| 220 | Se | S | N | 0 | 0 | 4-tBu-phenyl | 4-tBu-phenyl | — | — |

TABLE 23

| Specific Example | X | Y | Z | m | n | R¹ | R² | R³ | R⁴ |
|---|---|---|---|---|---|---|---|---|---|
| 221 | Se | S | N | 1 | 1 | CH$_3$ | CH$_3$ | CH$_3$ | CH$_3$ |
| 222 | Se | S | N | 0 | 0 | —S—nC$_6$H$_{13}$ | —S—nC$_6$H$_{13}$ | — | — |
| 223 | Se | S | N | 0 | 0 | CH$_3$ | CH$_3$ | — | — |
| 224 | Se | S | N | 1 | 1 | —OCH$_2$CH(nC$_6$H$_{13}$)$_2$ | —OCH$_2$CH(nC$_6$H$_{13}$)$_2$ | SCH$_3$ | SCH$_3$ |
| 225 | Se | S | N | 0 | 0 | —CH(nC$_6$H$_{13}$)$_2$ | n-C$_5$H$_{11}$ | — | — |
| 226 | Se | S | N | 2 | 2 | CH$_3$ | CH$_3$ | CH$_3$ | CH$_3$ |
| 227 | Se | Se | CH | 0 | 0 | CH$_3$ | CH$_3$ | — | — |
| 228 | Se | Se | CH | 0 | 0 | n-C$_{14}$H$_{29}$ | n-C$_{14}$H$_{29}$ | — | — |
| 229 | Se | Se | CH | 0 | 0 | phenyl | phenyl | — | — |
| 230 | Se | Se | CH | 0 | 0 | 5-iPr-thiophen-2-yl | 4-tBu-phenyl | — | — |

TABLE 24

| Specific Example | X | Y | Z | m | n | R¹ | R² | R³ | R⁴ |
|---|---|---|---|---|---|---|---|---|---|
| 231 | Se | Se | CH | 1 | 1 | H | H | n-C$_{14}$H$_{29}$ | n-C$_{14}$H$_{29}$ |
| 232 | Se | Se | C(n-C$_9$H$_{19}$) | 0 | 0 | —S(O)$_2$—nC$_6$H$_{13}$ | —S(O)$_2$—nC$_6$H$_{13}$ | — | — |
| 233 | Se | Se | C(n-C$_6$H$_{13}$) | 0 | 0 | CH$_3$ | CH$_3$ | — | — |
| 234 | Se | Se | CH | 1 | 1 | —C(O)—nC$_6$H$_{13}$ | —N(C$_4$H$_9$)$_2$ | OCH$_3$ | OCH$_3$ |

TABLE 24-continued

| Specific Example | X | Y | Z | m | n | R¹ | R² | R³ | R⁴ |
|---|---|---|---|---|---|---|---|---|---|
| 235 | Se | Se | CH | 0 | 0 |  | n-C$_5$H$_{11}$ | — | — |
| 236 | Se | Se | CH | 2 | 2 | CH$_3$ | CH$_3$ | CH$_3$ | CH$_3$ |
| 237 | Se | Se | N | 0 | 0 | CH$_3$ | CH$_3$ | — | — |
| 238 | Se | Se | N | 0 | 0 | n-C$_{14}$H$_{29}$ | n-C$_{14}$H$_{29}$ | — | — |
| 239 | Se | Se | N | 0 | 0 |  |  | — | — |
| 240 | Se | Se | N | 0 | 0 |  (tBu) |  (tBu) | — | — |

TABLE 25

| Specific Example | X | Y | Z | m | n | R¹ | R² | R³ | R⁴ |
|---|---|---|---|---|---|---|---|---|---|
| 241 | Se | Se | N | 1 | 1 | CH$_3$ | CH$_3$ | CH$_3$ | CH$_3$ |
| 242 | Se | Se | N | 0 | 0 | —C$_3$H$_7$ | —C$_3$H$_7$ | — | — |
| 243 | Se | Se | N | 0 | 0 | CH$_3$ | CH$_3$ | — | — |
| 244 | Se | Se | N | 1 | 1 | —S(O)—nC$_6$H$_{13}$ | ≡—nC$_7$H$_{15}$ | SCH$_3$ | SCH$_3$ |
| 245 | Se | Se | N | 0 | 0 |  | n-C$_5$H$_{11}$ | — | — |
| 246 | Se | Se | N | 2 | 2 | CH$_3$ | CH$_3$ | CH$_3$ | CH$_3$ |
| 247 | Se | CH | O | 0 | 0 | CH$_3$ | CH$_3$ | — | — |
| 248 | Se | CH | O | 0 | 0 | n-C$_{14}$H$_{29}$ | n-C$_{14}$H$_{29}$ | — | — |
| 249 | Se | CH | O | 0 | 0 |  |  | — | — |
| 250 | Se | CH | O | 0 | 0 |  (iPr) |  (tBu) | — | — |

TABLE 26

| Specific Example | X | Y | Z | m | n | R¹ | R² | R³ | R⁴ |
|---|---|---|---|---|---|---|---|---|---|
| 251 | Se | CH | O | 1 | 1 | H | H | n-C₁₄H₂₉ | n-C₁₄H₂₉ |
| 252 | Se | C(n-C₉H₁₉) | O | 0 | 0 | S(=O)₂-n-C₆H₁₃ | S(=O)₂-n-C₆H₁₃ | — | — |
| 253 | Se | C(n-C₆H₁₃) | O | 0 | 0 | CH₃ | CH₃ | — | — |
| 254 | Se | CH | O | 1 | 1 | C(=O)-n-C₆H₁₃ | N(C₄H₉)₂ | OCH₃ | OCH₃ |
| 255 | Se | CH | O | 0 | 0 | phenyl | n-C₅H₁₁ | — | — |
| 256 | Se | CH | O | 2 | 2 | CH₃ | CH₃ | CH₃ | CH₃ |
| 257 | Se | O | CH | 0 | 0 | CH₃ | CH₃ | — | — |
| 258 | Se | O | CH | 0 | 0 | n-C₁₄H₂₉ | n-C₁₄H₂₉ | — | — |
| 259 | Se | O | CH | 0 | 0 | cyclohexyl | cyclohexyl | — | — |
| 260 | Se | O | C(n-C₉H₁₉) | 0 | 0 | 4-amyl-phenyl | 4-amyl-phenyl | — | — |

TABLE 27

| Specific Example | X | Y | Z | m | n | R¹ | R² | R³ | R⁴ |
|---|---|---|---|---|---|---|---|---|---|
| 261 | Se | S | C(n-C₆H₁₃) | 1 | 1 | CH₃ | CH₃ | CH₃ | CH₃ |
| 262 | Se | S | CH | 0 | 0 | CH=CH-C₃H₇ | CH=CH-C₃H₇ | — | — |
| 263 | Se | S | CH | 0 | 0 | CH₃ | CH₃ | — | — |
| 264 | Se | S | C(n-C₉H₁₉) | 1 | 1 | S(=O)-n-C₆H₁₃ | C≡C-n-C₇H₁₅ | SCH₃ | SCH₃ |
| 265 | Se | S | C(CH₃) | 0 | 0 | phenyl | n-C₅H₁₁ | — | — |
| 266 | Se | S | C(n-C₆H₁₃) | 2 | 2 | CH₃ | CH₃ | CH₃ | CH₃ |
| 267 | Se | N | O | 0 | 0 | CH₃ | CH₃ | — | — |
| 268 | Se | N | O | 0 | 0 | n-C₁₄H₂₉ | n-C₁₄H₂₉ | — | — |

TABLE 27-continued

| Specific Example | X | Y | Z | m | n | R¹ | R² | R³ | R⁴ |
|---|---|---|---|---|---|---|---|---|---|
| 269 | Se | N | O | 0 | 0 | 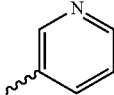 | 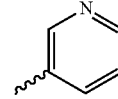 | — | — |
| 270 | Se | N | O | 0 | 0 | 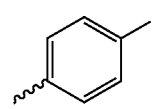 | 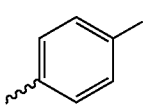 | — | — |

TABLE 28

| Specific Example | X | Y | Z | m | n | R¹ | R² | R³ | R⁴ |
|---|---|---|---|---|---|---|---|---|---|
| 271 | Se | N | O | 1 | 1 | $\sim$CH$_3$ | $\sim$CH$_3$ | $\sim$CH$_3$ | $\sim$CH$_3$ |
| 272 | Se | N | O | 0 | 0 |  |  | — | — |
| 273 | Se | N | O | 0 | 0 | $\sim$CH$_3$ | $\sim$CH$_3$ | — | — |
| 274 | Se | N | O | 1 | 1 |  | $\sim\!\!\equiv\!\!-$n-C$_7$H$_{15}$ | $\sim$SCH$_3$ | $\sim$SCH$_3$ |
| 275 | Se | N | O | 0 | 0 |  | $\sim$n-C$_5$H$_{11}$ | — | — |
| 276 | Se | N | O | 2 | 2 | $\sim$CH$_3$ | $\sim$CH$_3$ | $\sim$CH$_3$ | $\sim$CH$_3$ |
| 277 | Se | N | S | 0 | 0 | $\sim$CH$_3$ | $\sim$CH$_3$ | — | — |
| 278 | Se | N | S | 0 | 0 | $\sim$n-C$_9$H$_{19}$ | $\sim$n-C$_9$H$_{19}$ | — | — |
| 279 | Se | N | S | 0 | 0 | 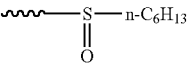 | 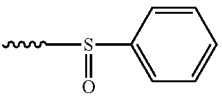 | — | — |
| 280 | Se | N | S | 0 | 0 |  |  | — | — |

TABLE 29

| Specific Example | X | Y | Z | m | n | R¹ | R² | R³ | R⁴ |
|---|---|---|---|---|---|---|---|---|---|
| 281 | Se | N | S | 1 | 1 | $\sim$CH$_3$ | $\sim$CH$_3$ | $\sim$CH$_3$ | $\sim$CH$_3$ |
| 282 | Se | N | S | 0 | 0 | $\sim$S—nC$_6$H$_{13}$ | $\sim$S—nC$_6$H$_{13}$ | — | — |
| 283 | Se | N | S | 0 | 0 | $\sim$CH$_3$ | $\sim$CH$_3$ | — | — |

TABLE 29-continued
| Specific Example | X | Y | Z | m | n | R¹ | R² | R³ | R⁴ |
|---|---|---|---|---|---|---|---|---|---|
| 284 | Se | N | S | 1 | 2 | 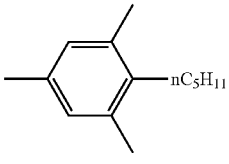 | 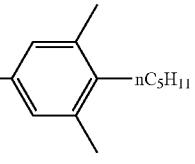 |  SCH₃ |  SCH₃ |
| 285 | Se | N | S | 0 | 0 | 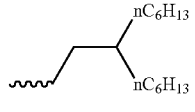 | 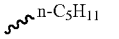 n-C₅H₁₁ | — | — |
| 286 | Se | N | Se | 0 | 0 |  CH₃ |  CH₃ | — | — |
| 287 | Se | N | Se | 0 | 0 | 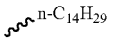 n-C₁₄H₂₉ | 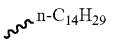 n-C₁₄H₂₉ | — | — |
| 288 | Se | N | Se | 0 | 0 | 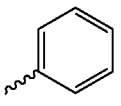 | 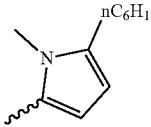 | — | — |
| 289 | Se | N | Se | 0 | 0 | 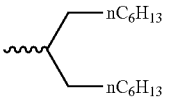 | 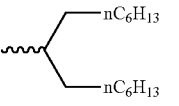 | — | — |
| 290 | Se | N | Se | 1 | 1 |  H |  H | 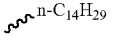 n-C₁₄H₂₉ | 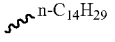 n-C₁₄H₂₉ |
TABLE 30
| Specific Example | X | Y | Z | m | n | R¹ | R² | R³ | R⁴ |
|---|---|---|---|---|---|---|---|---|---|
| 291 | Se | N | Se | 0 | 0 | 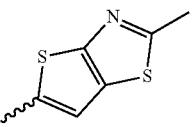 | 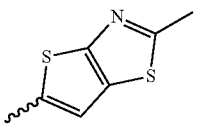 | — | — |
| 292 | Se | N | Se | 0 | 0 |  CH₃ |  CH₃ | — | — |
| 293 | Se | N | Se | 1 | 1 | 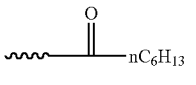 | 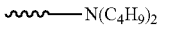 N(C₄H₉)₂ |  OCH₃ |  OCH₃ |
| 294 | Se | N | Se | 0 | 0 | 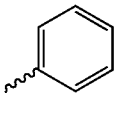 |  n-C₅H₁₁ | — | — |
| 295 | Se | N | N(CH₃) | 2 | 2 |  CH₃ |  CH₃ |  CH₃ |  CH₃ |
| 296 | Se | N | NH | 0 | 0 |  C₂H₅ |  C₂H₅ | — | — |
| 297 | Se | N | N(CH₃) | 0 | 0 | 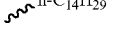 n-C₁₄H₂₉ |  n-C₁₄H₂₉ | — | — |
| 298 | Se | N | N(CH₃) | 0 | 0 | 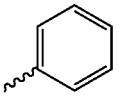 |  | — | — |

TABLE 30-continued

| Specific Example | X | Y | Z | m | n | R¹ | R² | R³ | R⁴ |
|---|---|---|---|---|---|---|---|---|---|
| 299 | Se | N | N(CH$_3$) | 0 | 0 | 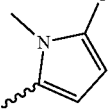 (1-methyl-2-chloropyrrol-5-yl) | 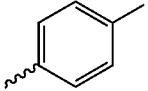 (4-tBu-phenyl) | — | — |
| 300 | Se | N | N(CH$_3$) | 1 | 1 | H | H | n-C$_{14}$H$_{29}$ | n-C$_{14}$H$_{29}$ |

TABLE 31

| Specific Example | X | Y | Z | m | n | R¹ | R² | R³ | R⁴ |
|---|---|---|---|---|---|---|---|---|---|
| 301 | Se | N | N(n-C$_9$H$_{19}$) | 0 | 0 | —C(O)—nC$_6$H$_{13}$ | —S(O)$_2$—nC$_6$H$_{13}$ | — | — |
| 302 | Se | N | N(CH$_3$) | 0 | 0 | CH$_3$ | CH$_3$ | — | — |
| 303 | Se | N | N(i-Pr) | 1 | 1 | —C(O)—nC$_6$H$_{13}$ | —N(C$_4$H$_9$)$_2$ | OCH$_3$ | OCH$_3$ |
| 304 | Se | N | N(CH$_3$) | 0 | 0 |  (pyrimidin-2-yl) | n-C$_5$H$_{11}$ | — | — |
| 305 | Se | N | N(CH$_3$) | 2 | 2 | CH$_3$ | CH$_3$ | CH$_3$ | CH$_3$ |
| 306 | Se | N(CH$_3$) | N | 0 | 0 | CH$_3$ | CH$_3$ | — | — |
| 307 | Se | NH | N | 0 | 0 | n-C$_{14}$H$_{29}$ | n-C$_{14}$H$_{29}$ | — | — |
| 308 | Se | N(CH$_3$) | N | 0 | 0 |  (phenyl) |  (phenyl) | — | — |
| 309 | Se | N(CH$_3$) | N | 0 | 0 |  (2-ethylbenzothiophen-5-yl) | 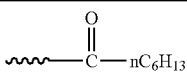 (2-ethylbenzothiophen-5-yl) | — | — |
| 310 | Se | N(CH$_3$) | N | 1 | 1 | CH$_3$ | CH$_3$ | CH$_3$ | CH$_3$ |

TABLE 32

| Specific Example | X | Y | Z | m | n | R¹ | R² | R³ | R⁴ |
|---|---|---|---|---|---|---|---|---|---|
| 311 | Se | N(CH$_3$) | N | 0 | 0 | —S(O)$_2$—nC$_6$H$_{13}$ | —S(O)$_2$—nC$_6$H$_{13}$ | — | — |
| 312 | Se | N(n-C$_9$H$_{19}$) | N | 0 | 0 | CH$_3$ | CH$_3$ | — | — |

TABLE 32-continued

| Specific Example | X | Y | Z | m | n | R¹ | R² | R³ | R⁴ |
|---|---|---|---|---|---|---|---|---|---|
| 313 | Se | N(CH₃) | N | 1 | 1 | -C(=O)-nC₆H₁₃ | -C≡C-nC₇H₁₅ | phenyl | phenyl |
| 314 | Se | N(i-Pr) | N | 0 | 0 | phenyl | n-C₅H₁₁ | — | — |
| 315 | Se | N(CH₃) | N | 2 | 2 | CH₃ | CH₃ | CH₃ | CH₃ |
| 316 | Se | N(CH₃) | CH | 0 | 0 | CH₃ | CH₃ | — | — |
| 317 | Se | NH | CH | 0 | 0 | n-C₁₄H₂₉ | n-C₁₄H₂₉ | — | — |
| 318 | Se | N(CH₃) | CH | 0 | 0 | phenyl | phenyl | — | — |
| 319 | Se | N(CH₃) | CH | 0 | 0 | CH=C(C₃H₇)(C₃H₇) | 4-tBu-phenyl | — | — |
| 320 | Se | N(CH₃) | CH | 1 | 1 | H | H | n-C₁₄H₂₉ | n-C₁₄H₂₉ |

TABLE 33

| Specific Example | X | Y | Z | m | n | R¹ | R² | R³ | R⁴ |
|---|---|---|---|---|---|---|---|---|---|
| 321 | Se | N(CH₃) | N(n-C₉H₁₉) | 0 | 0 | -O-nC₆H₁₃ | -O-nC₆H₁₃ | — | — |
| 322 | Se | N(n-C₉H₁₉) | C(n-C₆H₁₃) | 0 | 0 | CH₃ | CH₃ | — | — |
| 323 | Se | N(CH₃) | CH | 1 | 1 | -C(=O)-nC₆H₁₃ | -N(C₄H₉)₂ | OCH₃ | OCH₃ |
| 324 | Se | N(i-Pr) | CH | 0 | 0 | phenyl | n-C₅H₁₁ | — | — |
| 325 | Se | N(CH₃) | CH | 2 | 2 | CH₃ | CH₃ | CH₃ | CH₃ |
| 326 | Te | CH | Se | 0 | 0 | CH₃ | CH₃ | — | — |
| 327 | Te | CH | Se | 0 | 0 | n-C₁₄H₂₉ | n-C₁₄H₂₉ | — | — |

TABLE 33-continued

| Specific Example | X | Y | Z | m | n | R¹ | R² | R³ | R⁴ |
|---|---|---|---|---|---|---|---|---|---|
| 328 | Te | CH | Se | 0 | 0 | phenyl | phenyl | — | — |
| 329 | Te | CH | Se | 0 | 0 | 5-iPr-thiophen-2-yl | 5-iPr-thiophen-2-yl | — | — |
| 330 | Te | CH | Se | 1 | 1 | CH₃ | CH₃ | CH₃ | CH₃ |

TABLE 34

| Specific Example | X | Y | Z | m | n | R¹ | R² | R³ | R⁴ |
|---|---|---|---|---|---|---|---|---|---|
| 331 | Te | C(n-C$_8$H$_{17}$) | Se | 0 | 0 | H | H | — | — |
| 332 | Te | C(n-C$_6$H$_{13}$) | Se | 0 | 0 | CH₃ | CH₃ | — | — |
| 333 | Te | CH | Se | 1 | 1 | C(=O)nC$_6$H$_{13}$ | N(C$_4$H$_9$)$_2$ | OCH₃ | OCH₃ |
| 334 | Te | CH | Se | 0 | 0 | phenyl | n-C$_5$H$_{11}$ | — | — |
| 335 | Te | CH | Se | 2 | 2 | CH₃ | CH₃ | CH₃ | CH₃ |
| 336 | Te | O | N | 0 | 0 | CH₃ | CH₃ | — | — |
| 337 | Te | O | N | 0 | 0 | n-C$_{14}$H$_{29}$ | n-C$_{14}$H$_{29}$ | — | — |
| 338 | Te | O | N | 0 | 0 | phenyl | phenyl | — | — |
| 339 | Te | O | N | 0 | 0 | 4-tBu-phenyl | 4-tBu-phenyl | — | — |
| 340 | Te | O | N | 1 | 1 | CH₃ | CH₃ | CH₃ | CH₃ |

TABLE 35

| Specific Example | X | Y | Z | m | n | R¹ | R² | R³ | R⁴ |
|---|---|---|---|---|---|---|---|---|---|
| 341 | Te | O | N | 0 | 0 | S(=O)$_2$-nC$_6$H$_{13}$ | S(=O)$_2$-nC$_6$H$_{13}$ | — | — |
| 342 | Te | O | N | 0 | 0 | CH₃ | CH₃ | — | — |

TABLE 35-continued

| Specific Example | X | Y | Z | m | n | R¹ | R² | R³ | R⁴ |
|---|---|---|---|---|---|---|---|---|---|
| 343 | Te | O | N | 1 | 1 | -C(=O)-nC$_6$H$_{13}$ | -C≡C-nC$_7$H$_{15}$ | -SCH$_3$ | -SCH$_3$ |
| 344 | Te | O | N | 0 | 0 | phenyl | n-C$_5$H$_{11}$ | — | — |
| 345 | Te | O | N | 2 | 2 | CH$_3$ | CH$_3$ | CH$_3$ | CH$_3$ |
| 346 | Te | S | N | 0 | 0 | CH$_3$ | CH$_3$ | — | — |
| 347 | Te | S | N | 0 | 0 | n-C$_9$H$_{19}$ | n-C$_9$H$_{19}$ | — | — |
| 348 | Te | S | N | 0 | 0 | phenyl | 2-(nC$_4$H$_9$)-furyl | — | — |
| 349 | Te | S | N | 0 | 0 | 4-tBu-phenyl | 4-tBu-phenyl | — | — |
| 350 | Te | S | N | 1 | 1 | CH$_3$ | CH$_3$ | CH$_3$ | CH$_3$ |

TABLE 36

| Specific Example | X | Y | Z | m | n | R¹ | R² | R³ | R⁴ |
|---|---|---|---|---|---|---|---|---|---|
| 351 | Te | S | N | 0 | 0 | -S-nC$_6$H$_{13}$ | -S-nC$_6$H$_{13}$ | — | — |
| 352 | Te | S | N | 0 | 0 | CH$_3$ | CH$_3$ | — | — |
| 353 | Te | S | N | 1 | 1 | -O-CH(nC$_6$H$_{13}$)(nC$_6$H$_{13}$) | -O-CH(nC$_6$H$_{13}$)(nC$_6$H$_{13}$) | -SCH$_3$ | -SCH$_3$ |
| 354 | Te | S | N | 0 | 0 | -O-CH(nC$_6$H$_{13}$)(nC$_6$H$_{13}$) | n-C$_5$H$_{11}$ | — | — |
| 355 | Te | S | N | 2 | 2 | CH$_3$ | CH$_3$ | CH$_3$ | CH$_3$ |
| 356 | Te | Se | CH | 0 | 0 | CH$_3$ | CH$_3$ | — | — |
| 357 | Te | Se | CH | 0 | 0 | n-C$_{14}$H$_{29}$ | n-C$_{14}$H$_{29}$ | — | — |
| 358 | Te | Se | CH | 0 | 0 | phenyl | phenyl | — | — |

TABLE 36-continued

| Specific Example | X | Y | Z | m | n | R¹ | R² | R³ | R⁴ |
|---|---|---|---|---|---|---|---|---|---|
| 359 | Te | Se | CH | 0 | 0 | 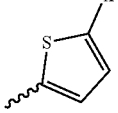 (2-iPr-thiophene) | 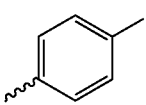 (4-tBu-phenyl) | — | — |
| 360 | Te | Se | CH | 1 | 1 | H | H | n-C$_{14}$H$_{29}$ | n-C$_{14}$H$_{29}$ |

TABLE 37

| Specific Example | X | Y | Z | m | n | R¹ | R² | R³ | R⁴ |
|---|---|---|---|---|---|---|---|---|---|
| 361 | Te | Se | C(n-C$_9$H$_{19}$) | 0 | 0 | -S(O)$_2$-nC$_6$H$_{13}$ | -S(O)$_2$-nC$_6$H$_{13}$ | — | — |
| 362 | Te | Se | C(n-C$_6$H$_{13}$) | 0 | 0 | CH$_3$ | CH$_3$ | — | — |
| 363 | Te | Se | CH | 1 | 1 | -C(O)-nC$_6$H$_{13}$ | -N(C$_4$H$_9$)$_2$ | OCH$_3$ | OCH$_3$ |
| 364 | Te | Se | CH | 0 | 0 | phenyl | n-C$_5$H$_{11}$ | — | — |
| 365 | Te | Se | CH | 2 | 2 | CH$_3$ | CH$_3$ | CH$_3$ | CH$_3$ |
| 366 | Te | Se | N | 0 | 0 | CH$_3$ | CH$_3$ | — | — |
| 367 | Te | Se | N | 0 | 0 | n-C$_{14}$H$_{29}$ | n-C$_{14}$H$_{29}$ | — | — |
| 368 | Te | Se | N | 0 | 0 | phenyl | phenyl | — | — |
| 369 | Te | Se | N | 0 | 0 | 4-tBu-phenyl | 4-tBu-phenyl | — | — |
| 370 | Te | Se | N | 1 | 1 | CH$_3$ | CH$_3$ | CH$_3$ | CH$_3$ |

TABLE 38

| Specific Example | X | Y | Z | m | n | R¹ | R² | R³ | R⁴ |
|---|---|---|---|---|---|---|---|---|---|
| 371 | Te | Se | N | 0 | 0 | -CH=CH-C$_3$H$_7$ | -CH=CH-C$_3$H$_7$ | — | — |
| 372 | Te | Se | N | 0 | 0 | CH$_3$ | CH$_3$ | — | — |
| 373 | Te | Se | N | 1 | 1 | -S(O)-nC$_6$H$_{13}$ | -C≡C-nC$_7$H$_{15}$ | SCH$_3$ | SCH$_3$ |

TABLE 38-continued

| Specific Example | X | Y | Z | m | n | R¹ | R² | R³ | R⁴ |
|---|---|---|---|---|---|---|---|---|---|
| 374 | Te | Se | N | 0 | 0 | 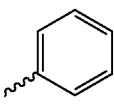 phenyl | 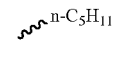 n-C$_5$H$_{11}$ | — | — |
| 375 | Te | Se | N | 2 | 2 | 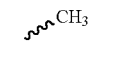 CH$_3$ |  CH$_3$ | 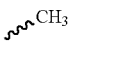 CH$_3$ |  CH$_3$ |
| 376 | Te | CH | O | 0 | 0 | 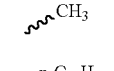 CH$_3$ | 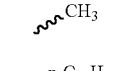 CH$_3$ | — | — |
| 377 | Te | CH | O | 0 | 0 | 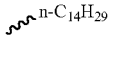 n-C$_{14}$H$_{29}$ | 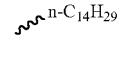 n-C$_{14}$H$_{29}$ | — | — |
| 378 | Te | CH | O | 0 | 0 | 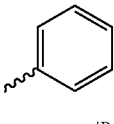 phenyl | 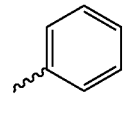 phenyl | — | — |
| 379 | Te | CH | O | 0 | 0 | 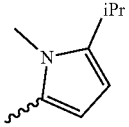 N-methylpyrrole with iPr | 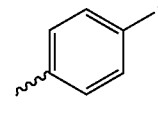 phenyl with tBu | — | — |
| 380 | Te | CH | S | 1 | 1 | 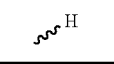 H | 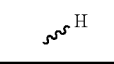 H | 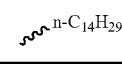 n-C$_{14}$H$_{29}$ | 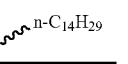 n-C$_{14}$H$_{29}$ |

TABLE 39

| Specific Example | X | Y | Z | m | n | R¹ | R² | R³ | R⁴ |
|---|---|---|---|---|---|---|---|---|---|
| 381 | Te | C(n-C$_9$H$_{19}$) | S | 0 | 0 | 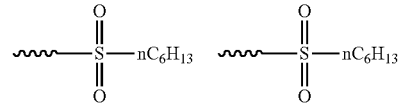 SO$_2$-nC$_6$H$_{13}$ |  SO$_2$-nC$_6$H$_{13}$ | — | — |
| 382 | Te | C(n-C$_6$H$_{13}$) | S | 0 | 0 |  CH$_3$ |  CH$_3$ | — | — |
| 383 | Te | CH | S | 1 | 1 | 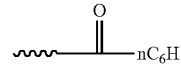 C(O)-nC$_6$H$_{13}$ | 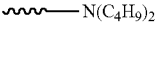 N(C$_4$H$_9$)$_2$ | 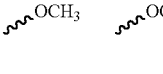 OCH$_3$ | 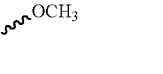 OCH$_3$ |
| 384 | Te | CH | N(CH$_3$) | 0 | 0 | 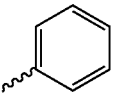 phenyl | 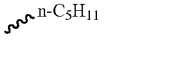 n-C$_5$H$_{11}$ | — | — |
| 385 | Te | CH | N(n-C$_3$H$_7$) | 2 | 2 |  CH$_3$ |  CH$_3$ |  CH$_3$ |  CH$_3$ |
| 386 | Te | O | CH | 0 | 0 |  CH$_3$ |  CH$_3$ | — | — |
| 387 | Te | O | CH | 0 | 0 | 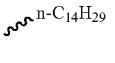 n-C$_{14}$H$_{29}$ | 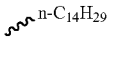 n-C$_{14}$H$_{29}$ | — | — |
| 388 | Te | O | C(n-C$_9$H$_{19}$) | 0 | 0 | 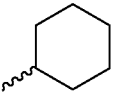 cyclohexyl | 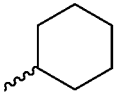 cyclohexyl | — | — |

TABLE 39-continued

| Specific Example | X | Y | Z | m | n | R¹ | R² | R³ | R⁴ |
|---|---|---|---|---|---|---|---|---|---|
| 389 | Te | O | C(n-C$_6$H$_{13}$) | 0 | 0 | 4-amyl-phenyl | 4-amyl-phenyl | — | — |
| 390 | Te | O | CH | 1 | 1 | CH$_3$ | CH$_3$ | CH$_3$ | CH$_3$ |

TABLE 40

| Specific Example | X | Y | Z | m | n | R¹ | R² | R³ | R⁴ |
|---|---|---|---|---|---|---|---|---|---|
| 391 | Te | O | CH | 0 | 0 | CH=CH-C$_3$H$_7$ | CH=CH-C$_3$H$_7$ | — | — |
| 392 | Te | S | C(n-C$_9$H$_{19}$) | 0 | 0 | CH$_3$ | CH$_3$ | — | — |
| 393 | Te | S | C(n-C$_6$H$_{13}$) | 1 | 1 | S(=O)-nC$_6$H$_{13}$ | C≡C-nC$_7$H$_{15}$ | SCH$_3$ | SCH$_3$ |
| 394 | Te | S | CH | 0 | 0 | phenyl | n-C$_5$H$_{11}$ | — | — |
| 395 | Te | S | CH | 2 | 2 | CH$_3$ | CH$_3$ | CH$_3$ | CH$_3$ |
| 396 | Te | N | O | 0 | 0 | CH$_3$ | CH$_3$ | — | — |
| 397 | Te | N | O | 0 | 0 | n-C$_{14}$H$_{29}$ | n-C$_{14}$H$_{29}$ | — | — |
| 398 | Te | N | O | 0 | 0 | 2-fluoropyridin-5-yl | 2-fluoropyridin-5-yl | — | — |
| 399 | Te | N | O | 0 | 0 | 4-CF$_3$-phenyl | 4-CF$_3$-phenyl | — | — |
| 400 | Te | N | O | 1 | 1 | CH$_3$ | CH$_3$ | CH$_3$ | CH$_3$ |

TABLE 41

| Specific Example | X | Y | Z | m | n | R¹ | R² | R³ | R⁴ |
|---|---|---|---|---|---|---|---|---|---|
| 401 | Te | N | O | 0 | 0 | S(=O)-nC$_6$H$_{13}$ | S(=O)-phenyl | — | — |
| 402 | Te | N | O | 0 | 0 | CH$_3$ | CH$_3$ | — | — |
| 403 | Te | N | O | 1 | 1 | C(=O)-nC$_6$H$_{13}$ | C≡C-nC$_7$H$_{15}$ | SCH$_3$ | SCH$_3$ |

TABLE 41-continued

| Specific Example | X | Y | Z | m | n | R¹ | R² | R³ | R⁴ |
|---|---|---|---|---|---|---|---|---|---|
| 404 | Te | N | O | 0 | 0 | biphenyl-4-yl | n-C$_5$H$_{11}$ | — | — |
| 405 | Te | N | O | 2 | 2 | CH$_3$ | CH$_3$ | CH$_3$ | CH$_3$ |
| 406 | Te | N | S | 0 | 0 | CH$_3$ | CH$_3$ | — | — |
| 407 | Te | N | S | 0 | 0 | n-C$_9$H$_{19}$ | n-C$_9$H$_{19}$ | — | — |
| 408 | Te | N | S | 0 | 0 | phenyl | 5-(nC$_4$H$_9$)-thiazol-2-yl | — | — |
| 409 | Te | N | S | 0 | 0 | 4-tBu-phenyl | 4-tBu-phenyl | — | — |
| 410 | Te | N | S | 1 | 1 | CH$_3$ | CH$_3$ | CH$_3$ | CH$_3$ |

TABLE 42

| Specific Example | X | Y | Z | m | n | R¹ | R² | R³ | R⁴ |
|---|---|---|---|---|---|---|---|---|---|
| 411 | Te | N | S | 0 | 0 | —S—nC$_6$H$_{13}$ | —S—nC$_6$H$_{13}$ | — | — |
| 412 | Te | N | S | 0 | 0 | CH$_3$ | CH$_3$ | — | — |
| 413 | Te | N | S | 1 | 2 | 2,6-dimethyl-4-(nC$_5$H$_{11}$)-phenyl | 2,6-dimethyl-4-(nC$_5$H$_{11}$)-phenyl | SCH$_3$ | SCH$_3$ |
| 414 | Te | N | S | 0 | 0 | CH(nC$_6$H$_{13}$)(CH$_2$nC$_6$H$_{13}$) | n-C$_5$H$_{11}$ | — | — |
| 415 | Te | N | Se | 0 | 0 | CH$_3$ | CH$_3$ | — | — |
| 416 | Te | N | Se | 0 | 0 | n-C$_{14}$H$_{29}$ | n-C$_{14}$H$_{29}$ | — | — |
| 417 | Te | N | Se | 0 | 0 | phenyl | 1-methyl-5-(nC$_6$H$_{13}$)-pyrrol-2-yl | — | — |
| 418 | Te | N | Se | 0 | 0 | CH(CH$_2$nC$_6$H$_{13}$)(CH$_2$nC$_6$H$_{13}$) | CH(CH$_2$nC$_6$H$_{13}$)(CH$_2$nC$_6$H$_{13}$) | — | — |

TABLE 42-continued

| Specific Example | X | Y | Z | m | n | R¹ | R² | R³ | R⁴ |
|---|---|---|---|---|---|---|---|---|---|
| 419 | Te | N | Se | 1 | 1 | H | H | n-C₁₄H₂₉ | n-C₁₄H₂₉ |
| 420 | Te | N | Se | 0 | 0 |  |  | — | — |

TABLE 43

| Specific Example | X | Y | Z | m | n | R¹ | R² | R³ | R⁴ |
|---|---|---|---|---|---|---|---|---|---|
| 421 | Te | N | Se | 0 | 0 | CH₃ | CH₃ | — | — |
| 422 | Te | N | Se | 1 | 1 |  | N(C₄H₉)₂ | OCH₃ | OCH₃ |
| 423 | Te | N | Se | 0 | 0 |  | n-C₅H₁₁ | — | — |
| 424 | Te | N | N(CH₃) | 2 | 2 | CH₃ | CH₃ | CH₃ | CH₃ |
| 425 | Te | N | NH | 0 | 0 | C₂H₅ | C₂H₅ | — | — |
| 426 | Te | N | N(CH₃) | 0 | 0 | n-C₁₄H₂₉ | n-C₁₄H₂₉ | — | — |
| 427 | Te | N | N(CH₃) | 0 | 0 | 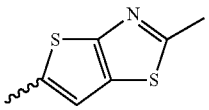 | 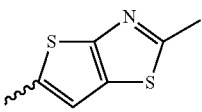 | — | — |
| 428 | Te | N | N(CH₃) | 0 | 0 |  |  | — | — |
| 429 | Te | N | N(CH₃) | 1 | 1 | H | H | n-C₁₄H₂₉ | n-C₁₄H₂₉ |
| 430 | Te | N | N(n-C₉H₁₉) | 0 | 0 | 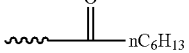 | 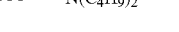 | — | — |

TABLE 44

| Specific Example | X | Y | Z | m | n | R¹ | R² | R³ | R⁴ |
|---|---|---|---|---|---|---|---|---|---|
| 431 | Te | N | N(CH₃) | 0 | 0 | CH₃ | CH₃ | — | — |
| 432 | Te | N | N(i-Pr) | 1 | 1 |  | N(C₄H₉)₂ | OCH₃ | OCH₃ |

TABLE 44-continued

| Specific Example | X | Y | Z | m | n | R¹ | R² | R³ | R⁴ |
|---|---|---|---|---|---|---|---|---|---|
| 433 | Te | N | N(CH₃) | 0 | 0 | pyrimidin-2-yl | n-C₅H₁₁ | — | — |
| 434 | Te | N | N(CH₃) | 2 | 2 | CH₃ | CH₃ | CH₃ | CH₃ |
| 435 | Te | N(CH₃) | N | 0 | 0 | CH₃ | CH₃ | — | — |
| 436 | Te | NH | N | 0 | 0 | n-C₁₄H₂₉ | n-C₁₄H₂₉ | — | — |
| 437 | Te | N(CH₃) | N | 0 | 0 | phenyl | phenyl | — | — |
| 438 | Te | N(CH₃) | N | 0 | 0 | 2-ethylbenzothiophen-5-yl | 2-ethylbenzothiophen-5-yl | — | — |
| 439 | Te | N(CH₃) | N | 1 | 1 | CH₃ | CH₃ | CH₃ | CH₃ |
| 440 | Te | N(CH₃) | N | 0 | 0 | SO₂-nC₆H₁₃ | SO₂-nC₆H₁₃ | — | — |

TABLE 45

| Specific Example | X | Y | Z | m | n | R¹ | R² | R³ | R⁴ |
|---|---|---|---|---|---|---|---|---|---|
| 441 | Te | N(n-C₉H₁₉) | N | 0 | 0 | CH₃ | CH₃ | — | — |
| 442 | Te | N(CH₃) | N | 1 | 1 | C(O)-nC₆H₁₃ | C≡C-nC₇H₁₅ | phenyl | phenyl |
| 443 | Te | N(i-Pr) | N | 0 | 0 | phenyl | n-C₅H₁₁ | — | — |
| 444 | Te | N(CH₃) | N | 2 | 2 | CH₃ | CH₃ | CH₃ | CH₃ |
| 445 | Te | N(CH₃) | CH | 0 | 0 | CH₃ | CH₃ | — | — |
| 446 | Te | NH | CH | 0 | 0 | n-C₁₄H₂₉ | n-C₁₄H₂₉ | — | — |
| 447 | Te | N(CH₃) | CH | 0 | 0 | phenyl | phenyl | — | — |
| 448 | Te | N(CH₃) | CH | 0 | 0 | C(C₃H₇)=C(C₃H₇) | 4-tBu-phenyl | — | — |

TABLE 45-continued

| Specific Example | X | Y | Z | m | n | R¹ | R² | R³ | R⁴ |
|---|---|---|---|---|---|---|---|---|---|
| 449 | Te | N(CH₃) | CH | 1 | 1 | H | H | n-C₁₄H₂₉ | n-C₁₄H₂₉ |
| 450 | Te | N(CH₃) | C(n-C₉H₁₉) | 0 | 0 | —O—nC₆H₁₃ | —O—nC₆H₁₃ | — | — |

10

TABLE 46

| Specific Example | X | Y | Z | m | n | R¹ | R² | R³ | R⁴ |
|---|---|---|---|---|---|---|---|---|---|
| 451 | Te | N(n-C₉H₁₉) | C(n-C₆H₁₃) | 0 | 0 | CH₃ | CH₃ | — | — |
| 452 | Te | N(CH₃) | CH | 1 | 1 | C(=O)nC₆H₁₃ | —N(C₄H₉)₂ | OCH₃ | OCH₃ |
| 453 | Te | N(i-Pr) | CH | 0 | 0 | phenyl | n-C₅H₁₁ | — | — |
| 454 | Te | N(CH₃) | CH | 2 | 2 | CH₃ | CH₃ | CH₃ | CH₃ |
| 455 | N(CH₃) | CH | Se | 0 | 0 | CH₃ | CH₃ | — | — |
| 456 | NH | CH | Se | 0 | 0 | n-C₁₄H₂₉ | n-C₁₄H₂₉ | — | — |
| 457 | N(CH₃) | CH | Se | 0 | 0 | phenyl | phenyl | — | — |
| 458 | N(CH₃) | CH | Se | 0 | 0 | 5-iPr-thiophen-2-yl | 5-iPr-thiophen-2-yl | — | — |
| 459 | N(CH₃) | CH | Se | 1 | 1 | CH₃ | CH₃ | CH₃ | CH₃ |
| 460 | N(CH₃) | C(n-C₈H₁₇) | Se | 0 | 0 | H | H | — | — |

TABLE 47

| Specific Example | X | Y | Z | m | n | R¹ | R² | R³ | R⁴ |
|---|---|---|---|---|---|---|---|---|---|
| 461 | N(n-C₉H₁₉) | C(n-C₆H₁₃) | Se | 0 | 0 | CH₃ | CH₃ | — | — |
| 462 | N(CH₃) | CH | Se | 1 | 1 | C(=O)nC₆H₁₃ | —N(C₄H₉)₂ | OCH₃ | OCH₃ |
| 463 | N(i-Pr) | CH | Se | 0 | 0 | phenyl | n-C₅H₁₁ | — | — |
| 464 | N(CH₃) | CH | Se | 2 | 2 | CH₃ | CH₃ | CH₃ | CH₃ |

TABLE 47-continued

| Specific Example | X | Y | Z | m | n | R¹ | R² | R³ | R⁴ |
|---|---|---|---|---|---|---|---|---|---|
| 465 | N(CH₃) | O | N | 0 | 0 | —CH₃ | —CH₃ | — | — |
| 466 | NH | O | N | 0 | 0 | —n-C₁₄H₂₉ | —n-C₁₄H₂₉ | — | — |
| 467 | N(CH₃) | O | N | 0 | 0 | —Ph | —Ph | — | — |
| 468 | N(CH₃) | O | N | 0 | 0 | —C₆H₄-tBu (p) | —C₆H₄-tBu (p) | — | — |
| 469 | N(CH₃) | O | N | 1 | 1 | —CH₃ | —CH₃ | —CH₃ | —CH₃ |
| 470 | N(CH₃) | O | N | 0 | 0 | —S(O)₂—nC₆H₁₃ | —S(O)₂—nC₆H₁₃ | — | — |

TABLE 48

| Specific Example | X | Y | Z | m | n | R¹ | R² | R³ | R⁴ |
|---|---|---|---|---|---|---|---|---|---|
| 471 | N(n-C₉H₁₉) | O | N | 0 | 0 | —CH₃ | —CH₃ | — | — |
| 472 | N(CH₃) | O | N | 1 | 1 | —C(O)—nC₆H₁₃ | —C≡C—nC₇H₁₅ | —SCH₃ | —SCH₃ |
| 473 | N(i-Pr) | O | N | 0 | 0 | —Ph | —n-C₅H₁₁ | — | — |
| 474 | N(CH₃) | O | N | 2 | 2 | —CH₃ | —CH₃ | —CH₃ | —CH₃ |
| 475 | N(CH₃) | S | N | 0 | 0 | —CH₃ | —CH₃ | — | — |
| 476 | NH | S | N | 0 | 0 | —n-C₉H₁₉ | —n-C₉H₁₉ | — | — |
| 477 | N(CH₃) | S | N | 0 | 0 | —Ph | —(2-furyl)-5-nC₄H₉ | — | — |
| 478 | N(CH₃) | S | N | 0 | 0 | —C₆H₄-tBu (p) | —C₆H₄-tBu (p) | — | — |
| 479 | N(CH₃) | S | N | 1 | 1 | —CH₃ | —CH₃ | —CH₃ | —CH₃ |
| 480 | N(CH₃) | S | N | 0 | 0 | —S—nC₆H₁₃ | —S—nC₆H₁₃ | — | — |

TABLE 49

| Specific Example | X | Y | Z | m | n | R¹ | R² | R³ | R⁴ |
|---|---|---|---|---|---|---|---|---|---|
| 481 | N(n-C$_9$H$_{19}$) | S | N | 0 | 0 | ⌇CH$_3$ | ⌇CH$_3$ | — | — |
| 482 | N(CH$_3$) | S | N | 1 | 1 | ⌇O-CH(nC$_6$H$_{13}$)CH$_2$nC$_6$H$_{13}$ | ⌇O-CH(nC$_6$H$_{13}$)CH$_2$nC$_6$H$_{13}$ | ⌇SCH$_3$ | ⌇SCH$_3$ |
| 483 | N(i-Pr) | S | N | 0 | 0 | ⌇CH(nC$_6$H$_{13}$)CH$_2$nC$_6$H$_{13}$ | ⌇n-C$_5$H$_{11}$ | — | — |
| 484 | N(CH$_3$) | S | N | 2 | 2 | ⌇CH$_3$ | ⌇CH$_3$ | ⌇CH$_3$ | ⌇CH$_3$ |
| 485 | N(CH$_3$) | Se | CH | 0 | 0 | ⌇CH$_3$ | ⌇CH$_3$ | — | — |
| 486 | NH | Se | CH | 0 | 0 | ⌇n-C$_{14}$H$_{29}$ | ⌇n-C$_{14}$H$_{29}$ | — | — |
| 487 | N(CH$_3$) | Se | CH | 0 | 0 | ⌇Ph | ⌇Ph | — | — |
| 488 | N(CH$_3$) | Se | CH | 0 | 0 | ⌇(2-iPr-thiophen-5-yl) | ⌇(4-tBu-phenyl) | — | — |
| 489 | N(CH$_3$) | Se | CH | 1 | 1 | ⌇H | ⌇H | ⌇n-C$_{14}$H$_{29}$ | ⌇n-C$_{14}$H$_{29}$ |
| 490 | N(CH$_3$) | Se | C(n-C$_9$H$_{19}$) | 0 | 0 | ⌇SO$_2$-nC$_6$H$_{13}$ | ⌇SO$_2$-nC$_6$H$_{13}$ | — | — |

TABLE 50

| Specific Example | X | Y | Z | m | n | R¹ | R² | R³ | R⁴ |
|---|---|---|---|---|---|---|---|---|---|
| 491 | N(n-C$_9$H$_{19}$) | Se | C(n-C$_6$H$_{13}$) | 0 | 0 | ⌇CH$_3$ | ⌇CH$_3$ | — | — |
| 492 | N(CH$_3$) | Se | CH | 1 | 1 | ⌇C(O)nC$_6$H$_{13}$ | ⌇N(C$_4$H$_9$)$_2$ | ⌇OCH$_3$ | ⌇OCH$_3$ |
| 493 | NH | Se | CH | 0 | 0 | ⌇Ph | ⌇n-C$_5$H$_{11}$ | — | — |
| 494 | N(CH$_3$) | Se | CH | 2 | 2 | ⌇CH$_3$ | ⌇CH$_3$ | ⌇CH$_3$ | ⌇CH$_3$ |
| 495 | N(CH$_3$) | Se | N | 0 | 0 | ⌇CH$_3$ | ⌇CH$_3$ | — | — |
| 496 | N(CH$_3$) | Se | N | 0 | 0 | ⌇n-C$_{14}$H$_{29}$ | ⌇n-C$_{14}$H$_{29}$ | — | — |
| 497 | N(CH$_3$) | Se | N | 0 | 0 | ⌇Ph | ⌇Ph | — | — |

TABLE 50-continued

| Specific Example | X | Y | Z | m | n | R¹ | R² | R³ | R⁴ |
|---|---|---|---|---|---|---|---|---|---|
| 498 | N(n-C₉H₁₉) | Se | N | 0 | 0 | 4-tBu-phenyl | 4-tBu-phenyl | — | — |
| 499 | N(CH₃) | Se | N | 1 | 1 | CH₃ | CH₃ | CH₃ | CH₃ |
| 500 | N(i-Pr) | Se | N | 0 | 0 | CH=CH-C₃H₇ | CH=CH-C₃H₇ | — | — |

TABLE 51

| Specific Example | X | Y | Z | m | n | R¹ | R² | R³ | R⁴ |
|---|---|---|---|---|---|---|---|---|---|
| 501 | N(CH₃) | Se | N | 0 | 0 | CH₃ | CH₃ | — | — |
| 502 | N(CH₃) | Se | N | 1 | 1 | S(=O)-nC₆H₁₃ | C≡C-nC₇H₁₅ | SCH₃ | SCH₃ |
| 503 | NH | Se | N | 0 | 0 | phenyl | n-C₅H₁₁ | — | — |
| 504 | N(CH₃) | Se | N | 2 | 2 | CH₃ | CH₃ | CH₃ | CH₃ |
| 505 | N(CH₃) | CH | O | 0 | 0 | CH₃ | CH₃ | — | — |
| 506 | N(CH₃) | CH | O | 0 | 0 | n-C₁₄H₂₉ | n-C₁₄H₂₉ | — | — |
| 507 | N(CH₃) | CH | O | 0 | 0 | phenyl | phenyl | — | — |
| 508 | NH | CH | O | 0 | 0 | 1-methyl-2-iPr-pyrrol-5-yl | 4-tBu-phenyl | — | — |
| 509 | N(CH₃) | CH | S | 1 | 1 | CH₃ | CH₃ | n-C₁₄H₂₉ | n-C₁₄H₂₉ |
| 510 | N(CH₃) | (n-C₉H₁₉) | S | 0 | 0 | S(O)₂-nC₆H₁₃ | S(O)₂-nC₆H₁₃ | — | — |

TABLE 52

| Specific Example | X | Y | Z | m | n | R¹ | R² | R³ | R⁴ |
|---|---|---|---|---|---|---|---|---|---|
| 511 | N(CH₃) | C(n-C₆H₁₃) | S | 0 | 0 | CH₃ | CH₃ | — | — |
| 512 | N(CH₃) | CH | S | 1 | 1 | C(=O)-nC₆H₁₃ | N(C₄H₉)₂ | OCH₃ | OCH₃ |

TABLE 52-continued

| Specific Example | X | Y | Z | m | n | R¹ | R² | R³ | R⁴ |
|---|---|---|---|---|---|---|---|---|---|
| 513 | N(n-C₉H₁₉) | CH | N(CH₃) | 0 | 0 | phenyl | n-C₅H₁₁ | — | — |
| 514 | N(CH₃) | CH | N(n-C₃H₇) | 2 | 2 | CH₃ | CH₃ | CH₃ | CH₃ |
| 515 | N(i-Pr) | O | CH | 0 | 0 | CH₃ | CH₃ | — | — |
| 516 | N(CH₃) | O | CH | 0 | 0 | n-C₁₄H₂₉ | n-C₁₄H₂₉ | — | — |
| 517 | N(CH₃) | O | C(n-C₉H₁₉) | 0 | 0 | cyclohexyl | cyclohexyl | — | — |
| 518 | NH | O | C(n-C₆H₁₃) | 0 | 0 | 4-amyl-phenyl | 4-amyl-phenyl | — | — |
| 519 | N(CH₃) | O | CH | 1 | 1 | CH₃ | CH₃ | CH₃ | CH₃ |
| 520 | N(CH₃) | O | CH | 0 | 0 | CH=CH-C₃H₇ | CH=CH-C₃H₇ | — | — |

TABLE 53

| Specific Example | X | Y | Z | m | n | R¹ | R² | R³ | R⁴ |
|---|---|---|---|---|---|---|---|---|---|
| 521 | N(CH₃) | S | C(n-C₉H₁₉) | 0 | 0 | CH₃ | CH₃ | — | — |
| 522 | N(CH₃) | S | C(n-C₆H₁₃) | 1 | 1 | S(=O)-nC₆H₁₃ | C≡C-nC₇H₁₅ | SCH₃ | SCH₃ |
| 523 | N(n-C₉H₁₉) | S | CH | 0 | 0 | phenyl | n-C₅H₁₁ | — | — |
| 524 | N(CH₃) | S | CH | 2 | 2 | CH₃ | CH₃ | CH₃ | CH₃ |
| 525 | N(i-Pr) | N | S | 0 | 0 | CH₃ | CH₃ | — | — |
| 526 | N(CH₃) | N | S | 0 | 0 | n-C₁₄H₂₉ | n-C₁₄H₂₉ | — | — |
| 527 | N(CH₃) | N | S | 0 | 0 | 2-fluoropyridin-5-yl | 2-fluoropyridin-5-yl | — | — |
| 528 | NH | N | S | 0 | 0 | 4-CF₃-phenyl | 4-CF₃-phenyl | — | — |

TABLE 53-continued

| Specific Example | X | Y | Z | m | n | R¹ | R² | R³ | R⁴ |
|---|---|---|---|---|---|---|---|---|---|
| 529 | N(CH₃) | N | S | 1 | 1 | ⌇CH₃ | ⌇CH₃ | ⌇CH₃ | ⌇CH₃ |
| 530 | N(CH₃) | N | S | 0 | 0 | ⌇S(O)—nC₆H₁₃ | ⌇S(O)—phenyl | — | — |

TABLE 54

| Specific Example | X | Y | Z | m | n | R¹ | R² | R³ | R⁴ |
|---|---|---|---|---|---|---|---|---|---|
| 531 | N(CH₃) | N | S | 0 | 0 | ⌇CH₃ | ⌇CH₃ | — | — |
| 532 | N(CH₃) | N | S | 1 | 1 | ⌇C(O)—nC₆H₁₃ | ⌇C≡C—nC₇H₁₅ | ⌇SCH₃ | ⌇SCH₃ |
| 533 | N(n-C₉H₁₉) | N | S | 0 | 0 | ⌇-biphenyl | ⌇n-C₅H₁₁ | — | — |
| 534 | N(CH₃) | N | S | 2 | 2 | ⌇CH₃ | ⌇CH₃ | ⌇CH₃ | ⌇CH₃ |
| 535 | N(i-Pr) | N | O | 0 | 0 | ⌇CH₃ | ⌇CH₃ | — | — |
| 536 | N(CH₃) | N | O | 0 | 0 | ⌇n-C₉H₁₉ | ⌇n-C₉H₁₉ | — | — |
| 537 | N(CH₃) | N | O | 0 | 0 | ⌇phenyl | ⌇2-(5-nC₄H₉-thiazolyl) | — | — |
| 538 | NH | N | O | 0 | 0 | ⌇(4-tBu-phenyl) | ⌇(4-tBu-phenyl) | — | — |
| 539 | N(CH₃) | N | O | 1 | 1 | ⌇CH₃ | ⌇CH₃ | ⌇CH₃ | ⌇CH₃ |
| 540 | N(CH₃) | N | O | 0 | 0 | ⌇S—nC₆H₁₃ | ⌇S—nC₆H₁₃ | — | — |

TABLE 55

| Specific Example | X | Y | Z | m | n | R¹ | R² | R³ | R⁴ |
|---|---|---|---|---|---|---|---|---|---|
| 541 | N(CH₃) | N | O | 0 | 0 | ⌇CH₃ | ⌇CH₃ | — | — |
| 542 | N(CH₃) | N | O | 1 | 2 | ⌇(2,6-dimethyl-4-nC₅H₁₁-phenyl) | ⌇(2,6-dimethyl-4-nC₅H₁₁-phenyl) | ⌇SCH₃ | ⌇SCH₃ |

TABLE 55-continued

| Specific Example | X | Y | Z | m | n | R¹ | R² | R³ | R⁴ |
|---|---|---|---|---|---|---|---|---|---|
| 543 | N(n-C$_9$H$_{19}$) | N | O | 0 | 0 | 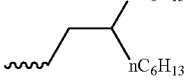 nC$_6$H$_{13}$, nC$_6$H$_{13}$ |  n-C$_5$H$_{11}$ | — | — |
| 544 | N(CH$_3$) | N | Se | 0 | 0 |  CH$_3$ |  CH$_3$ | — | — |
| 545 | N(i-Pr) | N | Se | 0 | 0 | 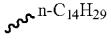 n-C$_{14}$H$_{29}$ | 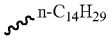 n-C$_{14}$H$_{29}$ | — | — |
| 546 | N(CH$_3$) | N | Se | 0 | 0 | 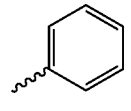 | 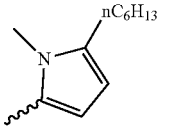 nC$_6$H$_{13}$ | — | — |
| 547 | N(CH$_3$) | N | Se | 0 | 0 | 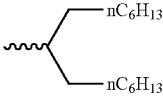 nC$_6$H$_{13}$, nC$_6$H$_{13}$ | 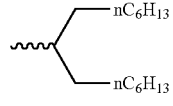 nC$_6$H$_{13}$, nC$_6$H$_{13}$ | — | — |
| 548 | NH | N | Se | 1 | 1 |  H |  H | 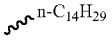 n-C$_{14}$H$_{29}$ |  n-C$_{14}$H$_{29}$ |
| 549 | N(CH$_3$) | N | Se | 0 | 0 | 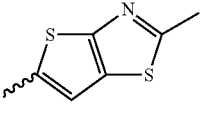 | 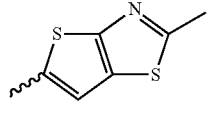 | — | — |
| 550 | N(CH$_3$) | N | Se | 0 | 0 |  CH$_3$ |  CH$_3$ | — | — |

TABLE 56

| Specific Example | X | Y | Z | m | n | R¹ | R² | R³ | R⁴ |
|---|---|---|---|---|---|---|---|---|---|
| 551 | N(CH$_3$) | N | Se | 1 | 1 | 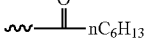 nC$_6$H$_{13}$ | 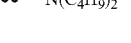 —N(C$_4$H$_9$)$_2$ |  OCH$_3$ |  OCH$_3$ |
| 552 | N(CH$_3$) | N | Se | 0 | 0 |  |  n-C$_5$H$_{11}$ | — | — |
| 553 | N(n-C$_9$H$_{19}$) | N | N(CH$_3$) | 2 | 2 |  CH$_3$ |  CH$_3$ |  CH$_3$ |  CH$_3$ |
| 554 | N(CH$_3$) | N | NH | 0 | 0 |  C$_2$H$_5$ |  C$_2$H$_5$ | — | — |
| 555 | N(i-Pr) | N | N(CH$_3$) | 0 | 0 |  n-C$_{14}$H$_{29}$ |  n-C$_{14}$H$_{29}$ | — | — |
| 556 | N(CH$_3$) | N | N(CH$_3$) | 0 | 0 |  |  | — | — |
| 557 | N(CH$_3$) | N | N(CH$_3$) | 0 | 0 |  |  | — | — |

TABLE 56-continued

| Specific Example | X | Y | Z | m | n | R¹ | R² | R³ | R⁴ |
|---|---|---|---|---|---|---|---|---|---|
| 558 | NH | N | N(CH$_3$) | 1 | 1 | H | H | n-C$_{14}$H$_{29}$ | n-C$_{14}$H$_{29}$ |
| 559 | N(CH$_3$) | N | N(n-C$_9$H$_{19}$) | 0 | 0 | ~C(=O)-nC$_6$H$_{13}$ | ~S(=O)$_2$-nC$_6$H$_{13}$ | — | — |
| 560 | N(CH$_3$) | N | N(CH$_3$) | 0 | 0 | CH$_3$ | CH$_3$ | — | — |

TABLE 57

| Specific Example | X | Y | Z | m | n | R¹ | R² | R³ | R⁴ |
|---|---|---|---|---|---|---|---|---|---|
| 561 | N(CH$_3$) | N | N(i-Pr) | 1 | 1 | ~C(=O)-nC$_6$H$_{13}$ | N(C$_4$H$_9$)$_2$ | OCH$_3$ | OCH$_3$ |
| 562 | N(CH$_3$) | N | N(CH$_3$) | 0 | 0 | pyrimidin-2-yl | n-C$_5$H$_{11}$ | — | — |
| 563 | N(n-C$_9$H$_{19}$) | N | N(CH$_3$) | 2 | 2 | CH$_3$ | CH$_3$ | CH$_3$ | CH$_3$ |
| 564 | N(CH$_3$) | N(CH$_3$) | N | 0 | 0 | CH$_3$ | CH$_3$ | — | — |
| 565 | N(CH$_3$) | NH | N | 0 | 0 | n-C$_{14}$H$_{29}$ | n-C$_{14}$H$_{29}$ | — | — |
| 566 | NH | N(CH$_3$) | N | 0 | 0 | phenyl | phenyl | — | — |
| 567 | N(CH$_3$) | N(CH$_3$) | N | 0 | 0 | 2-ethylbenzothiophen-5-yl | 2-ethylbenzothiophen-5-yl | — | — |
| 568 | N(CH$_3$) | N(CH$_3$) | N | 1 | 1 | CH$_3$ | CH$_3$ | CH$_3$ | CH$_3$ |
| 569 | N(CH$_3$) | N(CH$_3$) | N | 0 | 0 | ~S(=O)$_2$-nC$_6$H$_{13}$ | ~S(=O)$_2$-nC$_6$H$_{13}$ | — | — |
| 570 | N(CH$_3$) | N(n-C$_9$H$_{19}$) | N | 0 | 0 | CH$_3$ | CH$_3$ | — | — |

TABLE 58

| Specific Example | X | Y | Z | m | n | R¹ | R² | R³ | R⁴ |
|---|---|---|---|---|---|---|---|---|---|
| 571 | N(n-C$_9$H$_{19}$) | N(CH$_3$) | N | 1 | 1 | ~C(=O)-nC$_6$H$_{13}$ | ~C≡C-nC$_7$H$_{15}$ | phenyl | phenyl |
| 572 | N(CH$_3$) | N(i-Pr) | N | 0 | 0 | phenyl | n-C$_5$H$_{11}$ | — | — |
| 573 | N(i-Pr) | N(CH$_3$) | N | 2 | 2 | CH$_3$ | CH$_3$ | CH$_3$ | CH$_3$ |

TABLE 58-continued

| Specific Example | X | Y | Z | m | n | R¹ | R² | R³ | R⁴ |
|---|---|---|---|---|---|---|---|---|---|
| 574 | N(CH$_3$) | N(CH$_3$) | CH | 0 | 0 | CH$_3$ | CH$_3$ | — | — |
| 575 | N(CH$_3$) | NH | CH | 0 | 0 | n-C$_{14}$H$_{29}$ | n-C$_{14}$H$_{29}$ | — | — |
| 576 | NH | N(CH$_3$) | CH | 0 | 0 | phenyl | phenyl | — | — |
| 577 | N(CH$_3$) | N(CH$_3$) | CH | 0 | 0 | C(C$_3$H$_7$)=C(C$_3$H$_7$) | 4-tBu-phenyl | — | — |
| 578 | N(CH$_3$) | N(CH$_3$) | CH | 1 | 1 | H | H | n-C$_{14}$H$_{29}$ | n-C$_{14}$H$_{29}$ |
| 579 | N(CH$_3$) | N(CH$_3$) | C(n-C$_9$H$_{19}$) | 0 | 0 | —O—nC$_6$H$_{13}$ | —O—nC$_6$H$_{13}$ | — | — |
| 580 | N(CH$_3$) | N(n-C$_9$H$_{19}$) | C(n-C$_6$H$_{13}$) | 0 | 0 | CH$_3$ | CH$_3$ | — | — |

TABLE 59

| Specific Example | X | Y | Z | m | n | R¹ | R² | R³ | R⁴ |
|---|---|---|---|---|---|---|---|---|---|
| 581 | N(n-C$_9$H$_{19}$) | N(CH$_3$) | CH | 1 | 1 | —C(=O)nC$_6$H$_{13}$ | —N(C$_4$H$_9$)$_2$ | OCH$_3$ | OCH$_3$ |
| 582 | N(CH$_3$) | N(i-Pr) | CH | 0 | 0 | phenyl | n-C$_5$H$_{11}$ | — | — |
| 583 | N(i-Pr) | N(CH$_3$) | CH | 2 | 2 | CH$_3$ | CH$_3$ | CH$_3$ | CH$_3$ |
| 584 | S | CH | S | 0 | 0 | CH$_3$ | CH$_3$ | — | — |
| 585 | S | CH | S | 0 | 0 | n-C$_9$H$_{19}$ | n-C$_9$H$_{19}$ | — | — |
| 586 | S | CH | S | 0 | 0 | n-C$_3$H$_7$ | n-C$_3$H$_7$ | — | — |
| 587 | S | CH | S | 0 | 0 | n-C$_4$H$_9$ | n-C$_4$H$_9$ | — | — |
| 588 | S | CH | S | 0 | 0 | n-C$_5$H$_{11}$ | n-C$_5$H$_{11}$ | — | — |
| 589 | S | CH | S | 0 | 0 | n-C$_8$H$_{17}$ | n-C$_8$H$_{17}$ | — | — |
| 590 | S | CH | S | 0 | 0 | n-C$_{10}$H$_{21}$ | n-C$_{10}$H$_{21}$ | — | — |

TABLE 60

| Specific Example | X | Y | Z | m | n | R¹ | R² | R³ | R⁴ |
|---|---|---|---|---|---|---|---|---|---|
| 591 | S | CH | S | 0 | 0 | n-C$_{13}$H$_{27}$ | n-C$_{13}$H$_{27}$ | — | — |
| 592 | S | CH | S | 0 | 0 | n-C$_4$H$_9$ | n-C$_5$H$_{11}$ | — | — |

TABLE 60-continued

| Specific Example | X | Y | Z | m | n | R¹ | R² | R³ | R⁴ |
|---|---|---|---|---|---|---|---|---|---|
| 593 | S | CH | S | 0 | 0 | n-C₄H₉ | n-C₈H₁₇ | — | — |
| 594 | S | CH | S | 0 | 0 | n-C₄H₉ | n-C₁₀H₂₁ | — | — |
| 595 | S | CH | S | 0 | 0 | n-C₅H₁₁ | n-C₈H₁₇ | — | — |
| 596 | S | CH | S | 0 | 0 | n-C₈H₁₇ | n-C₁₀H₂₁ | — | — |
| 597 | S | CH | S | 0 | 0 | n-C₁₀H₂₁ | n-C₃H₇ | — | — |
| 598 | S | CH | S | 0 | 0 |  |  | — | — |
| 599 | S | CH | S | 0 | 0 | i-Pr | i-Pr | — | — |
| 600 | S | CH | S | 0 | 0 | t-Bu | n-C₃H₇ | — | — |
| 601 | S | CH | S | 0 | 0 |  | n-C₃H₇ | — | — |
| 602 | O | CH | Se | 1 | 1 | n-C₁₀H₂₁ | n-C₁₀H₂₁ | F | F |
| 603 | O | CH | Se | 1 | 1 | n-C₁₀H₂₁ | n-C₁₀H₂₁ | Cl | Cl |

The microcrystalline film according to the embodiment of the present invention can be formed, for example, by vapor-depositing the compound represented by Formula (1) that has a molecular weight of 3000 or lower (hereinafter, also referred to as "organic semiconductor compound according to the present invention") to a substrate. In a case where a film is formed by applying the organic semiconductor compound according to the present invention using a solution process, the film is likely to be crystallized, and a crystalline film having an extremely large crystal domain size is formed. In practice, in JP2015-195361A and JP2015-195362A, a compound as the organic semiconductor compound according to the present invention is dissolved in an organic solvent to prepare a coating solution, this coating solution is applied to form a film, and whether or not the film is crystallized is observed with a polarizing microscope. A crystalline structure that can be observed with the polarizing microscope has a large crystal domain size of more than several micrometers.

On the other hand, the crystal domain size of the microcrystalline film according to the embodiment of the present invention is in a range of 1 nm to 100 nm. This microcrystalline structure cannot be observed with the polarizing microscope and, as described in Examples below, can be detected using an atomic force microscope (AFM).

The present inventors found that, by vapor-depositing the organic semiconductor compound according to the present invention to form a film, the obtained film can be made to be in a microcrystalline state. By using this microcrystalline film as an organic semiconductor layer of an organic semiconductor transistor, the performance of the obtained transistor can be made to be highly uniform. The reason for this is presumed to be that, even in a case where an external pressure is applied, a gap between crystal domains in the microcrystalline structure functions as a cushion such that the pressure can be dispersed. For example, in a case where a crack is formed at any position of a crystalline film having a large domain size, the crack tends to propagate to cross the film. However, this phenomenon does not occur in the microcrystalline film. In addition, even in a case where the microcrystalline film is exposed to heat, similarly, a crack is not likely to be formed in the film.

A vapor deposition method for forming the microcrystalline film according to the embodiment of the present invention is not particularly limited, and a typical vapor deposition method may be applied. It is preferable that the microcrystalline film is formed by vacuum deposition.

The thickness of the microcrystalline film according to the embodiment of the present invention is preferably 1 to 100 nm and more preferably 5 to 70 nm.

The microcrystalline film according to the embodiment of the present invention can be preferably used as an organic semiconductor of an organic semiconductor transistor according to the embodiment of the present invention. The organic semiconductor transistor according to the embodiment of the present invention will be described below.

[Organic Semiconductor Transistor]

The organic semiconductor transistor according to the embodiment of the present invention (hereinafter, also referred to as "transistor according to the embodiment of the present invention") includes the microcrystalline film according to the embodiment of the present invention as an organic semiconductor layer and may further include a source electrode, a drain electrode, and a gate electrode.

The transistor according to the present invention includes, on a substrate, a gate electrode, an organic semiconductor layer, a gate insulating layer that is provided between the gate electrode and the organic semiconductor layer, and a source electrode and a drain electrode that are provided adjacent to the organic semiconductor layer and are linked to each other through the organic semiconductor layer.

A structure of the film transistor according to the embodiment of the present invention is not particularly limited as long as it includes the respective layers. For example, any structure such as a bottom contact type (a bottom gate-bottom contact type and a top gate-bottom contact type) or a top contact type (a bottom gate-top contact type and a top gate-top contact type) may be adopted. It is more preferable that the transistor according to the embodiment of the present invention is a bottom gate-bottom contact type or bottom gate-top contact type (collectively referred to as "bottom gate type").

Hereinafter, an example of the transistor according to the embodiment of the present invention will be described with reference to the accompanying drawings.

(Bottom Gate-Bottom Contact Type)

FIG. 1 is schematic cross-sectional view showing a bottom gate-bottom contact type organic semiconductor transistor 100 that is an example of the film transistor according to an embodiment of the present invention.

As shown in FIG. 1, the organic semiconductor transistor 100 includes a substrate (base material) 10, a gate electrode 20, a gate insulating film 30, a source electrode 40 and a drain electrode 42, an organic semiconductor film 50, and a sealing layer 60 in this order.

Hereinafter, the substrate (base material), the gate electrode, the gate insulating layer (film), the source electrode, the drain electrode, the organic semiconductor layer (film), and the sealing layer, and preparation methods thereof will be described in detail.

—Substrate—

The substrate functions to support the gate electrode, the source electrode, the drain electrode, and the like described below.

The kind of the substrate is not particularly limited, and examples thereof include a plastic substrate, a silicon substrate, a glass substrate, and a ceramic substrate. In particular, from the viewpoints of versatility, applicability to each device and costs, a silicon substrate, a glass substrate, or a plastic substrate is preferable.

The thickness of the substrate is not particularly limited and is, for example, preferably 10 mm or less, more preferably 2 mm or less, and still more preferably 1.5 mm or less. On the other hand, the thickness of the substrate is preferably 0.01 mm or more and more preferably 0.05 mm or more.

—Gate Electrode—

As the gate electrode, a typical electrode that is used as a gate electrode of an organic TFT element can be used without any particular limitation.

A material (electrode material) which forms the gate electrode is not particularly limited, and examples thereof include: a metal such as gold, silver, aluminum, copper, chromium, nickel, cobalt, titanium, platinum, magnesium, calcium, barium, or sodium; a conductive oxide such as $InO_2$, $SnO_2$, or indium tin oxide (ITO); a conductive polymer such as polyaniline, polypyrrole, polythiophene, polyacetylene, or polydiacetylene; a semiconductor such as silicon, germanium, or gallium-arsenic; and a carbon material such as fullerene, carbon nanotube, or graphite. Among these, the metal is preferable, and silver or aluminum is more preferable.

The thickness of the gate electrode is not particularly limited and is preferably 20 to 200 nm.

The gate electrode may function as the substrate such as a silicon substrate. In this case, the substrate is not necessarily provided.

A method of forming the gate electrode is not particularly limited, and examples thereof include a method of performing vacuum deposition (hereinafter, simply referred to as "vapor deposition") or sputtering on the substrate using the above-described electrode material and a method of applying or printing an electrode-forming composition including the above-described electrode material. In addition, in a case where an electrode is patterned, examples of a patterning method include a printing method such as ink jet printing, screen printing, offset printing, or relief printing (flexographic printing); a photolithography method, and a mask deposition method.

—Gate Insulating Layer—

The gate insulating layer is not particularly limited as long as it is an insulating layer provided between the gate electrode and the organic semiconductor layer, and may have a single-layer structure or a multi-layer structure.

It is preferable that the gate insulating layer is formed of an insulating material, and preferable examples of the insulating material include an organic material such as an organic polymer and an inorganic material such as an inorganic oxide. From the viewpoint of handleability, in a case where a plastic substrate or a glass substrate is used, it is preferable that an organic material is used.

The organic polymer, the inorganic oxide, or the like is not particularly limited as long as it has insulating characteristics, and an organic polymer or an inorganic oxide with which a thin film, for example, a thin film having a thickness of 1 µm or less can be formed is preferable.

As the organic polymer or the inorganic oxide, one kind may be used alone, and two or more kinds may be used in combination. In addition, the gate insulating layer may be a hybrid layer formed of a mixture of the organic polymer and the inorganic oxide described below.

The organic polymer is not particularly limited, and examples thereof include: a poly(meth)acrylate such as polyvinyl phenol, polystyrene (PS), or polymethyl methacrylate; a cyclic fluoroalkyl polymer such as polyvinyl alcohol, polyvinyl chloride (PVC), polyvinylidene fluoride (PVDF), polytetrafluoroethylene (PTFE), or CYTOP; a polyorganosiloxane such as polycycloolefin, polyester, polyethersulfone, polyether ketone, polyimide, poly(meth) acrylic acid, polybenzoxazole, an epoxy resin, or polydimethylsiloxane (PDMS); polysilsesquioxane; and butadiene rubber. In addition to the above-described examples, a thermosetting resin such as a phenolic resin, a novolac resin, a cinnamate resin, an acrylic resin, or a polyparaxylylene resin may also be used.

The organic polymer can also be used in combination with a compound having a reactive substituent such as an alkoxysilyl group, a vinyl group, an acryloyloxy group, an epoxy group, or a methylol group.

In a case where the gate insulating layer is formed of the organic polymer, it is preferable that the organic polymer is crosslinked and cured, for example, in order to improve solvent resistance or insulation resistance of the gate insulating layer. It is preferable that crosslinking is performed by generating an acid or a radical using either or both light and heat.

In a case where the organic polymer is crosslinked by a radical, as a radical generator that generates a radical using light or heat, for example, a thermal polymerization initiator (H1) and a photopolymerization initiator (H2) described in paragraphs "0182" to "0186" of JP2013-214649A, a photoradical generator described in paragraphs "0046" to "0051" of JP2011-186069A, or a photoradical polymerization initiator described in paragraphs "0042" to "0056" of JP2010-285518A can be preferably used, the contents of which are preferably incorporated herein by reference.

In addition, "a compound (G) having a number-average molecular weight (Mn) of 140 to 5000, having a crosslinking functional group, and not having a fluorine atom" which is described in paragraphs "0167" to "0177" of JP2013-214649A can also be preferably used, the contents of which are incorporated herein by reference.

In a case where the organic polymer is crosslinked by an acid, as a photoacid generator that generates an acid using light, for example, a photocationic polymerization initiator described in paragraphs "0033" and "0034" of JP2010-285518A or an acid generator, in particular, a sulfonium salt or an iodonium salt described in paragraphs "0120" to "0136" of JP2012-163946A can be preferably used, the contents of which are preferably incorporated herein by reference.

As a thermal acid generator (catalyst) that generates an acid using heat, for example, a thermal cationic polymerization initiator, in particular, an onium salt or the like described in paragraphs "0035" to "0038" of JP2010-285518A or a catalyst, in particular, a sulfonic acid or a sulfonic acid amine salt described in paragraphs "0034" and "0035" of JP2005-354012A can be preferably used, the contents of which are preferably incorporated herein by reference.

In addition, a crosslinking agent, in particular, a bifunctional or higher epoxy compound or oxetane compound described in paragraphs "0032" and "0033" of JP2005-354012A, a crosslinking agent, in particular, a compound having two or more crosslinking groups at least one of which is a methylol group or an NH group described in paragraphs "0046" to "0062" of JP2006-303465A, or a compound having two or more hydroxymethyl groups or alkoxymethyl groups in a molecule described in paragraphs "0137" to "0145" of JP2012-163946A is also preferably used, the contents of which are preferably incorporated herein by reference.

Examples of forming the gate insulating layer using the organic polymer include a method of applying and curing the organic polymer. A coating method is not particularly limited, and examples thereof include the above-described printing methods. Among these, a wet coating method such as a microgravure coating method, a dip coating method, a screen coating printing method, a die coating method, or a spin coating method is preferable.

The inorganic oxide is not particularly limited, and examples thereof include: an oxide such as silicon oxide, silicon nitride ($SiN_Y$), hafnium oxide, titanium oxide, tantalum oxide, aluminum oxide, niobium oxide, zirconium oxide, copper oxide, or nickel oxide; a compound having a perovskite structure such as $SrTiO_3$, $CaTiO_3$, $BaTiO_3$, $MgTiO_3$, or $SrNb_2O_6$; and a composite oxide or a mixture thereof. Examples of the silicon oxide include silicon oxide ($SiO_x$), boron phosphorus silicon glass (BPSG), phosphorus silicon glass (PSG), borosilicate glass (BSG), arsenic silicate glass (AsSG), lead silicate glass (PbSG), silicon nitride oxide (SiON), spin-on-glass (SOG), and a low dielectric constant $SiO_2$ material (for example, polyarylether, a cycloperfluorocarbon polymer, benzocyclobutene, a cyclic fluororesin, polytetrafluoroethylene, fluorinated aryl ether, fluorinated polyimide, amorphous carbon, or organic SOG).

A method of forming the gate insulating layer using the inorganic oxide is not particularly limited. For example, a vacuum film formation method such as a vacuum deposition method, a sputtering method, or an ion plating or chemical vapor deposition (CVD) method can be used. In addition, the film formation may be assisted with plasma using predetermined gas, an ion gun, or a radical gun.

In addition, the gate insulating layer may also be formed by causing a precursor corresponding to each of metal oxides, specifically, a metal halide such as a chloride or a bromide, a metal alkoxide, a metal hydroxide, or the like is to react with an acid such as hydrochloric acid, sulfuric acid, or nitric acid or a base such as sodium hydroxide or potassium hydroxide in alcohol or water for hydrolysis. In a case where the solution-based process is used, the wet coating method can be used.

In addition to the above-described method, the gate insulating layer can also be formed optionally using a combination of any one of a lift-off method, a sol-gel method, an electrodeposition method, or a shadow mask method with a patterning method can also be optionally used.

The gate insulating layer may undergo a surface treatment such as a corona treatment, a plasma treatment, or an ultraviolet (UV)/ozone treatment.

It is preferable that a surface roughness of the gate insulating film is not high. It is preferable that an arithmetic average roughness Ra or a root-mean-square roughness $R_{ms}$ of the gate insulating layer surface is 0.5 nm or lower. In a case where a surface treatment is performed, a surface treatment that treats the insulating film surface not to be rough is preferable.

The thickness of the gate insulating layer is not particularly limited and is preferably 100 to 1000 nm.

—Source Electrode and Drain Electrode—

In the transistor according to the embodiment of the present invention, the source electrode is an electrode into which charges flow from the outside through a wiring. In addition, the drain electrode is an electrode from which charges flow to the outside through a wiring.

As a material which forms the source electrode and the drain electrode, the same electrode material as that of the gate electrode can be used. Among these, a metal is preferable, and gold or silver is more preferable. In addition, it is preferable that a charge injection layer is provided between the metal and the organic semiconductor so as to promote charge injection from the source into the organic semiconductor and to improve mobility.

The thickness of each of the source electrode and the drain electrode is not particularly limited and is preferably 1 nm or more and more preferably 10 nm or more. In addition, the thickness of each of the source electrode and the drain electrode is preferably 500 nm or less and more preferably 300 nm or less.

An interval (gate length) between the source electrode and the drain electrode can be appropriately determined and is, for example, preferably 200 μm or less and more preferably 100 μm or less. In addition, the gate width can be appropriately determined and is, for example, preferably 10 μm or more and more preferably 50 μm or more.

A method of forming the source electrode and the drain electrode is not particularly limited, and examples thereof include a method of performing vacuum deposition or sputtering using the electrode material on the substrate on which the gate electrode and the gate insulating film are formed and a method of applying or printing an electrode-forming composition to or on the substrate. In a case where the source electrode and the drain electrode are patterned, a patterning method thereof is the same as that of the gate electrode.

—Organic Semiconductor Layer—

In the transistor according to the embodiment of the present invention, the organic semiconductor layer can be formed by vapor deposition as described above.

(Sealing Layer)

In the transistor according to the embodiment of the present invention, it is preferable that the sealing layer is provided on the outermost layer from the viewpoint of durability. For the sealing layer, a sealing agent (sealing layer-forming composition) that is typically used in the organic semiconductor transistor can be used.

The thickness of the sealing layer is not particularly limited and is preferably 0.1 to 10 μm.

(Bottom Gate-Top Contact Type Organic Semiconductor Transistor)

Figure 2:
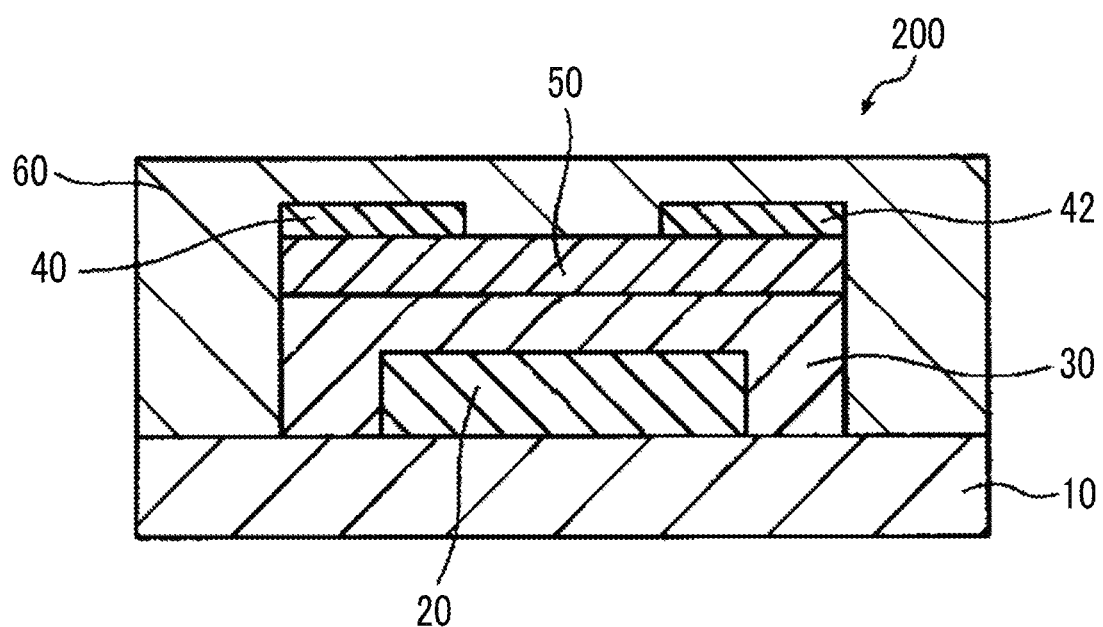
FIG. 2 is a schematic cross-sectional view showing one aspect of a bottom gate-top contact type organic semiconductor transistor as an example of the organic semiconductor transistor according to the present invention.

FIG. 2 is a schematic cross-sectional view showing a bottom gate-top contact type organic semiconductor transistor 200 as an example of the transistor according to the embodiment of the present invention.

As shown in FIG. 2, the organic semiconductor transistor 200 includes the substrate 10, the gate electrode 20, the gate insulating layer (film) 30, the organic semiconductor layer (film) 50, the source electrode 40 and the drain electrode 42, and the sealing layer 60 in this order.

The organic semiconductor transistor 200 is the same as the organic semiconductor transistor 100 except for the layer configuration (stack aspect). Accordingly, the details of the substrate, the gate electrode, the gate insulating layer, the source electrode, the drain electrode, the organic semiconductor layer, and the sealing layer are the same as those of the bottom gate-bottom contact type organic TFT, and thus the description thereof will not be repeated.

In the transistor according to the embodiment of the present invention, the performance and characteristics of the organic semiconductor layer (microcrystalline phase) are stably maintained even after patterning, a heat treatment, or the like during manufacturing of the transistor, and a variation in performance between transistor elements is significantly suppressed. In addition, the absolute value of a threshold voltage is low, and power consumption is also suppressed.

A method of manufacturing an organic semiconductor transistor according to the embodiment of the present invention (hereinafter, also referred to as "manufacturing method according to the embodiment of the present invention") includes vapor-depositing the organic semiconductor compound according to the present invention to form an organic semiconductor layer. It is also preferable that the organic semiconductor compound according to the present invention is vapor-deposited in a desired pattern shape through a mask. In addition, it is also preferable that the manufacturing method according to the embodiment of the present invention includes forming the microcrystalline film according to the embodiment of the present invention and patterning the formed microcrystalline film to form an organic semiconductor layer. For example, the manufacturing method according to the embodiment of the present invention may include vapor-depositing the organic semiconductor compound on the gate insulating layer (in the case of the top contact type) or vapor-depositing the organic semiconductor compound according to the embodiment of the present invention so as to cover the gate insulating layer and the source electrode and the drain electrode formed on the gate insulating layer (in the case of the bottom contact type) to form a microcrystalline film, and patterning the microcrystalline film to form an organic semiconductor layer of an organic semiconductor transistor. This patterning is performed by etching the organic semiconductor film or by scribing the organic semiconductor around a transistor-forming region.

In the manufacturing method according to the embodiment of the present invention, an organic semiconductor transistor in which an organic semiconductor layer is formed using the microcrystalline film according to the embodiment of the present invention is obtained, and cracks are not likely to be formed in the entire organic semiconductor layer (in particular, a channel region) although the organic semiconductor film is patterned after the formation. In the obtained transistor, a variation in performance between elements can be highly suppressed.

EXAMPLES

The present invention will be described in more detail using Examples, but the present invention is not limited to the following Examples.

[Synthesis Example 1] Synthesis of Compound 1

In the following reaction scheme, Bu represents butyl, Et represents ethyl, THF represents tetrahydrofuran, DMF represents N,N-dimethylformamide, TMP represents tetramethylpiperidine, and dppf represents 1,1'-bis(diphenylphosphino)ferrocene.

Synthesis of Intermediate 1a

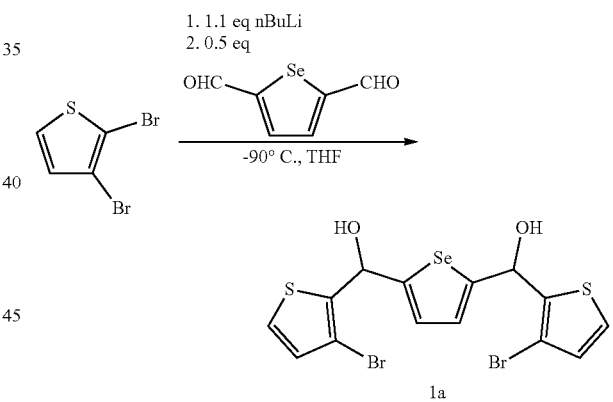

A 2,3-dibromothiophene n-butyllithium solution (15.9 g, 65.8 mmol) was dissolved in 120 ml of diethyl ether, and n-butyllithium (1.6 M solution) was added dropwise to the solution while stirring the solution at −90° C. After 30 minutes, a solution in which 2,5-selenophene dicarboxaldehyde (6.00 g, 32.1 mmol) was dissolved in 50 ml of tetrahydrofuran was added dropwise, was stirred at −78° C. for 20 minutes, and then was heated to room temperature. The reaction solution was quenched with water, and the organic layer was extracted with diethyl ether and was dried with magnesium sulfate. After concentration with an evaporator, an intermediate 1a (12.9 g) as a brown oily target material was obtained. A coarse body of the obtained target material was used for the next reaction without being purified.

$^1$H-NMR (400 MHz, CDCl$_3$) δ: 7.28 (d, J=5.2 Hz, 2H), 7.04 (d, J=5.2 Hz, 2H), 6.93 (d, J=5.2 Hz, 2H), 6.31 (s, 2H)

Synthesis of Intermediate 2a

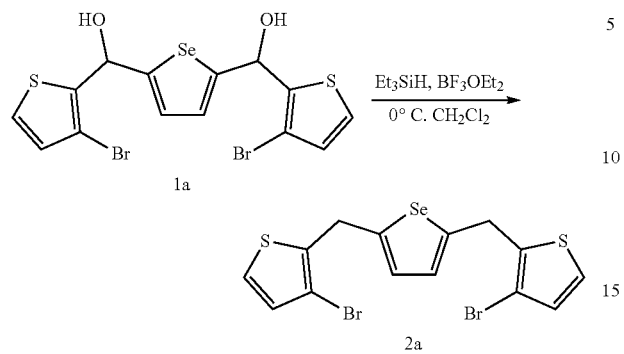

The intermediate 1a (12.9 g) and triethylsilane (15.4 ml, 96.2 mmol) were dissolved in 70 ml of dichloromethane, and the solution was cooled to 0° C. Next, boron trifluoride etherate (11.9 ml, 96.2 mmol) was added dropwise to the solution and was stirred for 30 minutes. Next, the solution was quenched with water, the organic layer was extracted with ethyl acetate and was dried with magnesium sulfate. After concentration, the coarse body was purified by column chromatography (hexane:ethyl acetate=95:5). As a result, an intermediate 2a (9.20 g, 19.1 mmol, 60% yield for 2 steps) as a yellow oily target material was obtained.

$^1$H-NMR (400 MHz, CDCl$_3$) δ: 7.16 (d, J=5.2 Hz, 2H), 6.92 (d, J=5.2 Hz, 2H), 6.86 (s, 2H), 4.28 (s, 4H)

Synthesis of Intermediate 3a

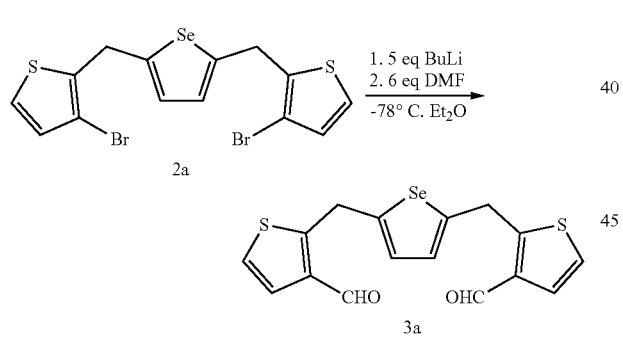

N-butyllithium (1.6 M solution) (58.5 ml, 93.5 mmol) was cooled to −78° C., a solution in which the intermediate 2a (9.00 g, 18.7 mmol) was dissolved in 240 ml of diethyl ether was added dropwise thereto, and the solution was stirred for 30 minutes. Next, N,N-dimethylformamide (8.7 ml, 112 mmol) was added dropwise. The solution was stirred at −78° C. for 20 minutes, was heated to room temperature, and was quenched with water. Next, the organic layer was extracted with diethyl ether and was dried with magnesium sulfate. After concentration, an intermediate 3a (6.50 g) as a red oily target material was obtained. A coarse body of the obtained target material was used for the next reaction without being purified.

$^1$H-NMR (400 MHz, CDCl$_3$) δ: 10.0 (s, 2H), 7.40 (d, J=4.8 Hz, 2H), 7.15 (d, J=4.8 Hz, 2H), 6.88 (s, 2H), 4.68 (s, 4H)

Synthesis of Intermediate 4a

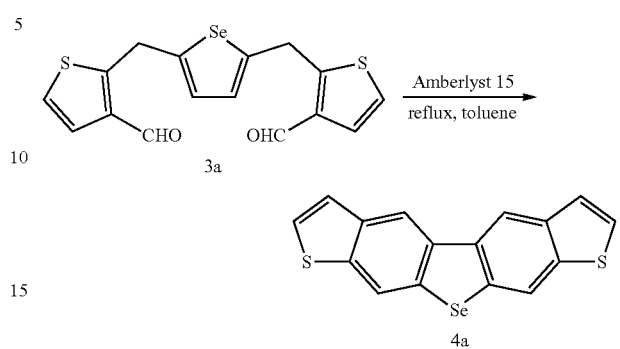

The intermediate 3a (6.50 g) was dissolved in 350 ml of toluene, AMBERLYST (registered trade name) 15 hydrogen form dry (15.0 g) was added thereto, and the solution was heated to reflux for 2 hours. The reaction solution was separated by filtration, and the filtrate was concentrated recrystallized with toluene/methanol, and purified by column chromatography (toluene). As a result, an intermediate 4a (2.35 g, 6.84 mmol, 36% yield for 2 steps) as a white solid target material was obtained.

$^1$H-NMR (400 MHz, CDCl$_3$) δ: 8.63 (s, 2H), 8.31 (d, J=0.8 Hz, 2H), 7.46 (m, 4H)

Synthesis of Intermediate 5a

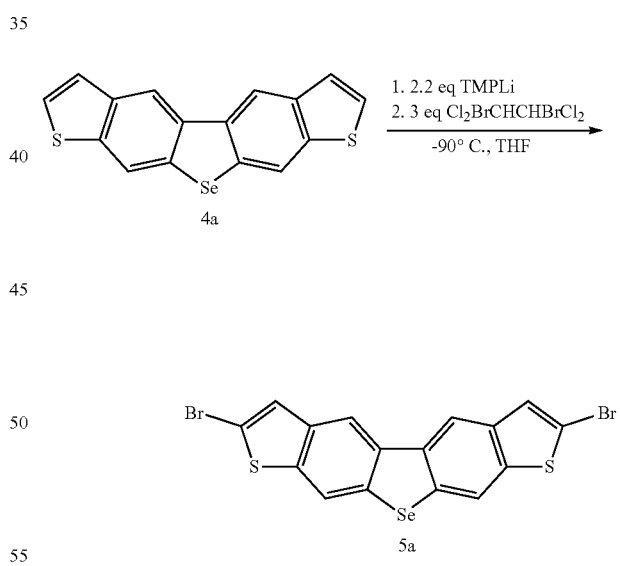

A mixed solution of the intermediate 4a (2.00 g, 5.83 mmol) and 58 ml of tetrahydrofuran was stirred at −90° C., 20 ml of a tetrahydrofuran solution of lithiumtetramethylpiperidine (12.8 mmol) was added dropwise, and the solution was stirred for 30 minutes. A solution in which dibromotetrachloroethane (5.69 g, 17.5 mmol) was dissolved in 20 ml of tetrahydrofuran was added dropwise to the reaction solution, and the solution was stirred at −78° C. for 20 minutes and was heated to room temperature. The reaction solution was quenched with water, and the organic layer was extracted with dichloromethane and was dried with magnesium sulfate. After concentration, the solution was recrystallized with tetrahydrofuran/methanol. As a result, an intermediate 5a (2.21 g, 4.41 mmol, 76% yield) as a white solid target material was obtained.

$^1$H-NMR (400 MHz, CDCl$_3$) δ: 8.46 (s, 2H), 8.16 (s, 2H), 7.45 (s, 2H)

Synthesis of Compound 1

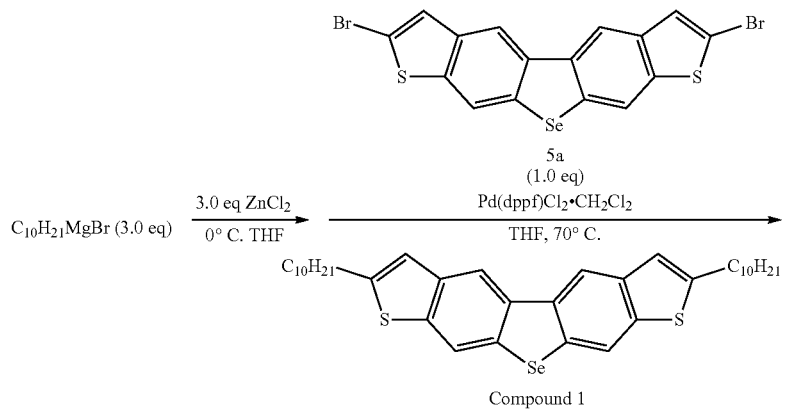

A zinc chloride (II) solution (1.0 mol/L, tetrahydrofuran solution, 1.50 ml) was added at 0° C. to an n-decyl magnesium bromide solution (1.0 mol/L, in diethylether, 1.50 ml, 1.50 mmol) used as a reactant. Next, the solution was stirred for 15 minutes, and the intermediate 5a (250 mg, 0.45 mmol) and a 1,1'-bis(diphenylphosphino) ferrocene dichloro palladium (II) dichloromethane adduct (20.2 mg, 0.025 mmol) were added thereto. The reaction solution was stirred at 70° C. for 1 hour, was concentrated, and was purified by column chromatography (hexane/chloroform=95/5). As a result, a compound 1 (102 mg, 0.16 mmol, 33% yield) as a white solid target material was obtained.

$^1$H-NMR (400 MHz, CDCl$_3$) δ: 8.43 (s, 2H), 8.17 (s, 2H), 7.10 (s, 2H), 2.93 (t, J=7.6 Hz, 4H), 1.78 (quint, J=6.4 Hz, 4H), 1.46-1.27 (m, 28H), 0.88 (t, J=6.8 Hz, 6H)

[Synthesis Examples 2 to 108] Synthesis of Compounds 2 to 108

Under the same conditions as those of Synthesis Example 1, compounds 2 to 108 shown in tables below were synthesized referring to Examples of JP2015-195362A.

Figure 3:
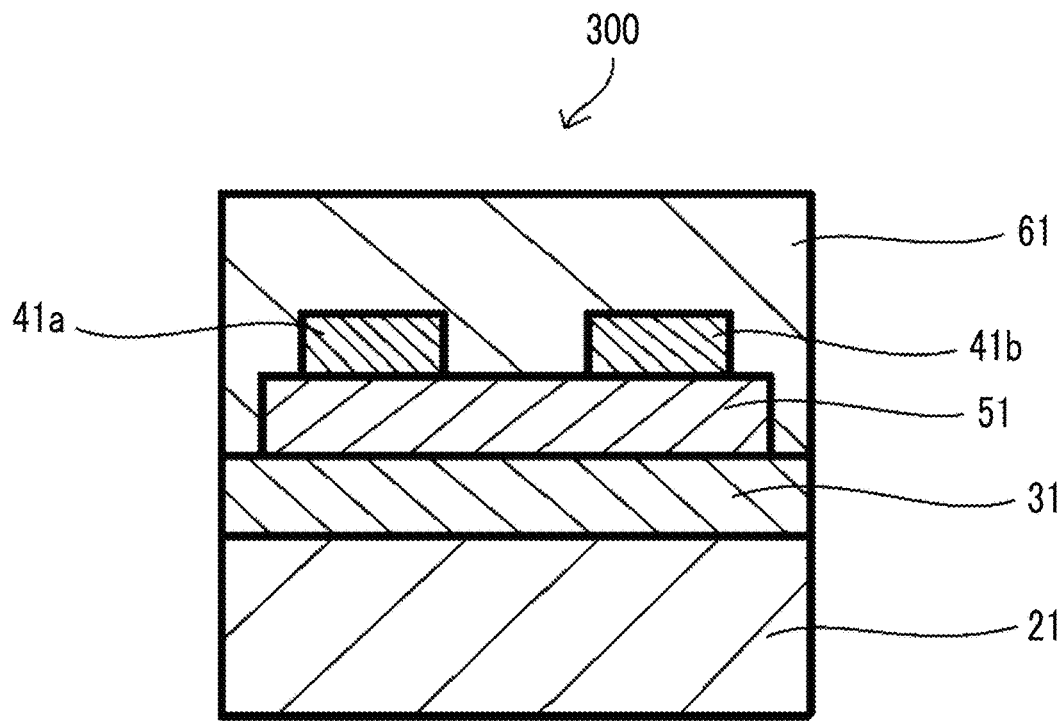
FIG. 3 is a schematic cross-sectional view showing another aspect of the bottom gate-top contact type organic semiconductor transistor as an example of the organic semiconductor transistor according to the present invention.

[Manufacturing Examples 1-1 to 1-108, Comparative Manufacturing Examples 1-1 to 1-4]
Manufacturing of Bottom Gate-Top Contact Type Organic Semiconductor Transistor A bottom gate-top contact type organic semiconductor transistor 300 shown in FIG. 3 was manufactured as follows.

<Gate Electrode and Gate Insulating Layer>

A conductive silicon substrate (gate electrode, 0.7 mm) on which a SiO$_2$ thermal oxide film (gate insulating layer, 350 nm) was formed was used. The surface of the SiO$_2$ thermal oxide film was treated with phenethyltrichlorosilane (β-PTS).

<Formation of Organic Semiconductor Film (Layer)>

Each of the compounds 1 to 108 and the comparative compounds 1 to 4 obtained in each of the synthesis examples was vacuum-deposited (substrate temperature: normal temperature, vacuum degree: $1 \times 10^{-5}$ to $1 \times 10^{-4}$ Pa) on the β-PTS-treated surface to form an organic semiconductor film (thickness: 30 nm).

<Formation of Source Electrode and Drain Electrode>

7,7,8,8-tetracyanoquinodimethane (manufactured by Tokyo Chemical Industry Co., Ltd.) and a gold electrode were vapor-deposited on the organic semiconductor layer through a mask to form a source electrode (thickness: 1.5 nm) and a drain electrode (thickness: 50 nm), respectively. This way, organic semiconductor transistors according to the present invention and comparative organic semiconductor transistors were manufactured.

<Patterning>

By scribing the vicinity of an organic semiconductor transistor-forming region with a needle, the organic semiconductor transistor-forming region and the other regions were separated from each other.

As manufacturing examples corresponding to the compounds 1 to 108, Manufacturing Examples 1-1 to 1-108 were used. As manufacturing examples corresponding to the comparative compounds 1 to 4, Comparative Manufacturing Examples 1-1 to 1-4 were used.

[Measurement Method and Evaluation Method]

(1) Analysis Using X-Ray Diffraction

The X-ray diffraction of the formed organic semiconductor film was evaluated. In each of the films, a peak corresponding to a crystalline structure was observed, and it was clarified that the obtained film was crystalline without being amorphous.

<Measurement of Crystal Domain Size of Organic Semiconductor Film>

(2) Observation with Polarizing Microscope

The formed organic semiconductor film was observed with a polarizing microscope. In a case where a domain having optical dichroism was able to be observed, the crystal domain size was determined to be more than 1 μm. In a case where a domain having optical dichroism was not able to be observed, the crystal domain size was determined to be 1 μm or less.

(3) Observation with AFM and Measurement of Crystal Domain Size

In a case where the crystal domain size was determined to be 1 μm or less in (1) above, the organic semiconductor film was observed with AFM (trade name, Dimension FastScan AFM, manufactured by Bruker Corporation). In a cross-sectional profile obtained using the AFM, a length divided as one gentle mountain under analysis conditions described below was set as a crystal domain size. That is, in the present invention, the crystal domain size refers to the size of one crystal domain. A crystal domain size being 1 nm to 100 nm represents that all the observed crystal domain sizes are in a range of 1 nm to 100 nm (likewise, a crystal domain size being 5 nm to 80 nm represents that all the observed crystal domain sizes are in a range of 5 nm to 80 nm).

Figure 5:
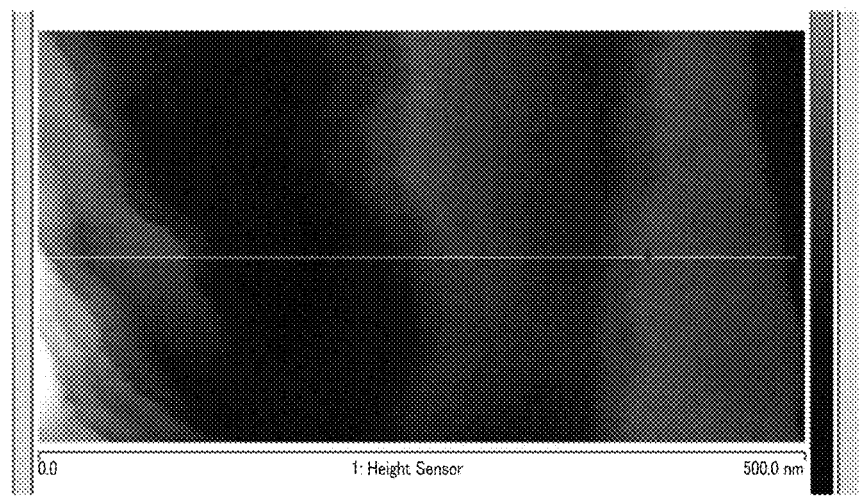
FIG. 5 is a diagram showing an example of a surface shape image obtained by observing a microcrystalline organic semiconductor film with an atomic force microscope (AFM).
Figure 6:
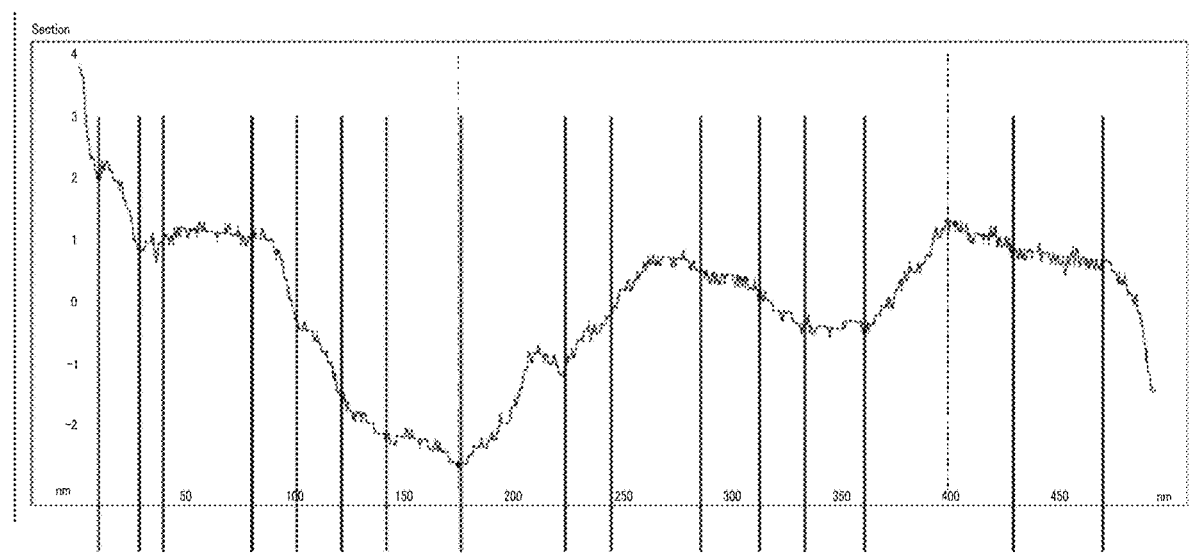
FIG. 6 is a diagram showing an example of a cross-sectional profile image obtained by observing a microcrystalline organic semiconductor film with an atomic force microscope (AFM), in which one length divided by vertical lines represents a crystal domain size.

The organic semiconductor film formed by vapor deposition of the compound 1 was observed with AFM, the obtained image is shown in FIG. 5, and a cross-sectional profile thereof is shown in FIG. 6. A length divided by vertical line in FIG. 6 is evaluated as a crystal domain size. Analysis conditions of the crystal domain size in FIG. 6 are as follows.

<Analysis Conditions of Crystal Domain Size>
Mode: tapping mode
Cantilever: NCH-10T (manufactured by Toyo Corporation)
Visual field: 500 nm×250 nm
Resolution: 1024×512

<Evaluation of Characteristics of Organic Semiconductor Transistor>

Regarding each of the manufactured organic semiconductor transistors, characteristics of the transistor in air were evaluated using a semiconductor characteristic evaluation device: 4155C (trade name, manufactured by Agilent Technologies Inc.).

Specifically, a voltage of −15 V was applied between the source electrode and the drain electrode of each of the organic thin film transistors, and a gate voltage was caused to vary in a range of +40 V to −40 V in a reciprocating manner. In this case, a carrier mobility μ (cm$^2$/Vs) and a threshold voltage $V_{th}$ (V) in a case the gate voltage was caused to vary in a range of +40 V to −40 V and a carrier mobility μ (cm$^2$/Vs) and a threshold voltage $V_{th}$ (V) in a case where the gate voltage was caused to vary in a range of −40 V to +40 V were calculated using the following expression indicating a drain current Id.

$$I_d = (w/2L)\mu C_i (V_g - V_{th})^2$$

In the expression, L represents the gate length, w represents the gate width, μ represents the carrier mobility, $C_i$ represents the volume of the gate insulating layer per unit area, $V_g$ represents the gate voltage, and $V_{th}$ represents a threshold voltage.

Regarding the organic semiconductor transistor in which the organic semiconductor layer was formed of each of the compounds, 100 samples were prepared (that is, 100 organic semiconductor transistors in which compounds forming the organic semiconductor layers were the same). Based on the characteristics of each of the 100 transistors, the performance of the transistor was evaluated based on the following evaluation standards.

(Evaluation Standards of Average Mobility)

The average carrier mobility of the 100 organic semiconductor transistors was obtained and was evaluated based on the following evaluation standards. The carrier mobility of one organic semiconductor transistor was the average value of the carrier mobility in a case where the gate voltage was swept from +40 V to −40 V and the carrier mobility in a case where the gate voltage was swept from −40 V to +40 V.

A: the average value of the carrier mobilities was 1 cm$^2$/Vs or higher

B: the average value of the carrier mobilities was 0.5 cm$^2$/Vs or higher and lower than 1 cm$^2$/Vs C: the average value of the carrier mobilities was 0.1 cm$^2$/Vs or higher and lower than 0.5 cm$^2$/Vs D: the average value of the carrier mobilities was 0.01 cm$^2$/Vs or higher and lower than 0.1 cm$^2$/Vs E: the average value of the carrier mobilities was lower than 0.01 cm$^2$/Vs (Evaluation Standards of Variation in Mobility)

Based on a coefficient of variation obtained from the following expression, a variation in carrier mobility was evaluated by the following evaluation standards.

Coefficient of Variation (%)=100×[Standard Deviation of Carrier Mobilities of 100 Organic Semiconductor Transistors]/[Average Value of Carrier Mobilities of 100 Organic Semiconductor Transistors] The carrier mobility of one organic semiconductor transistor was the average value of the carrier mobility in a case where the gate voltage was swept from +40 V to −40 V and the carrier mobility in a case where the gate voltage was swept from −40 V to +40 V.

A: the coefficient of variation was lower than 10%

B: the coefficient of variation was 10% or higher and lower than 20%

C: the coefficient of variation was 20% or higher and lower than 30%

D: the coefficient of variation was 30% or higher and lower than 40%

E: the coefficient of variation was 40% or higher (Yield)

Regarding the organic semiconductor transistor in which the organic semiconductor layer was formed of each of the compounds, 100 samples were prepared. By using the number of defective products having a carrier mobility of lower than 0.01 cm$^2$/Vs among the 100 organic semiconductor transistors as an index, the yield was evaluated based on the following evaluation standards.

The carrier mobility of one organic semiconductor transistor was the average value of the carrier mobility in a case where the gate voltage was swept from +40 V to −40 V and the carrier mobility in a case where the gate voltage was swept from −40 V to +40 V.

A: the number of defective products was 0

B: the number of defective products was 1 or 2

C: the number of defective products was 3 to 5

D: the number of defective products was 6 to 10

E: the number of defective products was 11 or more ($V_{th}$ Shift)

Regarding each of the 100 organic semiconductor transistors, the average of $V_{th}$ in a case where the gate voltage was swept from +40 V to −40 V and $V_{th}$ in a case where the gate voltage was swept from −40 V to +40 V was obtained as an average $V_{th}$. The average value (referred to as "$V_{th}^{100}$") of the respective average Vth values of the 100 organic semiconductor transistors was obtained (that is, the average value of the 100 average Vth values was calculated) and was evaluated based on the following evaluation standards.

A: the absolute value of $V_{th}^{100}$ was lower than 3 V

B: the absolute value of $V_{th}^{100}$ was 3 V or higher and lower than 5 V

C: the absolute value of $V_{th}^{100}$ was 5 V or higher and lower than 10 V

D: the absolute value of $V_{th}^{100}$ was 10 V or higher and lower than 15 V

E: the absolute value of $V_{th}^{100}$ was 15 V or higher (Evaluation of Hysteresis)

The absolute value of a difference between $V_{th}$ in a case where the gate voltage was swept from +40 V to −40 V and $V_{th}$ in a case where the gate voltage was swept from −40 V to +40 V was defined as hysteresis. The average value of the hysteresis values of the 100 organic semiconductor transistors was obtained and was evaluated based on the following evaluation standards.

A: the average hysteresis was lower than 3 V

B: the average hysteresis was 3 V or higher and lower than 5 V

C: the average hysteresis was 5 V or higher and lower than 10 V

D: the average hysteresis was 10 V or higher and lower than 15 V

E: the average hysteresis was 15 V or higher

The evaluation results of Manufacturing Examples 1 to 108 and Comparative Manufacturing Examples 1 to 4 are shown in tables below.

In Manufacturing Examples 1 to 108 and Comparative Manufacturing Examples 1 to 4, all the crystal domain sizes of the organic semiconductor layers were in a range of 5 nm to 80 nm.

TABLE 61

| | | Average Mobility | Variation in Mobility | Yield | $V_{th}$ Shift | Hysteresis |
|---|---|---|---|---|---|---|
| Compound 1 | | A | A | A | A | A |
| Compound 2 | | B | A | A | B | A |
| Compound 3 | | A | A | A | A | A |
| Compound 4 | | A | A | A | A | A |
| Compound 5 | | A | A | A | A | A |
| Compound 6 | | A | A | A | A | A |
| Compound 7 | | A | B | A | B | A |
| Compound 8 | | A | B | A | B | A |

TABLE 61-continued
| | | Average Mobility | Variation in Mobility | Yield | $V_{th}$ Shift | Hysteresis |
|---|---|---|---|---|---|---|
| Compound 9 | 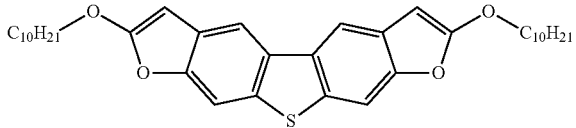 | B | A | A | B | B |
| Compound 10 | 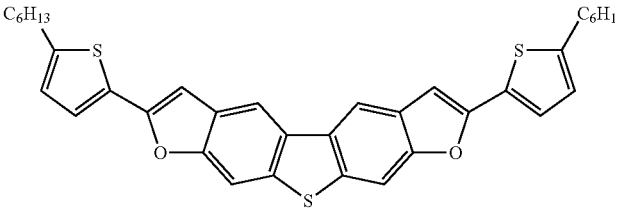 | A | B | A | B | A |
| Compound 11 | 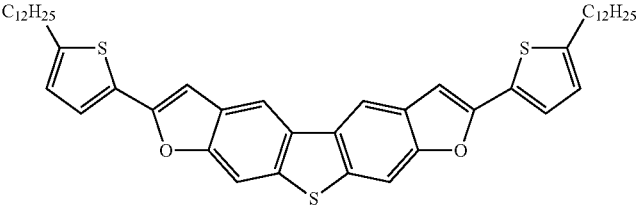 | A | B | A | B | A |
TABLE 62
| | | Average Mobility | Variation in Mobility | Yield | $V_{th}$ Shift | Hysteresis |
|---|---|---|---|---|---|---|
| Compound 12 | 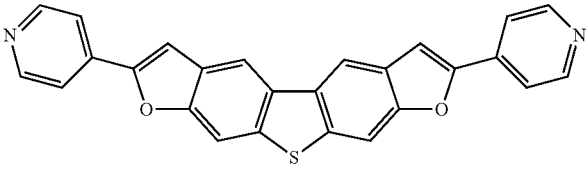 [SMILES: c1cc(-c2cc3cc4c(cc3o2)sc2cc3oc(-c5ccncc5)cc3cc24)ccn1] | A | B | A | B | A |
| Compound 13 | 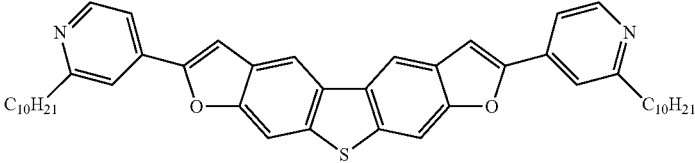 | A | B | A | B | A |
| Compound 14 | 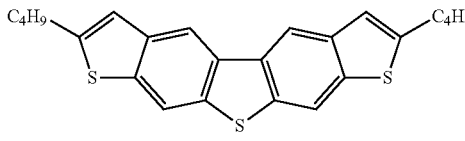 | A | A | A | A | A |
| Compound 15 | 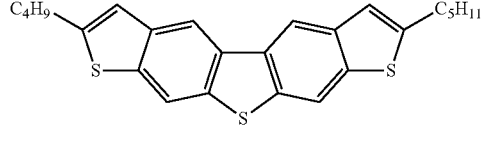 | A | A | A | A | A |
| Compound 16 | 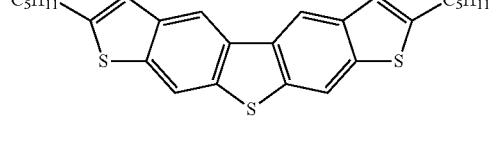 | A | A | A | A | A |

TABLE 62-continued

| | | Average Mobility | Variation in Mobility | Yield | $V_{th}$ Shift | Hysteresis |
|---|---|---|---|---|---|---|
| Compound 17 | [structure with C$_6$H$_{13}$ groups] | A | A | A | A | A |
| Compound 18 | [structure with C$_4$H$_9$ groups] | A | A | A | A | A |
| Compound 19 | [structure with C$_{10}$H$_{21}$ groups] | A | A | A | A | A |
| Compound 20 | [structure with thienothiophene groups] | A | A | A | B | A |
| Compound 21 | [structure with pyridyl groups] | A | A | A | B | A |
| Compound 22 | [structure with C$_{10}$H$_{21}$-furan groups] | B | B | A | B | A |

TABLE 63

| | | Average Mobility | Variation in Mobility | Yield | $V_{th}$ Shift | Hysteresis |
|---|---|---|---|---|---|---|
| Compound 23 | | B | B | A | A | A |
| Compound 24 | | B | B | A | B | A |
| Compound 25 | | C | B | B | B | B |
| Compound 26 | | B | B | B | A | A |
| Compound 27 | | B | B | B | A | A |
| Compound 28 | | B | B | B | A | A |
| Compound 29 | | B | B | B | A | A |
| Compound 30 | | A | B | A | B | A |
| Compound 31 | | B | B | A | B | B |

TABLE 63-continued

| | | Average Mobility | Variation in Mobility | Yield | $V_{th}$ Shift | Hysteresis |
|---|---|---|---|---|---|---|
| Compound 32 | [structure] | A | B | A | B | A |
| Compound 33 | [structure] | A | B | A | B | A |

TABLE 64

| | | Average Mobility | Variation in Mobility | Yield | $V_{th}$ Shift | Hysteresis |
|---|---|---|---|---|---|---|
| Compound 34 | [structure] | B | B | B | B | A |
| Compound 35 | [structure] | B | B | B | B | A |
| Compound 36 | [structure] | B | B | B | B | B |
| Compound 37 | [structure] | B | A | A | A | A |
| Compound 38 | [structure] | C | B | B | B | B |

TABLE 64-continued

| | | Average Mobility | Variation in Mobility | Yield | $V_{th}$ Shift | Hysteresis |
|---|---|---|---|---|---|---|
| Compound 39 | (structure) | B | B | B | A | A |
| Compound 40 | (structure) | B | B | B | A | A |
| Compound 41 | (structure) | B | B | B | A | A |
| Compound 42 | (structure) | B | A | B | A | A |
| Compound 43 | (structure) | A | A | A | A | A |
| Compound 44 | (structure) | B | A | A | B | A |

TABLE 65

| | | Average Mobility | Variation in Mobility | Yield | $V_{th}$ Shift | Hysteresis |
|---|---|---|---|---|---|---|
| Compound 45 | (structure) | B | B | B | B | A |
| Compound 46 | (structure) | C | B | B | B | B |

TABLE 65-continued

| | | Average Mobility | Variation in Mobility | Yield | $V_{th}$ Shift | Hysteresis |
|---|---|---|---|---|---|---|
| Compound 47 | C₁₄H₂₉–[structure with Se, S]–C₁₄H₂₉ | A | B | A | A | A |
| Compound 48 | H₃C–[structure with O, N, S]–CH₃ | A | A | A | B | A |
| Compound 49 | phenyl–[structure with O, N, S]–C₅H₁₁ | B | B | B | B | B |
| Compound 50 | H₃C–[structure with S, N, S]–CH₃ | B | B | B | A | A |
| Compound 51 | H₃C–[structure with S, N, S, CH₃]–CH₃ | C | B | B | A | A |
| Compound 52 | H₃C–[structure with Se, S]–CH₃, C₆H₁₃ substituents | C | B | B | A | A |
| Compound 53 | H₃C–[structure with Se, S, CH₃ groups]–CH₃ | C | B | B | B | B |
| Compound 54 | C₁₄H₂₉–[structure with Se, N, S]–C₁₄H₂₉ | B | B | B | A | A |
| Compound 55 | C₃H₇–CH=CH–[structure with Se, N, S]–CH=CH–C₃H₇ | C | B | B | A | A |

TABLE 66

| | | Average Mobility | Variation in Mobility | Yield | $V_{th}$ Shift | Hysteresis |
|---|---|---|---|---|---|---|
| Compound 56 | | B | B | B | B | B |
| Compound 57 | | C | C | B | C | B |
| Compound 58 | | B | B | B | B | B |
| Compound 59 | | B | B | B | A | A |
| Compound 60 | | B | B | B | A | A |
| Compound 61 | | C | B | B | A | A |
| Compound 62 | | A | A | A | A | A |
| Compound 63 | | A | A | A | B | A |
| Compound 64 | | A | B | A | B | B |

TABLE 66-continued

| | | Average Mobility | Variation in Mobility | Yield | $V_{th}$ Shift | Hysteresis |
|---|---|---|---|---|---|---|
| Compound 65 | | C | C | B | C | C |
| Compound 66 | | C | B | B | B | B |

TABLE 67

| | | Average Mobility | Variation in Mobility | Yield | $V_{th}$ Shift | Hysteresis |
|---|---|---|---|---|---|---|
| Compound 67 | | B | B | B | B | B |
| Compound 68 | | A | B | A | A | A |
| Compound 69 | | B | B | B | A | A |
| Compound 70 | | B | B | B | A | A |
| Compound 71 | | A | B | B | A | A |
| Compound 72 | | B | B | C | B | B |

TABLE 67-continued

| | | Average Mobility | Variation in Mobility | Yield | $V_{th}$ Shift | Hysteresis |
|---|---|---|---|---|---|---|
| Compound 73 | *structure* | B | B | C | B | B |
| Compound 74 | *structure* | C | B | C | B | B |
| Compound 75 | *structure* | C | C | C | C | C |
| Compound 76 | *structure* | C | C | C | C | C |
| Compound 77 | *structure* | C | C | C | C | C |

TABLE 68

| | | Average Mobility | Variation in Mobility | Yield | $V_{th}$ Shift | Hysteresis |
|---|---|---|---|---|---|---|
| Compound 78 | *structure* | B | B | A | A | A |
| Compound 79 | *structure* | C | B | B | A | A |

TABLE 68-continued

| | | Average Mobility | Variation in Mobility | Yield | $V_{th}$ Shift | Hysteresis |
|---|---|---|---|---|---|---|
| Compound 80 | | B | C | C | B | A |
| Compound 81 | | B | B | B | A | A |
| Compound 82 | | B | B | B | A | A |
| Compound 83 | | B | B | B | B | A |
| Compound 84 | | C | B | B | A | A |
| Compound 85 | | C | C | C | C | C |
| Compound 86 | | C | B | B | A | B |
| Compound 87 | | C | C | C | C | C |
| Compound 88 | | B | B | B | B | B |

TABLE 69

| | | Average Mobility | Variation in Mobility | Yield | $V_{th}$ Shift | Hysteresis |
|---|---|---|---|---|---|---|
| Compound 89 | [structure] | C | C | B | B | B |
| Compound 90 | [structure] | B | B | B | A | A |
| Compound 91 | [structure] | B | B | B | A | A |
| Compound 92 | [structure] | B | B | B | A | A |
| Compound 93 | [structure] | C | B | B | B | A |
| Compound 94 | [structure] | C | C | C | B | B |
| Compound 95 | [structure] | B | B | B | B | B |
| Compound 96 | [structure] | B | B | B | B | B |

TABLE 69-continued

| | | Average Mobility | Variation in Mobility | Yield | $V_{th}$ Shift | Hysteresis |
|---|---|---|---|---|---|---|
| Compound 97 | [structure] | B | B | B | C | B |
| Compound 98 | [structure] | B | B | B | B | B |
| Compound 99 | [structure] | B | B | B | C | B |

TABLE 70

| | | Average Mobility | Variation in Mobility | Yield | $V_{th}$ Shift | Hysteresis |
|---|---|---|---|---|---|---|
| Compound 100 | [structure] | C | C | C | B | B |
| Compound 101 | [structure] | C | C | C | B | B |
| Compound 102 | [structure] | B | B | B | B | B |

TABLE 70-continued

| | | Average Mobility | Variation in Mobility | Yield | $V_{th}$ Shift | Hysteresis |
|---|---|---|---|---|---|---|
| Compound 103 | | B | A | A | A | A |
| Compound 104 | | B | A | A | A | A |
| Compound 105 | | A | B | A | B | A |
| Compound 106 | | A | B | A | B | A |
| Compound 107 | | A | A | A | B | A |
| Compound 108 | | A | B | A | B | A |
| Comparative Compound 1 | | D | C | D | B | B |
| Comparative Compound 2 | | E | D | E | B | B |

TABLE 70-continued

|  |  | Average Mobility | Variation in Mobility | Yield | $V_{th}$ Shift | Hysteresis |
|---|---|---|---|---|---|---|
| Comparative Compound 3 | 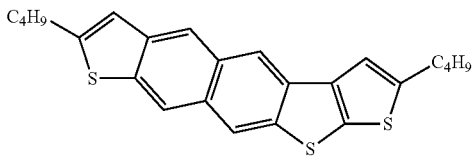 | E | C | E | B | B |
| Comparative Compound 4 | 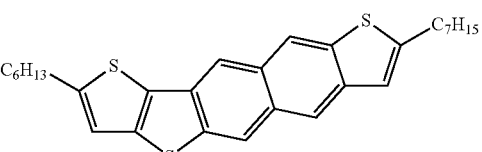 | E | C | E | B | B |

As shown in the tables, in the organic semiconductor transistors according to Comparative Manufacturing Examples 1-1 to 1-4 in which the organic semiconductor layers were formed using the comparative compounds 1 to 4, respectively, that were not the compounds defined by the present invention, the average mobility was low, and the yield was also poor.

On the other hand, in the organic semiconductor transistors according to Manufacturing Examples 1-1 to 1-108 in which the organic semiconductor film according to the present invention was used as the organic semiconductor layer, the average mobility was excellent, the variation in mobility was small, and the yield was also excellent. In addition, the $V_{th}$ shift was also suppressed to be low as a whole, and the evaluation of hysteresis was also excellent. This way, it can be seen that, in the organic semiconductor transistor according to the embodiment of the present invention, the mobility is excellent, a variation in performance between elements is small, and power consumption is small.

[Comparative Manufacturing Example 1-5]
Manufacturing of Bottom Gate-Top Contact Type Organic Semiconductor Transistor An organic semiconductor transistor was manufactured under the same conditions as those of Manufacturing Example 1-1, except that the formation of the organic semiconductor film was changed as follows.
<Formation of Organic Semiconductor Film (Layer)>
The compound 1 was dissolved in anisole to prepare a coating solution including 0.1 mass % of the compound 1. Using this coating solution, the organic semiconductor film (thickness: 30 nm) was formed on the β-PTS-treated surface with the same method as a method (edge casting method) described in paragraphs "0187" and "0188" of JP2015-195362A.

The crystalline structure of the formed organic semiconductor film was able to be observed with a polarizing microscope. The crystal domain size of the organic semiconductor film was much more than 10 μm, and a crystal domain having a size of 1 mm or more was also observed.

Regarding the organic semiconductor transistor according to Comparative Manufacturing Example 1-5, the average mobility, the variation in mobility, the yield, the $V_{th}$ shift, and the hysteresis were evaluated using the above-described evaluation methods. The results are shown in the following table as compared to the evaluation results of the organic semiconductor transistor according to Manufacturing Example 1-1.

TABLE 71

|  | Compound | Average Mobility | Variation in Mobility | Yield | Vth Shift | Hysteresis |
|---|---|---|---|---|---|---|
| Manufacturing Example 1-1 | Compound 1 | A | A | A | A | A |
| Comparative Manufacturing Example 1-5 | Compound 1 | A | C | D | D | B |

As shown in the table, in the organic semiconductor transistor according to Comparative Manufacturing Example 1-5 in which the organic semiconductor film was formed using a solution process and the crystal domain size of the organic semiconductor film was more than the range defined by the present invention, the variation in mobility was larger than that of the organic semiconductor transistor according to Manufacturing Example 1-1. In the organic semiconductor transistor according to Comparative Manufacturing Example 1-5, an element having a high carrier mobility was obtained; however, an element having a significantly low carrier mobility appeared with a high probability, and the yield also deteriorated. In addition, the $V_{th}$ shift was high, the hysteresis was also poor, and the result was also poor from the viewpoint of power consumption.

Organic semiconductor transistors were manufactured under the same conditions as those of Comparative Manufacturing Example 1-5, except that the compounds 2 to 108 were used instead of the compound 1. In a case where the performances of the organic semiconductor transistors were compared to the performance of the organic semiconductor transistors according to Manufacturing Examples 1-2 to 1-108 in which the compounds corresponding to Manufacturing Examples 1-2 to 1-108 were used (that is, compounds forming the organic semiconductor layers were the same), all the results regarding the variation in mobility, the yield, the $V_{th}$ shift, and the hysteresis were poor.

Figure 4:
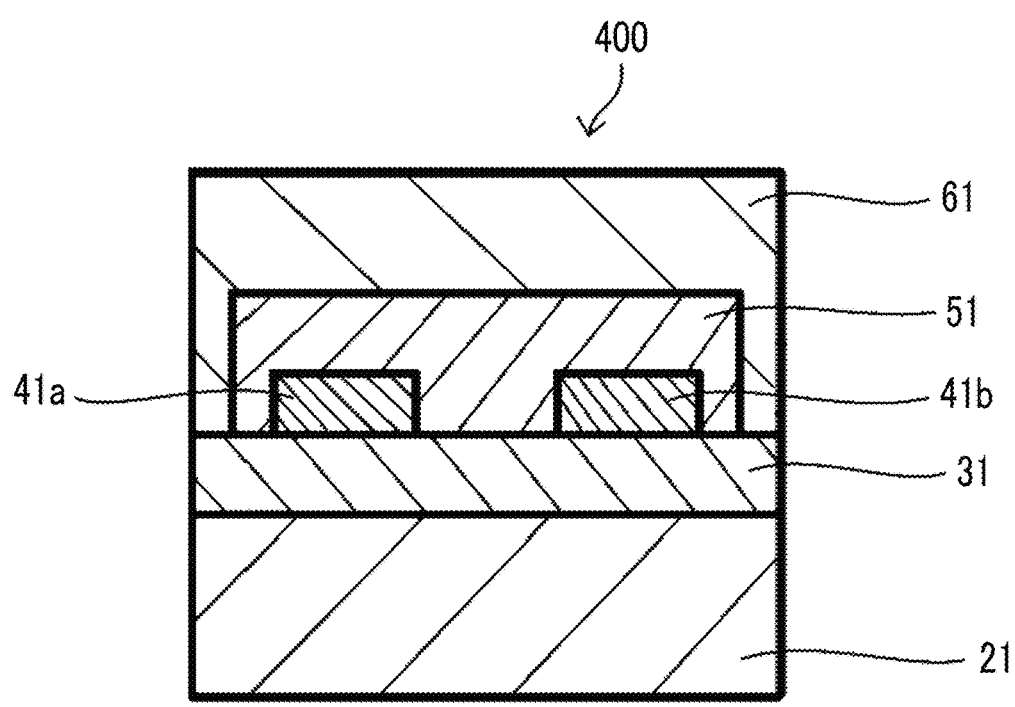
FIG. 4 is a schematic cross-sectional view showing another aspect of the bottom gate-bottom contact type organic semiconductor transistor as an example of the organic semiconductor transistor according to the present invention.

[Manufacturing Examples 2-1 to 2-108, Comparative Manufacturing Examples 2-1 to 2-4]
Manufacturing of Bottom Gate-Bottom Contact Type Organic Semiconductor Transistor A bottom gate-bottom contact type organic thin film transistor 400 shown in FIG. 4 was manufactured as follows.
<Gate Electrode, Gate Insulating Layer>
A conductive silicon substrate (gate electrode, 0.7 mm) on which a $SiO_2$ thermal oxide film (gate insulating layer, 350 nm) was formed was used. The surface of the $SiO_2$ thermal oxide film was treated with β-PTS.
<Formation of Source Electrode and Drain Electrode>
Au was vapor-deposited on the β-PTS-treated surface and was patterned using a laser such that the channel length L was 5 μm and the channel width W was 50 μm. The thickness of each electrode was 30 nm.
<Formation of Organic Semiconductor Film (Layer)>
Each of the compounds 1 to 108 and the comparative compounds 1 to 4 shown in the tables was vacuum-deposited (substrate temperature: normal temperature, vacuum degree: $1 \times 10^{-5}$ to $1 \times 10^{-4}$ Pa) so as to cover the source electrode and the drain electrode to form an organic semiconductor film (thickness: 50 nm).
<Patterning>
By scribing the vicinity of an organic semiconductor transistor-forming region with a needle, the organic semiconductor transistor-forming region and the other regions were separated from each other.
As manufacturing examples corresponding to the compounds 1 to 108, Manufacturing Examples 2-1 to 2-108 were used. As manufacturing examples corresponding to the comparative compounds 1 to 4, Comparative Manufacturing Examples 2-1 to 2-4 were used.
In Manufacturing Examples 2-1 to 2-108 and Comparative Manufacturing Examples 2-1 to 2-4, all the crystal domain sizes of the organic semiconductor films were in a range of 5 nm to 80 nm.

Regarding the organic semiconductor transistor obtained in each of Manufacturing Examples 2-1 to 2-108 and Comparative Manufacturing Examples 2-1 to 2-4, the average mobility, the variation in mobility, the yield, the $V_{th}$ shift, and the hysteresis were evaluated using the above-described evaluation methods. As a result, in the organic semiconductor transistors according to Comparative Manufacturing Examples 2-1 to 2-4 in which the organic semiconductor layers were formed using the comparative compounds 1 to 4, respectively, that were not the compounds defined by the present invention, the average mobility was low, and the yield was also poor as in Comparative Manufacturing Examples 1-1 to 1-4.

On the other hand, in the organic semiconductor transistors according to Manufacturing Examples 2-1 to 2-108 in which the organic semiconductor film according to the present invention was used as the organic semiconductor layer, the average mobility was excellent, the variation in mobility was small, and the yield was also excellent. In addition, the $V_{th}$ shift was also suppressed to be low, and the evaluation of hysteresis was also excellent. This way, it can be seen that, in the organic semiconductor transistor according to the embodiment of the present invention, the mobility is excellent, a variation in performance between elements is small, and power consumption is small.

[Comparative Manufacturing Example 2-5]
Manufacturing of Bottom Gate-Bottom Contact Type Organic Semiconductor Transistor An organic semiconductor transistor was manufactured under the same conditions as those of Manufacturing Example 2-1, except that the formation of the organic semiconductor film was changed as follows.
<Formation of Organic Semiconductor Film (Layer)>
The compound 1 was dissolved in anisole to prepare a coating solution including 0.1 mass % of the compound 1. Using this coating solution, the organic semiconductor film (thickness: 30 nm) was formed so as to cover the source electrode and the drain electrode with the same method as the method (edge casting method) described in paragraphs "0187" and "0188" of JP2015-195362A.
The crystalline structure of the formed organic semiconductor film was able to be observed with a polarizing microscope. The crystal domain size of the organic semiconductor film was much more than 10 μm, and a crystal domain having a size of 1 mm or more was also observed.
Regarding the organic semiconductor transistor according to Comparative Manufacturing Example 2-5, the average mobility, the variation in mobility, the yield, the $V_{th}$ shift, and the hysteresis were evaluated using the above-described evaluation methods. The results are shown in the following table together with the evaluation results of the organic semiconductor transistor according to Manufacturing Example 2-1.

TABLE 72

| | Compound | Average Mobility | Variation in Mobility | Yield | Vth Shift | Hysteresis |
|---|---|---|---|---|---|---|
| Manufacturing Example 2-1 | Compound 1 | A | A | A | A | A |
| Comparative Manufacturing Example 2-5 | Compound 1 | B | E | E | D | B |

As shown in the table, in the organic semiconductor transistor according to Comparative Manufacturing Example 2-5 in which the organic semiconductor film was formed using a solution process and the crystal domain size of the organic semiconductor film was more than the range defined by the present invention, the average mobility was lower than and the variation in mobility was also larger than those of the organic semiconductor transistor according to Manufacturing Example 2-1. In the organic semiconductor transistor according to Comparative Manufacturing Example 2-5, an element having a high carrier mobility was obtained; however, an element having a significantly low carrier mobility appeared with a high probability, and the yield also deteriorated. In addition, the $V_{th}$ shift was high, the hysteresis was also poor, and the result was also poor from the viewpoint of power consumption.

Organic semiconductor transistors were manufactured under the same conditions as those of Comparative Manufacturing Example 2-5, except that the compounds 2 to 108 were used instead of the compound 1. In a case where the performances of the organic semiconductor transistors were compared to the performance of the organic semiconductor transistors according to Manufacturing Examples 2-2 to 2-108 in which the compounds corresponding to Manufacturing Examples 2-2 to 2-108 were used (that is, compounds forming the organic semiconductor layers were the same), all the results regarding the variation in mobility, the yield, the $V_{th}$ shift, and the hysteresis were poor.

[Manufacturing Examples 3-1 to 3-108, Comparative Manufacturing Examples 3-1 to 3-4] Manufacturing of Bottom Gate-Top Contact Type Organic Semiconductor Transistor Organic semiconductor transistors according to Manufacturing Examples 3-1 to 3-108 and Comparative Manufacturing Examples 3-1 to 3-4 were manufactured under the same conditions of those of Manufacturing Examples 1-1 to 1-108 and Comparative Manufacturing Examples 1-1 to 1-4, respectively, except that the organic semiconductor layer was heated at 150° C. for 1 hour before patterning and after the formation of the source electrode and the drain electrode.

Regarding the organic semiconductor transistor obtained in each of Manufacturing Examples 3-1 to 3-108 and Comparative Manufacturing Examples 3-1 to 3-4, the average mobility, the variation in mobility, the yield, the $V_{th}$ shift, and the hysteresis were evaluated using the above-described evaluation methods. As a result, in the organic semiconductor transistors according to Comparative Manufacturing Examples 3-1 to 3-4 in which the organic semiconductor layers were formed using the comparative compounds 1 to 4, respectively, that were not the compounds defined by the present invention, the mobility was low, and the yield was also poor.

On the other hand, in the organic semiconductor transistors according to Manufacturing Examples 3-1 to 3-108 in which the organic semiconductor layers were formed using the organic semiconductor film according to the present invention, the average mobility was excellent, the variation in mobility between elements was also suppressed, and the yield was also excellent. In addition, the $V_{th}$ shift was also suppressed to be low, and the evaluation of hysteresis was also excellent. This way, it can be seen that, in the organic semiconductor transistor according to the embodiment of the present invention, a variation in performance between elements is small, and power consumption is small.

[Comparative Manufacturing Example 3-5] Manufacturing of Bottom Gate-Top Contact Type Organic Semiconductor Transistor An organic semiconductor transistor according to Comparative Manufacturing Example 3-5 was manufactured under the same conditions of those of Comparative Manufacturing Example 1-5, respectively, except that the organic semiconductor layer was heated at 150° C. for 1 hour before patterning and after the formation of the source electrode and the drain electrode.

Regarding the organic semiconductor transistor according to Comparative Manufacturing Example 3-5, the average mobility, the variation in mobility, the yield, the $V_{th}$ shift, and the hysteresis were evaluated using the above-described evaluation methods. The results are shown in the following table together with the evaluation results of the organic semiconductor transistor according to Manufacturing Example 3-1.

TABLE 73

|  | Compound | Average Mobility | Variation in Mobility | Yield | Vth Shift | Hysteresis |
| --- | --- | --- | --- | --- | --- | --- |
| Manufacturing Example 3-1 | Compound 1 | A | A | A | A | A |
| Comparative Manufacturing Example 3-5 | Compound 1 | C | D | D | B | B |

As shown in the table, in the organic semiconductor transistor according to Comparative Manufacturing Example 3-5 in which the organic semiconductor film was formed using a solution process, the crystal domain size of the organic semiconductor film was more than the range defined by the present invention, and a heat treatment was performed, the results of all the evaluations of the average mobility, the variation in mobility, the yield, the Vth shift, and the hysteresis were also lower than that of the organic semiconductor transistor according to Manufacturing Example 3-1. In a case where the organic semiconductor layer of the organic semiconductor transistor according to Comparative Manufacturing Example 3-5 was observed with a polarizing microscope, a large crystal domain boundary was present between channels, and cracks were formed in many cases.

Organic semiconductor transistors were manufactured under the same conditions as those of Comparative Manufacturing Example 3-5, except that the compounds 2 to 108 were used instead of the compound 1. In a case where the performances of the organic semiconductor transistors were compared to the performance of the organic semiconductor transistors according to Manufacturing Examples 3-2 to 3-108 in which the compounds corresponding to Manufacturing Examples 3-2 to 3-108 were used (that is, compounds forming the organic semiconductor layers were the same), all the results regarding the variation in mobility, the yield, the $V_{th}$ shift, and the hysteresis were poor.

[Manufacturing Examples 4-1 to 4-108, Comparative Manufacturing Examples 4-1 to 4-4] Manufacturing of Bottom Gate-Bottom Contact Type Organic Semiconductor Transistor Organic semiconductor transistors according to Manufacturing Examples 4-1 to 4-108 and Comparative Manufacturing Examples 4-1 to 4-4 were manufactured under the same conditions of those of Manufacturing Examples 2-1 to 2-108 and Comparative Manufacturing Examples 2-1 to 2-4, respectively, except that the method of forming the source electrode and the drain electrode was changed as follows, the method of forming the organic semiconductor film was changed as follows, and the patterning of scribing the vicinity of the organic semiconductor transistor-forming region with a needle was not performed.

<Formation of Source Electrode and Drain Electrode>

Chromium and Au were patterned and vapor-deposited on the β-PTS-treated surface through a mask to form the source electrode and the drain electrode. The thickness of each electrode was 30 nm.

<Formation of Organic Semiconductor Film (Layer)>

Each of the compounds 1 to 108 and the comparative compounds 1 to 4 shown in the tables was patterned through a mask and vacuum-deposited (substrate temperature: normal temperature, vacuum degree: $1\times10^{-5}$ to $1\times10^{-4}$ Pa) so as to cover the source electrode and the drain electrode to form an organic semiconductor film (thickness: 50 nm).

In Manufacturing Examples 4-1 to 4-108 and Comparative Manufacturing Examples 4-1 to 4-4, all the crystal domain sizes of the organic semiconductor films were in a range of 5 nm to 80 nm.

Regarding the organic semiconductor transistor obtained in each of Manufacturing Examples 4-1 to 4-108 and Comparative Manufacturing Examples 4-1 to 4-4, the average mobility, the variation in mobility, the yield, the $V_{th}$ shift, and the hysteresis were evaluated using the above-described evaluation methods. As a result, in the organic semiconductor transistors according to Comparative Manufacturing Examples 4-1 to 4-4 in which the organic semiconductor layers were formed using the comparative compounds 1 to 4, respectively, that were not the compounds defined by the present invention, the average mobility was low, and the yield was also poor.

On the other hand, in the organic semiconductor transistors according to Manufacturing Examples 4-1 to 4-108 in which the organic semiconductor film according to the present invention was used as the organic semiconductor layer, the average mobility was excellent, the variation in mobility between elements was also suppressed, and the yield was also excellent. In addition, the $V_{th}$ shift was also suppressed to be low, and the evaluation of hysteresis was also excellent. This way, it can be seen that, in the organic semiconductor transistor according to the embodiment of the present invention, the mobility is excellent, a variation in performance between elements is small, and power consumption is small.

[Comparative Manufacturing Example 4-5]
Manufacturing of Bottom Gate-Bottom Contact Type Organic Semiconductor Transistor An organic semiconductor transistor according to Comparative Manufacturing Example 4-5 was manufactured under the same conditions as those of the organic semiconductor transistor according to Comparative Manufacturing Example 2-5, except that the method of forming the source electrode and the drain electrode was changed as follows, the method of forming the organic semiconductor film was changed as follows, and the patterning of scribing the vicinity of the organic semiconductor transistor-forming region with a needle was not performed.

<Formation of Source Electrode and Drain Electrode>

Chromium and Au were patterned and vapor-deposited on the β-PTS-treated surface through a mask to form the source electrode and the drain electrode. The thickness of each electrode was 30 nm.

<Formation of Organic Semiconductor Film (Layer)>

The compound 1 shown above in the table was dissolved in tetralin such that the concentration thereof was 0.5 mass %. Using an ink jet printer (DMP 2831, manufactured by Fuji Film Co., Ltd.), this solution was applied in a state where it was patterned so as to cover the source electrode and the drain electrode. As a result, an organic semiconductor film was formed.

Regarding the organic semiconductor transistor according to Comparative Manufacturing Example 4-5, the average mobility, the variation in mobility, the yield, the $V_{th}$ shift, and the hysteresis were evaluated using the above-described evaluation methods. The results are shown in the following table together with the evaluation results of the organic semiconductor transistor according to Manufacturing Example 4-1.

TABLE 74

| | Compound | Average Mobility | Variation in Mobility | Yield | Vth Shift | Hysteresis |
|---|---|---|---|---|---|---|
| Manufacturing Example 4-1 | Compound 1 | A | A | A | A | A |
| Comparative Manufacturing Example 4-5 | Compound 1 | C | E | E | C | C |

In the organic semiconductor transistor according to Comparative Manufacturing Example 4-5, the average mobility, the variation in mobility, the yield, the $V_{th}$ shift, and the hysteresis were lower than those of the organic semiconductor transistor according to Manufacturing Example 4-1. In a case where the organic semiconductor film of the organic semiconductor transistor according to Comparative Manufacturing Example 4-5 was observed with a polarizing microscope, crystals precipitated only on the source electrode and the drain electrode and were not formed between channels. The reason for this is presumed to be that the surface energy of the electrode surface was higher than that of the insulating layer such that ink was attracted to the electrode and was not likely to be present between channels.

EXPLANATION OF REFERENCES

10: substrate
20: gate electrode
30: gate insulating layer (film)
40: source electrode
42: drain electrode
50: organic semiconductor layer (film)

60: sealing layer
100, 200: organic semiconductor transistor
21: silicon substrate (gate electrode)
31: thermal oxide film (gate insulating layer)
41a: source electrode
41b: drain electrode
51: organic semiconductor layer
61: sealing layer
300, 400: organic semiconductor transistor

What is claimed is:

1. A microcrystalline organic semiconductor film comprising:
a compound represented by the following Formula (1) that has a molecular weight of 3000 or lower and in which a crystal domain size is 1 nm to 100 nm,

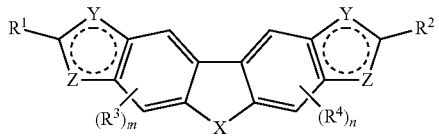

Formula (1)

in Formula (1),
X represents an oxygen atom, a sulfur atom, a selenium atom, a tellurium atom, or $NR^5$,
Y and Z each independently represent $CR^6$, an oxygen atom, a sulfur atom, a selenium atom, a nitrogen atom, or $NR^7$,
the 5-membered ring comprising Y and Z is an aromatic heterocycle,
$R^1$ and $R^2$ in Formula (1) are bonded directly to the 5-membered ring or indirectly through a divalent group A,
$R^3$ and $R^4$ in Formula (1) are bonded directly to a ring-constituting atom of a benzene ring or indirectly through the divalent group A,
the divalent group A is a group selected from —O—, —S—, $—NR^8—$, —CO—, —SO—, or —SO$_2$— or is a group in which two or more selected from —O—, —S—, $—NR^8—$, —CO—, —SO—, or —SO$_2$— are linked to each other,
$R^1$, $R^2$, $R^5$, $R^6$, $R^7$, and $R^8$ each independently represent a hydrogen atom, an alkyl group, an alkenyl group, an alkynyl group, an aryl group, or a heteroaryl group,
$R^3$ and $R^4$ each independently represent a halogen atom, an alkyl group, an alkenyl group, an alkynyl group, an aryl group, or a heteroaryl group,
m and n each independently represent an integer of 0 to 2, and
a configuration in which X represents an oxygen atom or a sulfur atom and the 5-membered ring comprising Y and Z is an imidazole ring and a configuration in which X represents a sulfur atom, Y represents CH, Z represents a sulfur atom, both $R^1$ and $R^2$ represent a hydrogen atom, and both m and n represent 0 are excluded from the compound represented by Formula (1).

2. The microcrystalline organic semiconductor film according to claim 1,
wherein the 5-membered ring comprising Y and Z is a ring selected from a thiophene ring, a furan ring, a selenophene ring, a pyrrole ring, a thiazole ring, or an oxazole ring.

3. The microcrystalline organic semiconductor film according to claim 1,
wherein the number of carbon atoms in each of $R^1$, $R^2$, $R^3$, and $R^4$ is 30 or less.

4. The microcrystalline organic semiconductor film according to claim 1,
wherein $R^1$ and $R^2$ each independently represent an alkyl group having 20 or less carbon atoms, an aryl group having 20 or less carbon atoms, or a heteroaryl group having 20 or less carbon atoms.

5. The microcrystalline organic semiconductor film according to claim 1,
wherein $R^1$ and $R^2$ are the same as each other,
$R^3$ and $R^4$ are the same as each other, and
m and n are the same as each other.

6. The microcrystalline organic semiconductor film according to claim 1,
wherein both m and n represent 0.

7. The microcrystalline organic semiconductor film according to claim 1,
wherein the compound represented by the following Formula (1) that has a molecular weight of 3000 or lower is represented by the following Formula (2) or (3),

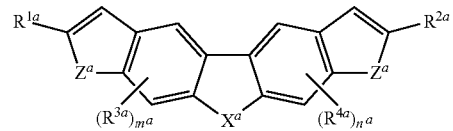

Formula (2)

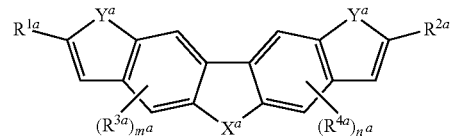

Formula (3)

in Formulae (2) and (3),
$X^a$ represents an oxygen atom, a sulfur atom, or a selenium atom,
$Y^a$ and $Z^a$ each independently represent an oxygen atom, a sulfur atom, a selenium atom, or $NR^{7a}$,
$R^{7a}$ has the same definition as $R^7$ in Formula (1),
$R^{1a}$, $R^{2a}$, $R^{3a}$, $R^{4a}$, $m^a$, and $n^a$ have the same definitions as $R^1$, $R^2$, $R^3$, $R^4$, m, and n in Formula (1), respectively,
$R^{1a}$, $R^{2a}$, $R^{3a}$, and $R^{4a}$ are also bonded in the same manner as $R^1$, $R^2$, $R^3$, and $R^4$ in Formula (1), respectively, and
a configuration in which $X^a$ represents a sulfur atom, $Z^a$ represents a sulfur atom, both $R^{1a}$ and $R^{2a}$ represent a hydrogen atom, and both $m^a$ and $n^a$ represent 0 is excluded from the compound represented by Formula (2).

8. The microcrystalline organic semiconductor film according to claim 7,
wherein the number of carbon atoms in each of $R^{1a}$, $R^{2a}$, $R^{3a}$ and $R^{4a}$ is 30 or less.

9. The microcrystalline organic semiconductor film according to claim 7,
wherein $R^{1a}$ and $R^{2a}$ each independently represent an alkyl group having 20 or less carbon atoms, an aryl group having 20 or less carbon atoms, or a heteroaryl group having 20 or less carbon atoms.

10. The microcrystalline organic semiconductor film according to claim 7,
wherein $R^{1a}$ and $R^{2a}$ are the same as each other,
$R^{3a}$ and $R^{4a}$ are the same as each other, and
$m^a$ and $n^a$ are the same as each other.

11. The microcrystalline organic semiconductor film according to claim 7,
wherein the compound represented by Formula (2) that has a molecular weight of 3000 or lower is represented by the following Formula (4), and
the compound represented by Formula (3) that has a molecular weight of 3000 or lower is represented by the following Formula (5),

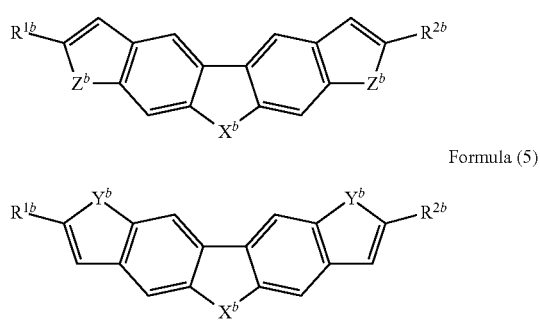

Formula (4)

Formula (5)

in Formulae (4) and (5),
$X^b$, $Y^b$, and $Z^b$ each independently represent an oxygen atom, a sulfur atom, or a selenium atom,
$R^{1b}$ and $R^{2b}$ have the same definitions as $R^{1a}$ and $R^{2a}$ in Formula (2), respectively,
of $R^{1b}$ and $R^{2b}$ atom are also bonded in the same manner as of $R^{1a}$ and $R^{2a}$ in Formula (2), respectively, and
a configuration in which $X^b$ represents a sulfur atom, $Z^b$ represents a sulfur atom, and both $R^{1b}$ and $R^{2b}$ represent a hydrogen atom is excluded from the compound represented by Formula (4).

12. The microcrystalline organic semiconductor film according to claim 11,
wherein the number of carbon atoms in each of $R^{1b}$ and $R^{2b}$ is 30 or less.

13. The microcrystalline organic semiconductor film according to claim 11,
wherein $R^{1b}$ and $R^{2b}$ each independently represent an alkyl group having 20 or less carbon atoms, an aryl group having 20 or less carbon atoms, or a heteroaryl group having 20 or less carbon atoms.

14. The microcrystalline organic semiconductor film according to claim 11,
wherein $R^{1b}$ and $R^{2b}$ comprise an aliphatic hydrocarbon group.

15. The microcrystalline organic semiconductor film according to claim 14, wherein $R^{1b}$ and $R^{2b}$ each independently represent an aryl group comprising a linear aliphatic hydrocarbon group as a substituent or a heteroaryl group comprising a linear aliphatic hydrocarbon group as a substituent.

16. The microcrystalline organic semiconductor film according to claim 1, which is a vapor-deposited film.

17. An organic semiconductor transistor comprising:
the microcrystalline organic semiconductor film according to claim 1 as an organic semiconductor layer.

18. The organic semiconductor transistor according to claim 17,
wherein the organic semiconductor transistor is a bottom gate type.

19. The organic semiconductor transistor according to claim 17,
wherein the organic semiconductor transistor is a bottom contact type.

20. A method of manufacturing an organic semiconductor transistor comprising:
vapor-depositing a compound represented by the following Formula (1) that has a molecular weight of 3000 or lower to form an organic semiconductor layer,

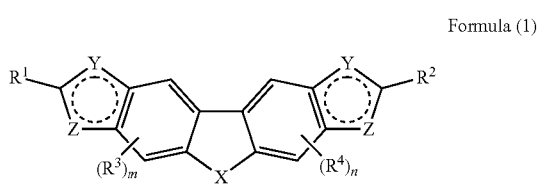

Formula (1)

in Formula (1),
X represents an oxygen atom, a sulfur atom, a selenium atom, a tellurium atom, or $NR^5$,
Y and Z each independently represent $CR^6$, an oxygen atom, a sulfur atom, a selenium atom, a nitrogen atom, or $NR^7$,
the 5-membered ring comprising Y and Z is an aromatic heterocycle,
$R^1$ and $R^2$ in Formula (1) are bonded directly to the 5-membered ring or indirectly through a divalent group A,
$R^3$ and $R^4$ in Formula (1) are bonded directly to a ring-constituting atom of a benzene ring or indirectly through the divalent group A,
the divalent group A is a group selected from —O—, —S—, —$NR^8$—, —CO—, —SO—, or —$SO_2$— or is a group in which two or more selected from —O—, —S—, —$NR^8$—, —CO—, —SO—, or —$SO_2$— are linked to each other,
$R^1$, $R^2$, $R^5$, $R^6$, $R^7$, and $R^8$ each independently represent a hydrogen atom, an alkyl group, an alkenyl group, an alkynyl group, an aryl group, or a heteroaryl group,
$R^3$ and $R^4$ each independently represent a halogen atom, an alkyl group, an alkenyl group, an alkynyl group, an aryl group, or a heteroaryl group,
m and n each independently represent an integer of 0 to 2, and
a configuration in which X represents an oxygen atom or a sulfur atom and the 5-membered ring comprising Y and Z is an imidazole ring and a configuration in which X represents a sulfur atom, Y represents CH, Z represents a sulfur atom, both $R^1$ and $R^2$ represent a hydrogen atom, and both m and n represent 0 are excluded from the compound represented by Formula (1).

21. A method of manufacturing an organic semiconductor transistor according to claim 17 comprising:
forming the microcrystalline organic semiconductor film according to claim 1 and patterning the microcrystalline organic semiconductor film to form an organic semiconductor layer.

* * * * *